United States Patent
Warren et al.

(10) Patent No.: US 6,951,561 B2
(45) Date of Patent: Oct. 4, 2005

(54) SPINAL STABILIZATION DEVICE

(75) Inventors: Christopher Warren, Aliso Viejo, CA (US); Brad S. Culbert, Rancho Santa Margarita, CA (US)

(73) Assignee: Triage Medical, Inc., Irvine, CA (US)

( * ) Notice: Subject to any disclaimer, the term of this patent is extended or adjusted under 35 U.S.C. 154(b) by 28 days.

(21) Appl. No.: 10/840,504

(22) Filed: May 6, 2004

(65) Prior Publication Data

US 2005/0033289 A1 Feb. 10, 2005

Related U.S. Application Data

(60) Provisional application No. 60/468,377, filed on May 6, 2003, provisional application No. 60/471,973, filed on May 20, 2003.

(51) Int. Cl.[7] .............................................. A61B 17/86
(52) U.S. Cl. .......................................... 606/73; 606/72
(58) Field of Search ............................... 606/60, 62, 63, 606/65, 66, 67, 68, 72, 73, 232

(56) References Cited

U.S. PATENT DOCUMENTS

| | | | |
|---|---|---|---|
| 2,077,804 A | 4/1937 | Morrison |
| 2,485,531 A | 10/1949 | Dzus et al. |
| 2,489,870 A | 10/1949 | Dzus |
| 3,489,143 A | 1/1970 | Holloran |
| 4,052,988 A | 10/1977 | Doddi et al. |
| 4,175,555 A | 11/1979 | Herbert |
| 4,275,717 A | 6/1981 | Bolesky |
| 4,463,753 A | 8/1984 | Gustilo |
| 4,632,101 A | 12/1986 | Freedland |
| 4,640,271 A | 2/1987 | Lower |
| 4,667,663 A | 5/1987 | Miyata |
| 4,688,561 A | 8/1987 | Reese |
| 4,721,103 A | 1/1988 | Freedland |
| 4,743,257 A | 5/1988 | Tormala |
| 4,790,304 A | 12/1988 | Rosenberg |
| 4,796,612 A | 1/1989 | Reese |
| 4,827,917 A | 5/1989 | Brumfield |
| 4,873,976 A | 10/1989 | Schreiber |
| 4,898,186 A | 2/1990 | Ikada et al. |
| 4,903,692 A | 2/1990 | Reese |
| 4,917,554 A | 4/1990 | Bronn |
| 4,940,467 A | 7/1990 | Tronzo |
| 4,968,317 A | 11/1990 | Tormala |
| 4,978,349 A | 12/1990 | Frigg |
| 5,059,193 A | 10/1991 | Kuslich |
| 5,062,849 A | 11/1991 | Schelhas |
| 5,092,891 A | 3/1992 | Kummer et al. |
| 5,098,433 A | 3/1992 | Freedland |
| 5,122,133 A | 6/1992 | Evans |
| 5,122,141 A | 6/1992 | Simpson et al. |
| 5,167,663 A | 12/1992 | Brumfield |

(Continued)

FOREIGN PATENT DOCUMENTS

EP     0 525 352 A1     2/1993

(Continued)

*Primary Examiner*—David O. Reip
(74) *Attorney, Agent, or Firm*—Knobbe, Martens, Olson & Bear, LLP.

(57) ABSTRACT

Disclosed is a bone fixation device of the type useful for connecting soft tissue or tendon to bone or for connecting two or more bones or bone fragments together. The device comprises an elongate body having a distal anchor thereon. An axially moveable proximal anchor is carried by the proximal end of the fixation device, to accommodate different bone dimensions and permit appropriate tensioning of the fixation device.

17 Claims, 37 Drawing Sheets

U.S. PATENT DOCUMENTS

| | | | |
|---|---|---|---|
| 5,167,664 | A | 12/1992 | Hodorek |
| 5,217,462 | A | 6/1993 | Asnis et al. |
| 5,242,447 | A | 9/1993 | Borzone |
| 5,246,441 | A | 9/1993 | Ross et al. |
| 5,250,049 | A | 10/1993 | Michael |
| 5,300,074 | A | 4/1994 | Frigg |
| 5,364,398 | A | 11/1994 | Chapman et al. |
| 5,370,646 | A | 12/1994 | Reese et al. |
| 5,449,359 | A | 9/1995 | Groiso |
| 5,452,748 | A | 9/1995 | Simmons et al. |
| 5,498,265 | A | 3/1996 | Asnis et al. |
| 5,501,695 | A | 3/1996 | Anspach, Jr. et al. |
| 5,536,127 | A | 7/1996 | Pennig |
| 5,549,610 | A | 8/1996 | Russell et al. |
| 5,626,613 | A | 5/1997 | Schmieding |
| 5,628,751 | A | 5/1997 | Sander et al. |
| 5,662,683 | A | 9/1997 | Kay |
| 5,669,915 | A | 9/1997 | Caspar et al. |
| 5,713,903 | A | 2/1998 | Sander et al. |
| 5,720,753 | A | 2/1998 | Sander et al. |
| 5,725,541 | A | 3/1998 | Anspach, Jr. et al. |
| 5,728,097 | A | 3/1998 | Mathews |
| 5,728,116 | A | 3/1998 | Rosenman |
| 5,741,282 | A | 4/1998 | Anspach, III et al. |
| 5,772,662 | A | 6/1998 | Chapman et al. |
| 5,782,865 | A | 7/1998 | Grotz |
| 5,849,004 | A | 12/1998 | Bramlet |
| 5,871,485 | A | 2/1999 | Rao et al. |
| 5,893,850 | A | 4/1999 | Cachia |
| 5,904,696 | A | 5/1999 | Rosenman |
| 5,908,422 | A | 6/1999 | Bresina |
| 5,928,235 | A | 7/1999 | Friedl |
| 5,928,244 | A | 7/1999 | Tovey et al. |
| 5,935,129 | A | 8/1999 | McDevitt et al. |
| 5,947,999 | A | 9/1999 | Groiso |
| 5,948,000 | A | 9/1999 | Larsen et al. |
| 5,954,747 | A | 9/1999 | Clark |
| 5,957,924 | A | 9/1999 | Tormala et al. |
| 5,968,044 | A | 10/1999 | Nicholson et al. |
| 5,976,139 | A | 11/1999 | Bramlet |
| 5,984,927 | A | 11/1999 | Wenstrom, Jr. et al. |
| 5,984,966 | A | 11/1999 | Kiema et al. |
| 5,989,255 | A | 11/1999 | Pepper et al. |
| 5,993,459 | A | 11/1999 | Larsen et al. |
| 5,997,538 | A | 12/1999 | Asnis et al. |
| 5,997,541 | A | 12/1999 | Schenk |
| 6,001,100 | A | 12/1999 | Sherman et al. |
| 6,001,101 | A | 12/1999 | Augagneur et al. |
| 6,004,327 | A | 12/1999 | Asnis et al. |
| 6,005,161 | A | 12/1999 | Brekke et al. |
| 6,007,566 | A | 12/1999 | Wenstrom, Jr. |
| 6,007,580 | A | 12/1999 | Lehto et al. |
| 6,010,513 | A | 1/2000 | Tormala et al. |
| 6,015,410 | A | 1/2000 | Tormala et al. |
| 6,019,762 | A | 2/2000 | Cole |
| 6,036,701 | A | 3/2000 | Rosenman |
| 6,068,648 | A | 5/2000 | Cole et al. |
| 6,083,244 | A | 7/2000 | Lubbers et al. |
| 6,126,661 | A | 10/2000 | Faccioli et al. |
| 6,168,595 | B1 | 1/2001 | Durham et al. |
| 6,183,472 | B1 | 2/2001 | Lutz |
| 6,183,474 | B1 | 2/2001 | Bramlet et al. |
| 6,306,136 | B1 | 10/2001 | Baccelli |
| 6,319,254 | B1 | 11/2001 | Giet et al. |
| 6,355,043 | B1 | 3/2002 | Adam |
| 6,361,537 | B1 | 3/2002 | Anderson |
| 6,371,989 | B1 | 4/2002 | Chauvin et al. |
| 6,423,061 | B1 | 7/2002 | Bryant |
| 6,423,067 | B1 | 7/2002 | Eisermann |
| 6,458,134 | B1 | 10/2002 | Songer et al. |
| 6,468,277 | B1 | 10/2002 | Justin et al. |
| 6,468,309 | B1 | 10/2002 | Lieberman |
| 6,491,714 | B1 | 12/2002 | Bennett |
| 6,506,192 | B1 | 1/2003 | Gertzman et al. |
| 6,527,774 | B2 | 3/2003 | Lieberman |
| 6,544,265 | B2 | 4/2003 | Lieberman |
| 6,547,793 | B1 | 4/2003 | McGuire |
| 6,551,319 | B2 | 4/2003 | Lieberman |
| 6,551,322 | B1 | 4/2003 | Lieberman |
| 6,558,389 | B2 | 5/2003 | Clark et al. |
| 6,579,293 | B1 | 6/2003 | Chandran |
| 6,582,453 | B1 | 6/2003 | Tran et al. |
| 6,585,730 | B1 | 7/2003 | Foerster |
| 6,585,740 | B2 | 7/2003 | Schlapfer et al. |
| 6,589,249 | B2 | 7/2003 | Sater et al. |
| 6,599,297 | B1 | 7/2003 | Carlsson et al. |
| 2003/0063582 | A1 | 4/2003 | Culbert |

FOREIGN PATENT DOCUMENTS

| | | |
|---|---|---|
| EP | 0 853 929 A2 | 7/1998 |
| EP | 1 046 376 A1 | 4/2000 |
| FR | 2 699 065 | 12/1992 |
| FR | 2 728 778 | 12/1994 |
| FR | 2 745 709 | 3/1996 |
| FR | 2 800 601 | 11/1999 |
| FR | 2 801 189 | 11/1999 |
| FR | 2 808 182 | 4/2000 |
| GB | 2157788 A | 10/1985 |
| GB | 2173565 A | 10/1986 |
| JP | 64-52439 | 2/1989 |
| WO | WO 91/09572 | 12/1989 |

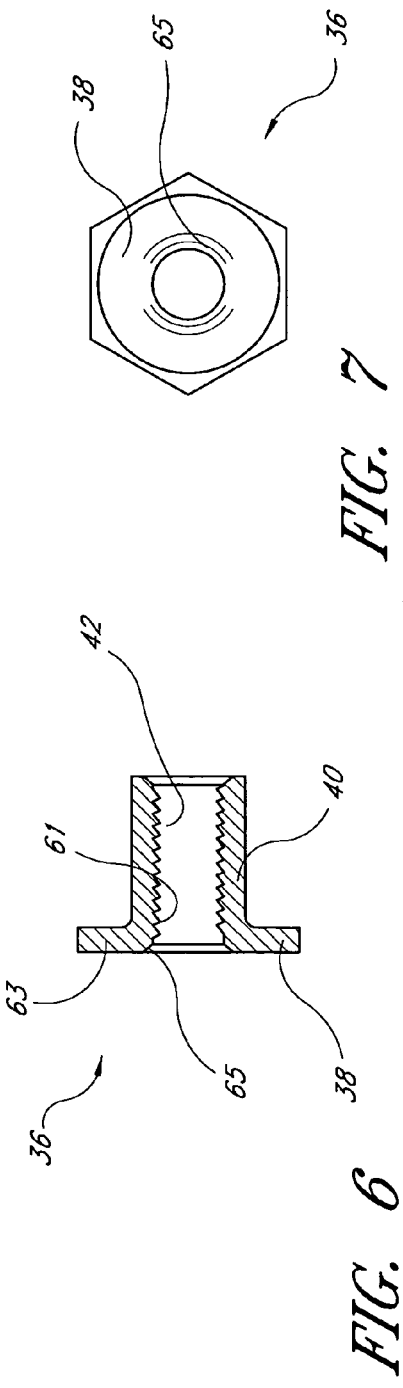
FIG. 6
FIG. 7
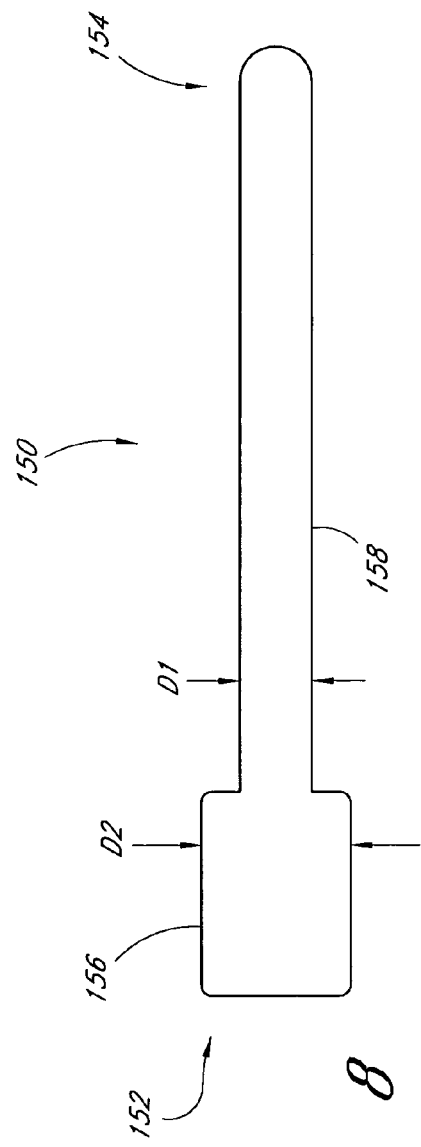
FIG. 8

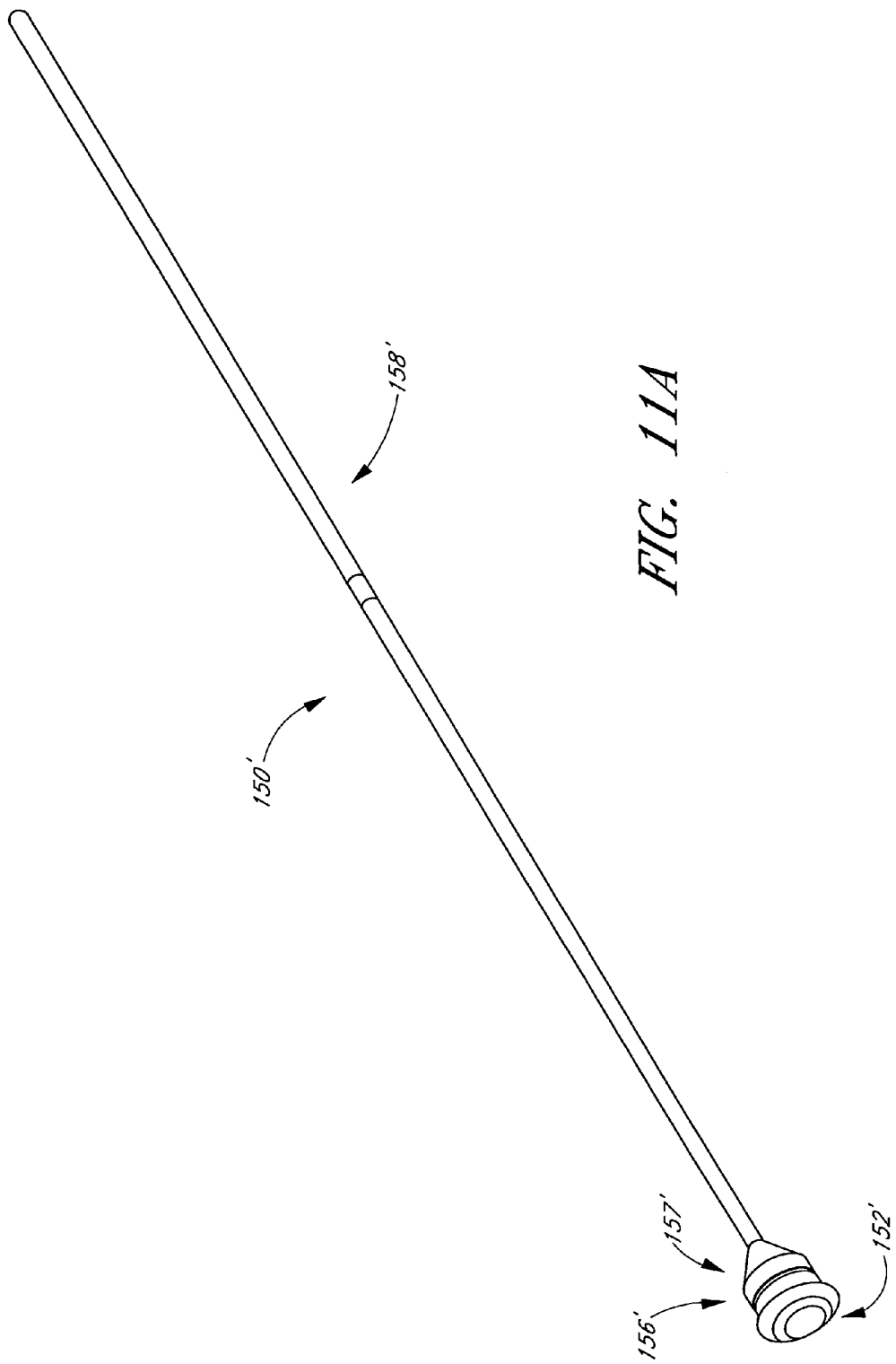

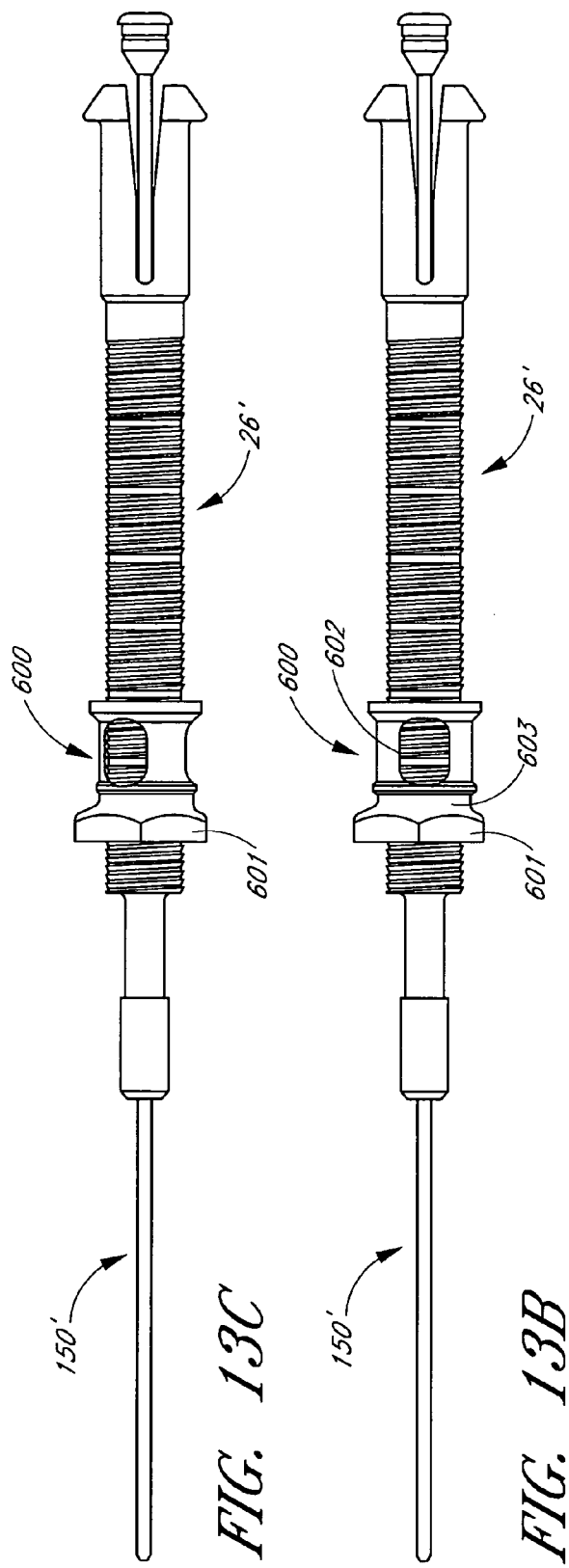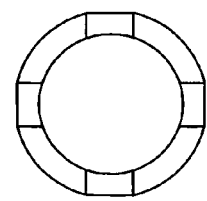
FIG. 13C  FIG. 13B  FIG. 13D

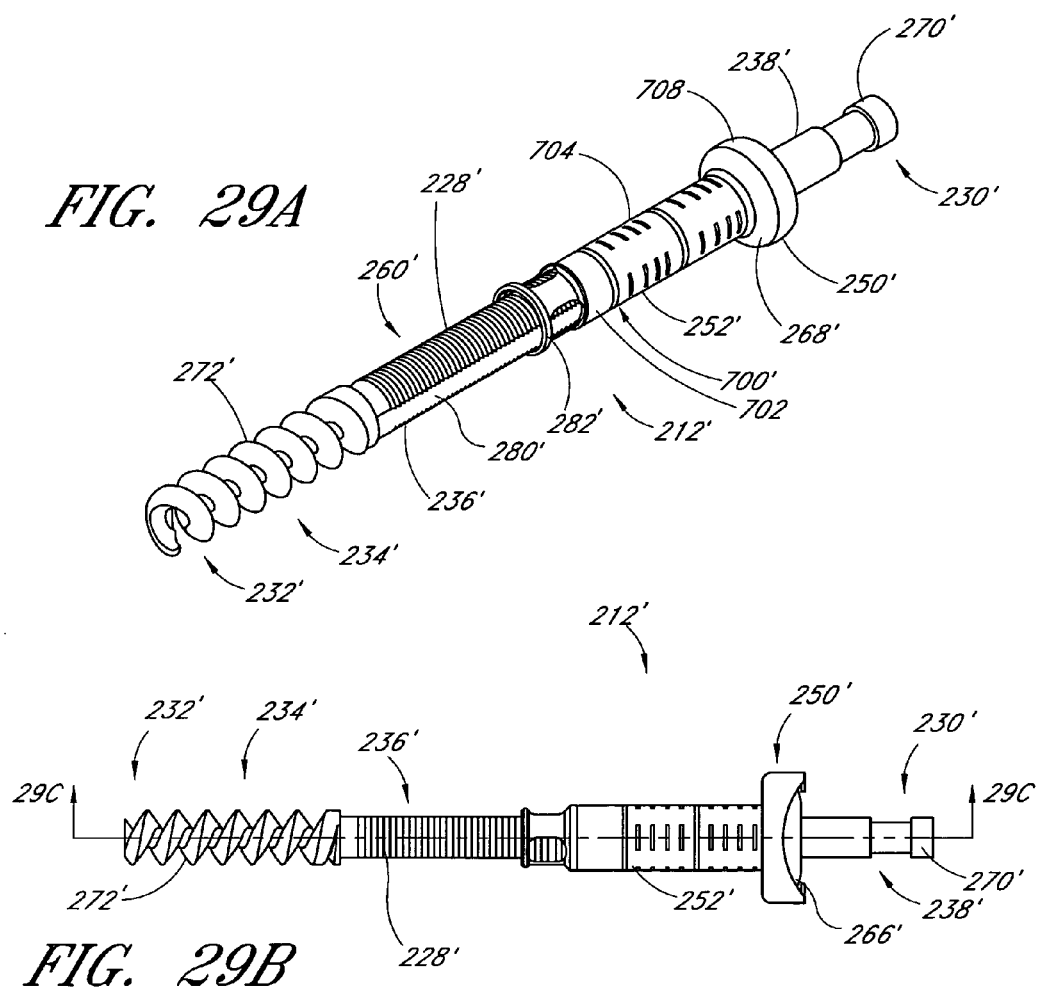
FIG. 29A
FIG. 29B
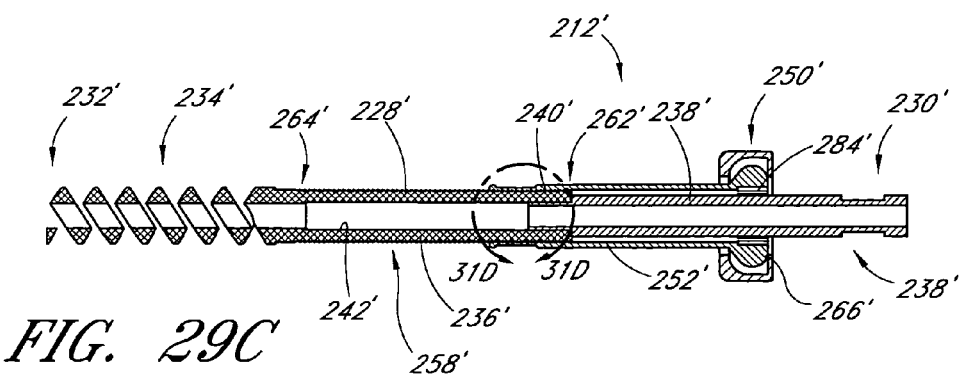
FIG. 29C

SPINAL STABILIZATION DEVICE

PRIORITY INFORMATION

This application claims the priority benefit under 35 U.S.C. § 119(e) of Provisional Application 60/468,377 filed May 6, 2003 and Provisional Application 60/471,973 filed May 20, 2003, the entire contents of these Provisional Applications are hereby incorporated by reference herein.

BACKGROUND OF THE INVENTION

1. Field of the Invention

The present invention relates to bone fixation devices, and, more particularly, to a bone fixation device with a proximal anchor.

2. Description of the Related Art

Bones which have been fractured, either by accident or severed by surgical procedure, must be kept together for lengthy periods of time in order to permit the recalcification and bonding of the severed parts. Accordingly, adjoining parts of a severed or fractured bone are typically clamped together or attached to one another by means of a pin or a screw driven through the rejoined parts. Movement of the pertinent part of the body may then be kept at a minimum, such as by application of a cast, brace, splint, or other conventional technique, in order to promote healing and avoid mechanical stresses that may cause the bone parts to separate during bodily activity.

The surgical procedure of attaching two or more parts of a bone with a pin-like device requires an incision into the tissue surrounding the bone and the drilling of a hole through the bone parts to be joined. Due to the significant variation in bone size, configuration, and load requirements, a wide variety of bone fixation devices have been developed in the prior art. In general, the current standard of care relies upon a variety of metal wires, screws, and clamps to stabilize the bone fragments during the healing process. Following a sufficient bone healing period of time, the percutaneous access site or other site may require re-opening to permit removal of the bone fixation device.

Long bone fractures are among the most common encountered in the human skeleton. Many of these fractures and those of small bones and small bone fragments must be treated by internal and external fixation methods in order to achieve good anatomical position, early mobilization, and early and complete rehabilitation of the injured patient.

The internal fixation techniques commonly followed today frequently rely upon the use of Kirschner wires (K-wires), intramedullary pins, wiring, plates, screws, and combinations of the foregoing. The particular device or combination of devices is selected to achieve the best anatomic and functional condition of the traumatized bone with the simplest operative procedure and with a minimal use of foreign-implanted stabilizing material. A variety of alternate bone fixation devices are also known in the art, such as, for example, those disclosed in U.S. Pat. No. 4,688,561 to Reese, U.S. Pat. No. 4,790,304 to Rosenberg, and U.S. Pat. No. 5,370,646 to Reese, et al.

A variety of elongated implants (nail, screw, pin, etc.) have been developed, which are adapted to be positioned along the longitudinal axis of the femoral neck with a leading (distal) end portion in the femoral head so as to stabilize a fracture of the femoral neck. The elongated implant may be implanted by itself or connected to another implant such as a side plate or intramedullary rod. The leading end portion of the implant typically includes means to positively grip the femoral head bone (external threads, expanding arms, etc.), but the inclusion of such gripping means can introduce several significant problems. First, implants with sharp edges on the leading end portion, such as the externally threaded implants, exhibit a tendency to migrate proximally towards the hip joint bearing surface after implantation. This can occur when the proximal cortical bone has insufficient integrity to resist distal movement of the screw head. Such proximal migration under physiological loading, which is also referred to as femoral head cut-out, can lead to significant damage to the adjacent hip joint. Also, the externally threaded implants can generate large stress concentrations in the bone during implantation which can lead to stripping of the threads formed in the bone and thus a weakened grip. The movable arms of known expanding arm devices are usually free at one end and attached at the other end to the main body of the leading end portion of the implant. As a result, all fatigue loading is concentrated at the attached ends of the arms and undesirably large bending moments are realized at the points of attachment. In addition, conventional threaded implants generally exhibit insufficient holding power under tension, such that the threads can be stripped out of the femoral head either by overtightening during the implantation procedure or during post operative loading by the patient's weight.

Bone fasteners may also be used for the stabilization of fractures and/or fusion of various portions of the spine. Such fasteners are often inserted through the pedicles of the vertebra and may be used in combination with a variety of longitudinal elements such as rods or plates which span two or more vertebra. These systems may be affixed to either the posterior or the anterior side of the spine.

Notwithstanding the variety of bone fasteners that have been developed in the prior art, there remains a need for a simple, adjustable bone fixation device which may be utilized to secure a fracture, secure soft tissue or tendon to the bone and/or provide stability between bones (e.g., vertebrae).

SUMMARY OF THE INVENTION

There is provided in accordance with one embodiment of the present invention, a fixation device for securing a first bone fragment to a second bone fragment or a first bone to a second bone. Alternatively, the fixation device may be used to secure soft tissue to a bone. The fixation device comprises an elongate pin, having a proximal end and a distal end. At least one axially advanceable anchor is carried by the pin.

In another embodiment, an orthopedic fixation device comprises an elongate body, having a proximal end and a distal end. A distal anchor is on the distal end of the body. A retention structure is positioned on the elongate body, proximal to the anchor. A proximal anchor is moveably carried by the elongate body. The proximal anchor comprises a tubular sleeve with a radially outward extending head. At least one complementary retention structure is on the proximal anchor and is configured for permitting proximal movement of the elongate body with respect to the proximal anchor but resisting distal movement of the elongate body with respect the proximal anchor. A washer is angularly moveable with respect to the longitudinal axis of the tubular sleeve. The washer has an aperture that is elongated with respect to a first axis such that the washer permits greater angular movement in a plane containing the first axis.

In another embodiment, an orthopedic fixation device comprises an elongate pin, having a proximal end, a distal end and a first retention structure. At least one distal anchor carried by the elongate pin. A proximal anchor is axially moveable with respect to the elongate pin and comprises a split ring positioned within an annular recess formed within the proximal anchor. The split ring has at least one gap formed between two ends. The split ring is moveable between a first position and a second position. The second position is located closer to the longitudinal axis of the elongate pin as compared to the first portion so as to engage the first retention structure and prevent proximal movement of the proximal anchor with respect to the elongated pin while the first position allows distal movement of the proximal anchor with respect to the pin. An anti-rotational structure prevents rotation of the split ring with the recess about the longitudinal axis of the elongate pin.

Further features and advantages of the present invention will become apparent to those of skill in the art in view of the detailed description of preferred embodiments which follows, when considered together with the attached claims and drawings.

BRIEF DESCRIPTION OF THE DRAWINGS

FIG. 6 is a cross-sectional view of a proximal anchor of the bone fixation device of FIG. 1.

FIG. 7 is a proximal end view of the proximal anchor of FIG. 6.

FIG. 8 is a side view of a expansion guide wire.

FIGS. 11A–E perspective, side, top and bottom views of a modified embodiment of a locking guidewire.

FIGS. 13A–D are perspective, side, and bottom views of the locking guidewire and pin body of FIGS. 10–11E.

FIGS. 29A–C are perspective, side, and longitudinal cross-sectional views of a modified embodiment of a fixation device.

FIGS. 30A–F are perspective, side, top, bottom and cross-sectional views of a modified embodiment of a proximal anchor.

DETAILED DESCRIPTION OF THE PREFERRED EMBODIMENT

Figure 1:
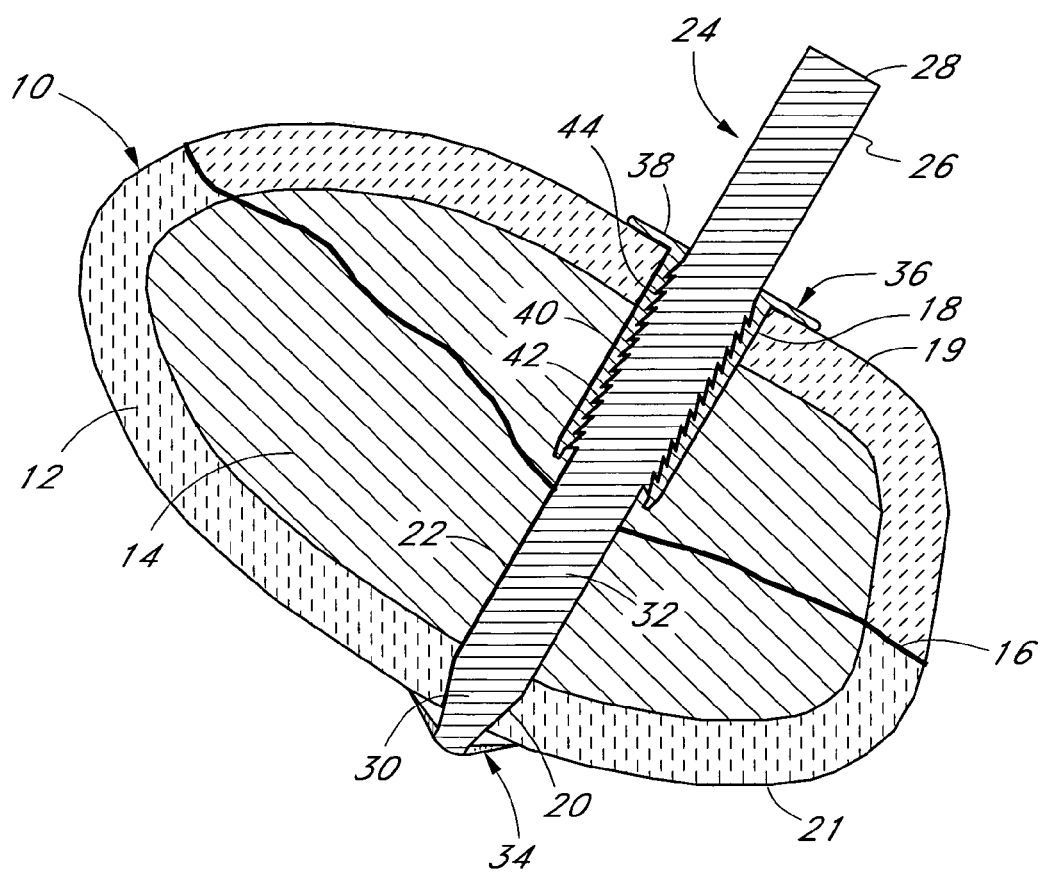
FIG. 1 is a cross-sectional schematic view of a bone fixation device positioned within a fractured bone.
Figure 3:
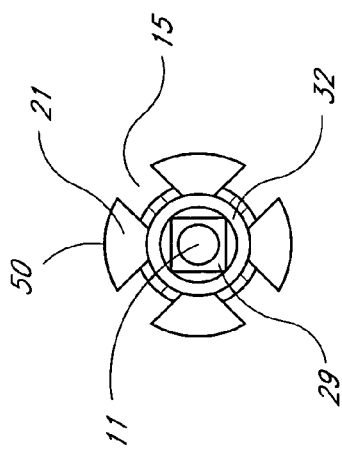
FIG. 3 is a distal end elevational view of the pin body of FIG. 2.

Although the application of the present invention will be initially disclosed in connection with the simplified bone fracture of FIG. 1, the methods and structures disclosed herein are intended for application in any of a wide variety of bones and fractures, as will be apparent to those of skill in the art in view of the disclosure herein. For example, the bone fixation device of the present invention is applicable in a wide variety of fractures and osteotomies in the hand, such as interphalangeal and metacarpophalangeal arthrodesis, transverse phalangeal and metacarpal fracture fixation, spiral phalangeal and metacarpal fracture fixation, oblique phalangeal and metacarpal fracture fixation, intercondylar phalangeal and metacarpal fracture fixation, phalangeal and metacarpal osteotomy fixation as well as others known in the art. A wide variety of phalangeal and metatarsal osteotomies and fractures of the foot may also be stabilized using the bone fixation device of the present invention. These include, among others, distal metaphyseal osteotomies such as those described by Austin and Reverdin-Laird, base wedge osteotomies, oblique diaphyseal, digital arthrodesis as well as a wide variety of others that will be known to those of skill in the art. Fractures and osteotomies and arthrodesis of the tarsal bones such as the calcaneus and talus may also be treated. Spiked washers can be used, attached to the collar or freely movable beneath the collar. The bone fixation device may be used with or without plate(s) or washer(s), all of which can be either permanent, absorbable or comprising both.

Fractures of the fibular and tibial malleoli, pilon fractures and other fractures of the bones of the leg may be fixated and stabilized with the present invention with or without the use of plates, both absorbable or non-absorbing types, and with alternate embodiments of the current invention. One example is the fixation of the medial malleolar avulsion fragment fixation with the radially and axially expanding compression device. Each of the foregoing may be treated in accordance with the present invention, by advancing one of the fixation devices disclosed herein through a first bone component, across the fracture, and into the second bone component to fix the fracture.

The fixation device of the present invention may also be used to attach tissue or structure to the bone, such as in ligament reattachment and other soft tissue attachment procedures. Plates and other implants may also be attached to bone, using either resorbable or nonreabsorbable fixation devices disclosed herein depending upon the implant and procedure. The fixation device may also be used to attach sutures to the bone, such as in any of a variety of tissue suspension procedures.

For example, peripheral applications for the fixation devices include utilization of the device for fastening soft tissue such as capsule, tendon or ligament to bone. It may also be used to attach a synthetic material such as marlex mesh, to bone or allograft material such as tensor fascia lata, to bone. In the process of doing so, retention of the material to bone may be accomplished with the collar as shown, with an enlarged collar to increase contact surface area, with a collar having a plurality of spikes to enhance the grip on adjacent tissue, or the pin and or collar may be modified to accept a suture or other material for facilitation of this attachment.

Specific examples include attachment of the posterior tibial tendon to the navicular bone in the Kidner operation. Navicular-cuneiform arthrodesis may be performed utilizing the device and concurrent attachment of the tendon may be accomplished. Attachment of the tendon may be accomplished in the absence of arthrodesis by altering the placement of the implant in the adjacent bone.

Ligament or capsule reattachment after rupture, avulsion of detachment, such as in the ankle, shoulder or knee can also be accomplished using the devices disclosed herein.

The bone fixation devices described herein may also be used in a variety of techniques to stabilize the spine. For example, the bone fixation devices may be used as pedicle or facet screws that may be unilaterally or bilaterally symmetrically mounted on adjacent or non-adjacent vertebrae and used in combination one or more linkage rods or plates to facilitate fusion of one or more vertebrae. The bone fixation devices disclosed herein may also be used as a fixation screw to secure two adjacent vertebra to each other in a trans-laminar, trans-facet or facet-pedicle (e.g., the Boucher technique) applications. One of skill of the art will also recognize that the bone fixation devices disclosed herein may be used for posterior stability after laminectomy, artificial disc replacement, repairing odontoid fractures and other fractures of the spine, and other applications for providing temporary or permanent stability in the spinal column.

The fixation devices may be used in combination with semi tubular, one-third tubular and dynamic compression plates, both of metallic and absorbable composition, preferably by modifying the collar to match the opening on the plate.

The cannulated design disclosed below can be fashioned to accept an antibiotic impregnated rod for the slow release of medication and/or bone growth or healing agents locally. This may be beneficial for prophylaxis, especially in open wounds, or when osteomyelitis is present and stabilization of fracture fragments is indicated. The central lumen can also be used to accept a titanium or other conductive wire or probe to deliver an electric current or electromagnetic energy to facilitate bone healing.

A kit may be assembled for field use by military or sport medical or paramedical personnel. This kit contains an implanting tool, and a variety of implant device size and types, a skin stapler, bandages, gloves, and basic tools for emergent wound and fracture treatment. Antibiotic rods would be included for wound prophylaxis during transport.

Referring to FIG. 1, there is illustrated generally a bone 10, shown in cross-section to reveal an outer cortical bone component 12 and an inner cancellous bone component 14. A fracture 16 is schematically illustrated as running through the bone 10 to at least partially divide the bone into what will for present purposes be considered a proximal component 19 and distal component 21. The fracture 16 is simplified for the purpose of illustrating the application of the present invention. However, as will be understood by those of skill in the art, the fracture 16 may extend through the bone at any of a wide variety of angles and depths. The bone fixation device of the present invention may be useful to stabilize two or more adjacent components of bone as long as each component may be at least partially traversed by the bone fixation device and anchored at opposing sides of the fracture to provide a sufficient degree of stabilization.

A proximal aperture 18 is provided in the proximal component 19 of the bone 10, such as by drilling, as will be discussed. A distal aperture 20 is provided in an opposing portion of bone such as in distal bone component 21 and is connected to the proximal aperture 18 by way of a through hole 22, as is known in the art, in a through hole application. The fixation device may also be useful in certain applications where the distal end of the device resides within the bone (i.e., a blind hole application).

The bone fixation device 24 is illustrated in FIG. 1 in its installed position within the through hole 22. The bone fixation device 24 generally comprises an elongate pin 26 having a proximal end 28, a distal end 30, and an elongate pin body 32 extending therebetween. The illustrated bone fixation 24 device and modified embodiments of the bone fixation device 24 are disclosed in U.S. Pat. No. 6,648,890, issued on Nov. 18, 2003, which is hereby incorporated by reference herein.

The distal end 30 of pin 26 is provided with a distal anchor 34, as will be discussed below. A proximal anchor 36 is also provided.

The radially interior surface of the tubular housing 40, in the illustrated embodiment, is provided with a plurality of retention structures 42. Retention structures 42 cooperate with corresponding retention structures 44 on the surface of pin body 32 to permit advancement of the proximal anchor 36 in the direction of the distal anchor 34 for properly sizing and tensioning the bone fixation device 24. Retention structures 42 then cooperate with retention structures 44 to provide a resistance to movement of the proximal anchor 36 in the proximal direction relative to pin body 32.

In the embodiment illustrated in FIGS. 6 and 7, the proximal anchor 36 comprise a collar 38 for contacting the proximal bone component 19. Collar 38 may comprises a radially-outwardly extending annular ramp or flange to optimize contact with the proximal bone component 19. Alternatively, proximal collar 38 may comprise one or more radially-outwardly extending stops, a frusto-conical plug, or other structures which stop the distal progress of proximal anchor 36 with respect to the through hole 22 or blind hole, depending upon the application. The collar 38 is connected to a tubular housing 40 adapted to coaxially receive the pin body 32 therethrough.

In use, the proximal projection of pin 26 which extends beyond the proximal anchor 36 after tensioning is preferably removed, such as by cutting, to minimize the projection of the bone fixation device 24 from the surface of the bone.

Figure 2:
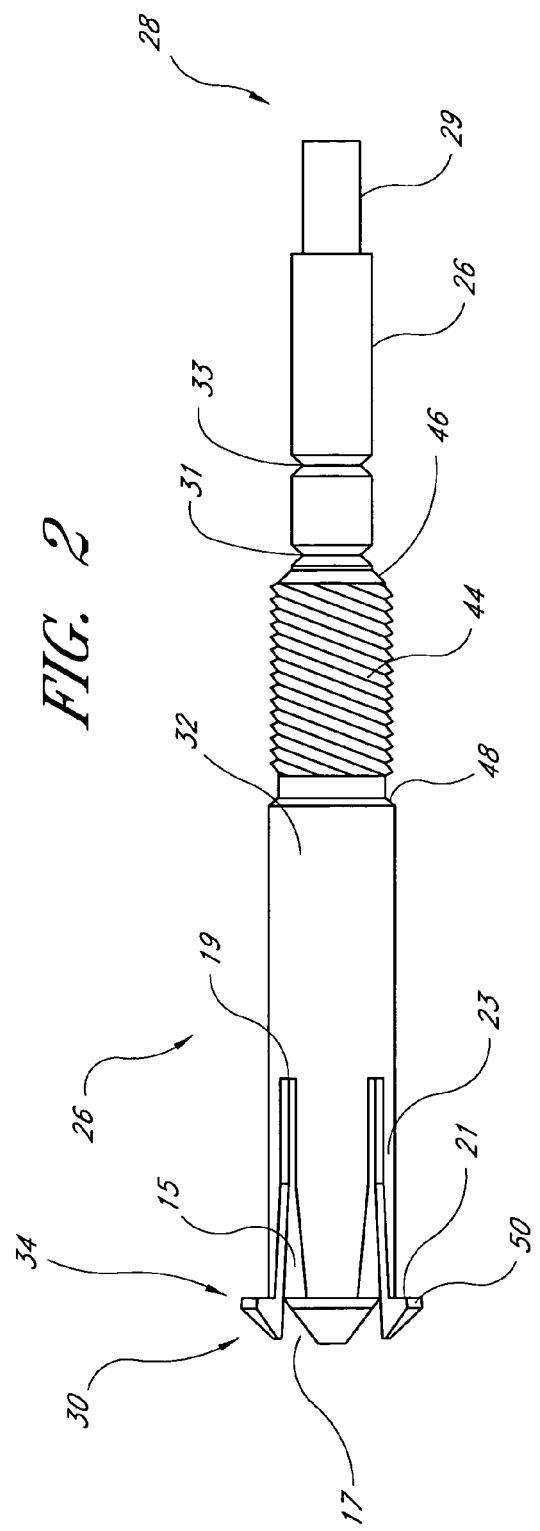
FIG. 2 is a side elevational view of a pin body of the bone fixation device of FIG. 1.
Figure 5:
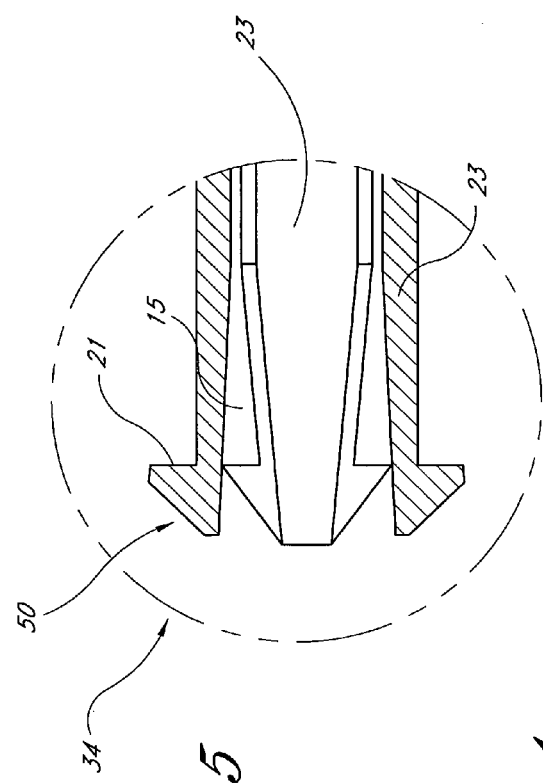
FIG. 5 is an enlarged detail view of the distal end of the device shown in FIG. 2.

One embodiment of the pin 26, adapted for fixing oblique fractures of the fibula or metatarsal bone(s) is illustrated in FIG. 2. The bone fixation device 24 of this embodiment uses a generally cylindrical pin body 32. Although the present invention is disclosed as embodied in a pin body 32 having a generally circular cross section, cross sections such as oval, rectangular, square or tapered to cause radial along with axial bone compression or other configurations may also be used as desired for a particular application.

Pin body 32 generally has an axial length of within the range of from about 5 mm or about 10 mm to about 70 mm in the as-manufactured condition. In one embodiment intended for small bones in the foot, the pin body 32 has an axial length of about 19 mm. The illustrated embodiment shows a cannulated pin body 32, which defines a central lumen 11 to allow introduction of the pin over a wire as is understood in the art. Hollow tubular structures may also be used. However, in other embodiments, a solid pin body may be provided. Such an embodiment is disclosed in co-pending U.S. Pat. No. 6,648,890, filed Apr. 10, 2001, which was incorporated by reference above.

In the illustrated embodiment, the retention structures 44 of the pin 26 comprise a plurality of threads, adapted to cooperate with the complimentary retention structures 42 on the proximal anchor 36, which may be a complimentary plurality of threads. In this embodiment, the proximal anchor 36 may be distally advanced along the pin 26 by rotation of the proximal anchor 36 with respect to the pin 26. Proximal anchor 36 may advantageously be removed from the pin 26 by reverse rotation, such as to permit removal of the pin 26 from the patient. For this purpose, the collar 38 (see FIGS. 6 and 7) is preferably provided with a gripping configuration or structure to permit a removal tool to rotate collar 38 with respect to the pin 26. Any of a variety of gripping surfaces may be provided, such as one or more slots, flats, bores, or the like. In the illustrated embodiment, the collar 38 is provided with a polygonal, and in particular, a hexagonal circumference, as seen in FIG. 7.

Figure 4:
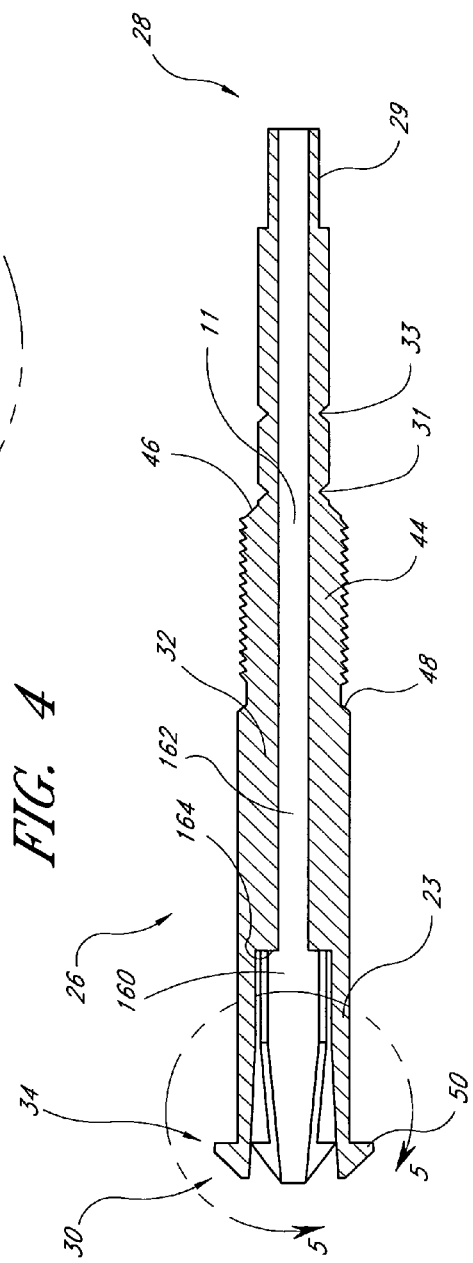
FIG. 4 is a longitudinal cross-sectional view through the pin body of FIG. 2.

The proximal end 28 of the pin 26 is similarly provided with a structure 29 for permitting rotational engagement with an installation or a removal tool. Rotational engagement may be accomplished using any of a variety of shapes or configurations, as will be apparent to those of skill in the art. One convenient structure is to provide the proximal end 26 with one or more flat side walls, for rotationally engaging a complimentary structure on the corresponding tool. As illustrated in FIG. 4, the proximal end 26 may be provided with a structure 29 having a square cross-section. Alternatively, the exterior cross-section through proximal end 28 may be any of a variety of configurations to permit rotational coupling, such as triangular, hexagonal, or other polygons, or one or more axially extending flat sides or channels on an otherwise round body. In still other embodiments, the proximal end 28 of the central lumen 11 may be configured with an non-round cross-section for rotational, engagement with an installation or removal tool.

The retention structures 44 can also comprise a plurality of annular ramp or ratchet-type structures which permit the proximal anchor 36 to be advanced in a distal direction with respect to pin body 32, but which resist proximal motion of proximal anchor 36 with respect to pin body 32. Any of a variety of ratchet-type structures can be utilized in the present invention. Such a ramp or ratchet-type structure provide, among other advantages, the ability of the ratchet to function regardless of the rotational orientation of the proximal anchor 36 with respect to the pin body 32. In an embodiment having a noncircular cross section, or having a rotational link such as an axially-extending spline on the pin body 32 for cooperating with a complementary keyway on proximal anchor 36, the retention structures 42 can be provided on less than the entire circumference of the pin body as will be appreciated by those of skill in the art. Thus, ratchet structures can be aligned in an axial strip such as at the bottom of an axially extending channel in the surface of the pin body.

A single embodiment of the bone fixation device can be used for fixing fractures in bones having any of a variety of diameters. This is accomplished by providing the retention structures 44 over a predetermined axial working length of the pin body 32. For example, in the illustrated embodiment, the retention structures 44 commence at a proximal limit 46 and extend axially until a distal limit 48. Axially extending the retention zone between limits 46 and 48 will extend the effective range of bone thicknesses which the pin 32 can accommodate. Although the retention structures 44 may alternatively be provided throughout the entire length of the pin body 32, retention structures 44 may not be necessary in the most distal portions of pin body 32 in view of the minimum diameter of bones likely to be fixed.

In one embodiment of the invention, the distal limit 48 of retention structures 44 is spaced apart from the distal end 30 of pin body 32 by a distance within the range of from about 4 mm to about 20 mm, and, in embodiments for small bones in the foot, from about 4 mm to about 8 mm. The axial length of the portion of the pin body 32 having retention structures 44 thereon, from proximal limit 46 to distal limit 48, is generally within the range of from about 4 mm to about 8 mm, and was approximately 6 mm in an embodiment having a pin body length of about 19 mm. Depending upon the anchor design, the zone between proximal limit 46 and distal limit 48 may extend at least about 50%, and in some embodiments in excess of about 75% or even in excess of 90% of the length of the pin body.

In general, the minimum diameter of the pin body 32 is a function of the construction material of the pin and the desired tensile strength for a given application. The maximum diameter is established generally by the desire to minimize the diameter of the through hole 22 while still preserving a sufficient structural integrity of the fixation device 24 for the intended application.

The diameter of pin body 32 will generally be in the range of from about 1.5 mm or 1.8 mm for small bones of the foot and hand to as large as 7.0 mm or larger for bones such as the tibia. In one absorbable embodiment of the invention intended for use in the first metatarsal, the pin 24 comprises poly (L, co-D,L-lactide) and has a diameter of about 1.8 mm. Any of a variety of other materials may also be used, as discussed infra.

In a similar manner, the overall length of the tubular housing 40 may be maximized with respect to the depth of the target borehole for a particular application. For example, in a device intended to fix bones having a diameter within the range of from about 15–20 mm, the axial length of the tubular body 40 is preferably at least about 8 mm or 10 mm, and, more preferably, at least about 12 mm or 14 mm. In this manner, the axial length of the zone of retention structures 42 is maximized, thereby increasing the tensile strength of the implanted device. The proximal anchor 36 can be readily constructed using other dimensions and configurations while still accomplishing the desired function, as will be apparent to those of skill in the art in view of the disclosure herein.

The retention structures 42 may comprise any of a variety of complementary surface structures for cooperating with the corresponding structures 44 on the pin 32, as is discussed above. In the illustrated embodiment, the retention structures are in the form of a plurality of annular rings or helical threads, which extend axially throughout the length of the tubular housing 40. The retention structure 42 may alternatively comprise a single thread, ridge or groove or a plurality of structures which extend only part way (e.g., at least about 10% or 25% or more) along the length of the tubular housing 40. Retention force may be optimized by providing threads or other structures along a substantial portion, e.g., throughout at least 75% or 80% of the axial length of the tubular housing 40.

With reference to FIGS. 2–5, the distal anchor 34 in the illustrated embodiment comprises a plurality of ramped extensions or barbs 50 for engaging the distal cortical bone, the interior cancellous bone or other surfaces. As will be explained below, the extensions or barbs 50 are positioned or compressible radially inward for the purpose of advancing the pin 32 into, and, in some applications, through the hole 22. Barbs 50 preferably exert a radially outwardly directed bias so that they tend to extend radially outwardly from the pin body 32 once the distal anchor 34 has advanced out through the distal aperture 20 in bone 10. Proximal traction on the proximal end 28 of pin body 32 will thereafter tend to cause barbs 50 to seat firmly against the outside surface of distal bone component 21, as illustrated in FIG. 1.

The illustrated embodiment includes four barbs 50 (FIG. 3), oriented at 90° with respect to each other. However, anywhere from one to about twelve or more barbs 50 may be utilized as will be apparent to those of skill in the art in view of the disclosure herein. The barbs 50 may be radially symmetrically distributed about the longitudinal axis of the pin 26. Each barb 50 is provided with a transverse engagement surface 21, for contacting the distal surface of the cortical bone or other structure or surface against which the barb 50 is to anchor. Transverse engagement surfaces 21 may lie on a plane which is transverse to the longitudinal axis of the pin 26, or may be inclined with respect to the longitudinal axis of the pin 26.

Each of the transverse engagement surfaces 21 in the illustrated embodiment lies on a common plane which is transverse to the longitudinal axis of the pin 26. Two or more planes containing engagement surfaces 21 may alternatively be provided. The transverse engagement surfaces 21 may also lie on one or more planes which are non-normal to the longitudinal axis of pin 26. For example, the plane of a plurality of transverse engagement surfaces 21 may be inclined at an angle within the range of from about 35° or 45° to about 90° with respect to the longitudinal axis of the pin 26. The plane of the transverse engagement surface may thus be selected to take into account the angle of the distal surface of the bone through which the pin may be positioned, as may be desired in certain clinical applications.

In order to facilitate the radially inward compression of the barbs 50 during the implantation process, followed by radially outward movement of the barbs 50 to engage the distal bone surface, each barb 50 in the illustrated embodiment is carried by a flexible or hinged lever arm 23. Lever arms 23 may be formed by creating a plurality of axial slots 15 in the sidewall of the pin 26. The axial slots 15 cooperate with a central lumen 11 to isolate each barb 50 on a unique lever arm 23. The axial length of the axial slots 15 may be varied, depending upon the desired length over which flexing is desirably distributed, the desired range of lateral motion, and may vary depending upon the desired construction material. For a relatively rigid material such as titanium, axial lengths of the axial slot 15 in excess of about 0.1 inches and preferably in excess of about 0.2 inches are utilized on a pin 26 having an outside diameter of about 0.1 inches and a length of about 1.25 inches. Axial slots 15 will generally extend within a range of from about 5% to about 90%, and often within about 10% to about 30% of the overall length of the pin 26.

The circumferential width of the slots 15 at the distal end 30 is selected to cooperate with the dimensions of the barbs 50 to permit radial inward deflection of each of the barbs 50 so that the pin 26 may be press fit through a predrilled hole having an inside diameter approximately equal to the outside diameter of the pin 26 just proximal to the transverse engagement surfaces 21. For this purpose, each of the slots 15 tapers in circumferential direction width from a relatively larger dimension at the distal end 30 to a relatively smaller dimension at the proximal limit of the axial slot 15. See FIG. 2. In the illustrated embodiment, each slot 15 has a width of about 0.20 inches at the proximal end and a width of about 0.035 inches at the distal end in the unstressed orientation. The width of the slot 15 may taper continuously throughout its length, or, as in the illustrated embodiment, is substantially constant for a proximal section and tapered over a distal section of the slot 15. The wall thickness of the lever arm 23 may also be tapered to increase the diameter of the central lumen 11 in the distal direction. This will allow a lower compressed crossing profile before the inside surfaces of the lever arms bottom out against each other.

Although any of a variety of alternate designs for distal anchor 34 may be utilized in the context of the present invention, any such distal anchors 34 preferably permit axial distal motion of pin body 32, and thereafter resist proximal withdrawal of the pin body 32. As will be appreciated by those of skill in the art, this feature allows the bone fixation device 24 to be set within a bone through a single proximal percutaneous puncture or incision, without the need to expose the distal component 20 or "backside" of the bone. This can be accomplished by biased anchors which are formed integrally with the pin, or which are attached during manufacturing. Distal anchors may also be hinged to the pin body, and may be deployed by a push or pull wire extending through the pin body if the desired construction material does not permit adequate spring bias.

Additional description of the distal anchor and alternate distal anchor designs are described in co-pending U.S. Pat. No. 6,648,890, which is hereby incorporated by reference herein.

For a through hole having a diameter of about 2.3 mm, pin bodies 32 having an outside diameter of about 1.8 mm in the areas other than retention structures 44, and a maximum outside diameter of about 2.24 mm in the area of retention structures 44 have been found to be useful. In this embodiment, the maximum outside diameter of the distal anchor 34 was approximately 2.92 mm in the relaxed state. The axial length from the distal tip of distal end 30 to the proximal extent of extensions 50 was about 1.21 mm.

In use, a bone is first identified having a fracture which is fixable by a pin-type fixation device. The clinician assesses the bone, selects a bone drill and drills a through hole 22 in accordance with conventional techniques.

A bone fixation device 24 having an axial length and outside diameter suitable for the through hole 22 is selected. The distal end 30 of the bone fixation device 24 is percutaneously or otherwise advanced towards the bone, and subsequently advanced through the through hole 22 until distal anchor 34 exits the distal aperture 20. The proximal anchor 36 may be positioned on the bone fixation device 24 prior to positioning of the pin body 32 in the through hole 22, or following placement of the pin body 32 within through hole 22.

The foregoing structures enable the use of an installation and/or deployment tool having a concentric core within a sleeve configuration in which a first component (e.g. a sleeve) engages the proximal anchor 36 and a second component (e.g. a core) engages the proximal rotational engagement structure 29 of pin 26. The first component may be rotated with respect to the second component, so that the proximal anchor 36 may be rotated onto or off of the retention structures 44 on pin 26. In a modified arrangement, a first tool (e.g., a pair of pliers or a wrench) may be used to engage the proximal anchor 36 and a second tool (e.g., a pair of pliers or a wrench) may be used to engage the proximal rotational engagement structure 29 of pin 26. In such an arrangement, the first tool may be rotated with respect to the second tool (or vice versa), so that the proximal anchor 36 may be rotated onto or off the retention structures 44 on the pin 26.

Alternatively, the retention structures 42 on the proximal anchor 36 may be toleranced to permit distal axial advancement onto the pin 26, such as by elastic deformation, but require rotation with respect to the pin 26 in order to remove the proximal anchor 36 from the pin 26.

Following appropriate positioning of the proximal anchor 36, the proximal end 28 of the pin body 32 may be cut off and removed. Pin body 32 may be cut using conventional pin cutters which are routinely available in the clinical setting. Alternatively, a pin may be selected such that it is sized to fit the treatment site such that following tension no proximal extension remains.

Following trimming the proximal end 28 of pin 26, the access site may be closed and dressed in accordance with conventional wound closure techniques.

As mentioned above, in some embodiments, the retention structures 44 on the surface of the pin body comprise a plurality of ratchet-type structures. In such embodiments, proximal traction is preferably applied to the proximal end 28 of pin body 32, to seat the distal anchor 34. While proximal traction is applied to the proximal end 28 of pin body 32, such as by conventional hemostats or a calibrated loading device, the proximal anchor 36 is advanced distally until the anchor 36 fits snugly against the proximal component 19 of the bone. Appropriate tensioning of the bone fixation device 24 is accomplished by tactile feedback or through the use of a calibration device for applying a predetermined load on implantation For any of the ratchet-type embodiments disclosed above, installation can be simplified through the use of an installation tool. The installation tool may comprise a pistol grip or plier-type grip so that the clinician can position the tool at the proximal extension of pin 32 and through one or more contractions with the hand, the proximal anchor 36, 52 and distal anchor 34 can be drawn together to appropriately tension against the bone fragments. The use of a precalibrated tool can permit the application of a predetermined tension in a uniform manner from pin to pin.

Calibration of the installation device to set a predetermined load on the pin can be accomplished through any of a variety of means which will be understood to those of skill in the art. For example, the pin 32 may be provided with one or more score lines or transverse bores or other modifications which limit the tensile strength of the part at one or more predetermined locations. In this manner, axial tension applied to the proximal end 28 with respect to the collar 54 will apply a predetermined load to the bone before the pin 32 will separate at the score line. Alternatively, internal structures within the installation tool can be provided to apply tension up to a predetermined limit and then release tension from the distal end of the tool.

Preferably, the clinician will have access to an array of bone fixation devices 24, having different diameters and axial lengths. These may be packaged one or more per package in sterile envelopes or peelable pouches, or in dispensing cartridges which may each hold a plurality of devices 24. Upon encountering a bone for which the use of a fixation device is deemed appropriate, the clinician will assess the dimensions and load requirements of the bone, and select a bone fixation device from the array which meets the desired specifications.

Any of a variety of alternative retention structures may be configured, to permit removal of the proximal anchor 36 such as following implantation and a bone healing period of time. For example, the retention structures 44 such as threads on the pin 26 may be provided with a plurality of axially extending flats or interruptions, which correspond with a plurality of axial flats on the retention structures 42 of proximal anchor 36. This configuration enables a partial rotation (e.g. 90°) of the proximal anchor 36 with respect to the pin 26, to disengage the corresponding retention structures and permit axial withdrawal of the proximal anchor 36 from the pin 26. One or both of the retention structures 44 and 42 may comprise a helical thread or one or more circumferentially extending ridges or grooves. In a threaded embodiment, the thread may have either a fine pitch or a course pitch. A fine pitch may be selected where a number of rotations of proximal anchor 36 is desired to produce a relatively small axial travel of the anchor 36 with respect to the pin 26. In this configuration, relatively high compressive force may be achieved between the proximal anchor 36 and the distal anchor 34. This configuration will also enable a relatively high resistance to inadvertent reverse rotation of the proximal anchor 36. Alternatively, a relatively course pitch thread such as might be found on a luer connector may be desired for a quick twist connection. In this configuration, a relatively low number of rotations or partial rotation of the proximal anchor 36 will provide a significant axial travel with respect to the pin 26. This configuration may enhance the tactile feedback with respect to the degree of compression placed upon the bone. The thread pitch or other characteristics of the corresponding retention structures can be optimized through routine experimentation by those of skill in art in view of the disclosure herein, taking into account the desired clinical performance.

Referring to FIG. 2, at least a first break point 31 may be provided to facilitate breaking the proximal portion of the pin 26 which projects proximally of the collar 38 following tensioning of the fixation system. Break point 31 in the illustrated embodiment comprises an annular recess or groove, which provides a designed failure point if lateral force is applied to the proximal end 28 while the remainder of the attachment system is relatively securely fixed. At least a second break point 33 may also be provided, depending upon the axial range of travel of the proximal anchor 36 with respect to the pin 26.

In one embodiment having two or more break points 31, 33, the distal break point 31 is provided with one or more perforations or a deeper recess than the proximal break point 33. In this manner, the distal break point 31 will preferentially fail before the proximal break point 33 in response to lateral pressure on the proximal end 28. This will ensure the minimum projection of the pin 26 beyond the collar 38 following deployment and severing of the proximal end 28 as will be appreciated in view of the disclosure herein.

Proximal projection of the proximal end 28 from the proximal anchor 36 following implantation and breaking at a breakpoint 31 may additionally be minimized or eliminated by allowing the breakpoint 31 or 33 to break off within the proximal anchor 36. Referring to FIG. 6, the retention structure 42 may terminate at a point 61 distal to a proximal surface 63 on the anchor 36. An inclined or tapered annular surface 65 increases the inside diameter of the central aperture through proximal anchor 36, in the proximal direction. After the proximal anchor 36 has been distally advanced over a pin 26, such that a breakpoint 31 is positioned between the proximal limit 61 and the proximal surface 63, lateral pressure on the proximal end 28 of pin 26 will allow the breakpoint 31 to break within the area of the inclined surface 65. In this manner, the proximal end of the pin 26 following breaking resides at or distally of the proximal surface 63, thus minimizing the profile of the device and potential tissue irritation.

FIG. 8 illustrates a expansion guide wire 150 that may be used with the fixation device described above. The guide wire has a distal end 152 and a proximal end 154. The illustrated guide wire 150 comprises a locking portion 156 that is located at the distal end 152 of the guide wire 150 and an elongated portion 158 that preferably extends from the distal portion 156 to the proximal end 154 of the guide wire 150. The diameter D1 of the elongated portion 158 is generally smaller than the diameter D2 of the distal portion 154. The guide wire 150 can be made from stainless steel, titanium, or any other suitable material. Preferably, in all metal systems, the guidewire 150 and locking portion 156 are made from the same material as the remainder of the fixation device to prevent cathodic reactions.

The locking portion 156 on guidewire 150 can take any of a variety of forms, and accomplish the intended function as will be apparent to those of skill in the art in view of the disclosure herein. For example, a generally cylindrical locking structure, as illustrated, may be used. Alternatively, any of a variety of other configurations in which the cross section is greater than the cross section of the proximal portion 158 may be used. Conical, spherical, or other shapes may be utilized, depending upon the degree of compression desired and the manner in which the locking portion 156 is designed to interfit with the distal end 30 of the pin.

Figure 9:
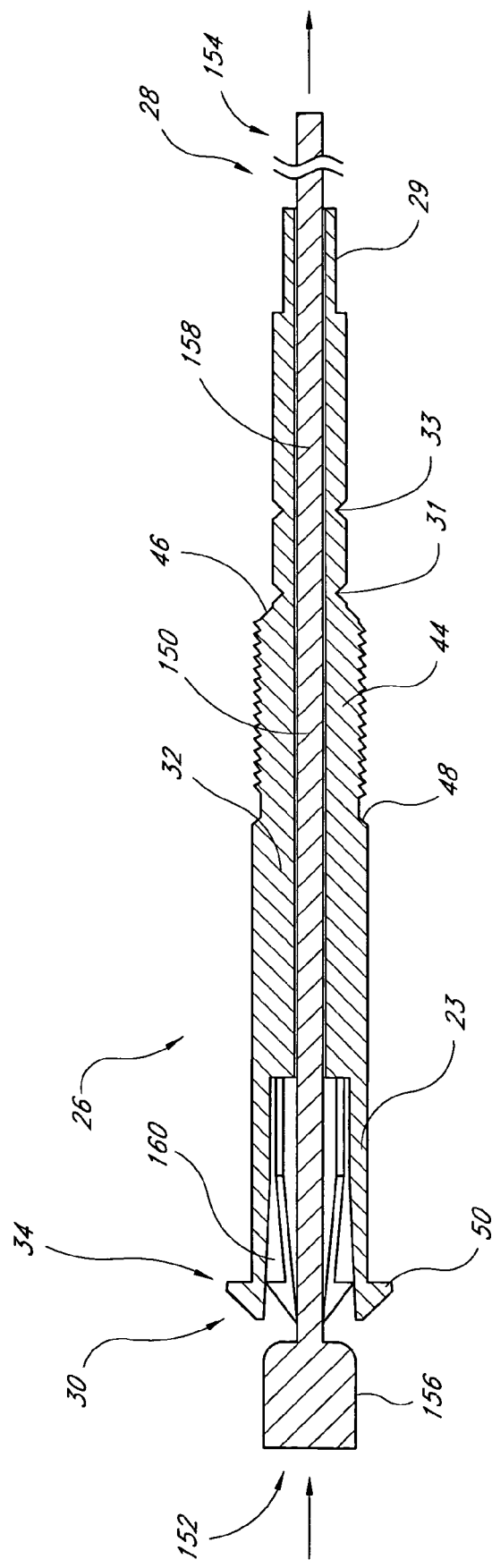
FIG. 9 is a longitudinal cross-sectional view of the locking guide wire of FIG. 8 and the pin body of FIG. 8.
Figure 10A:
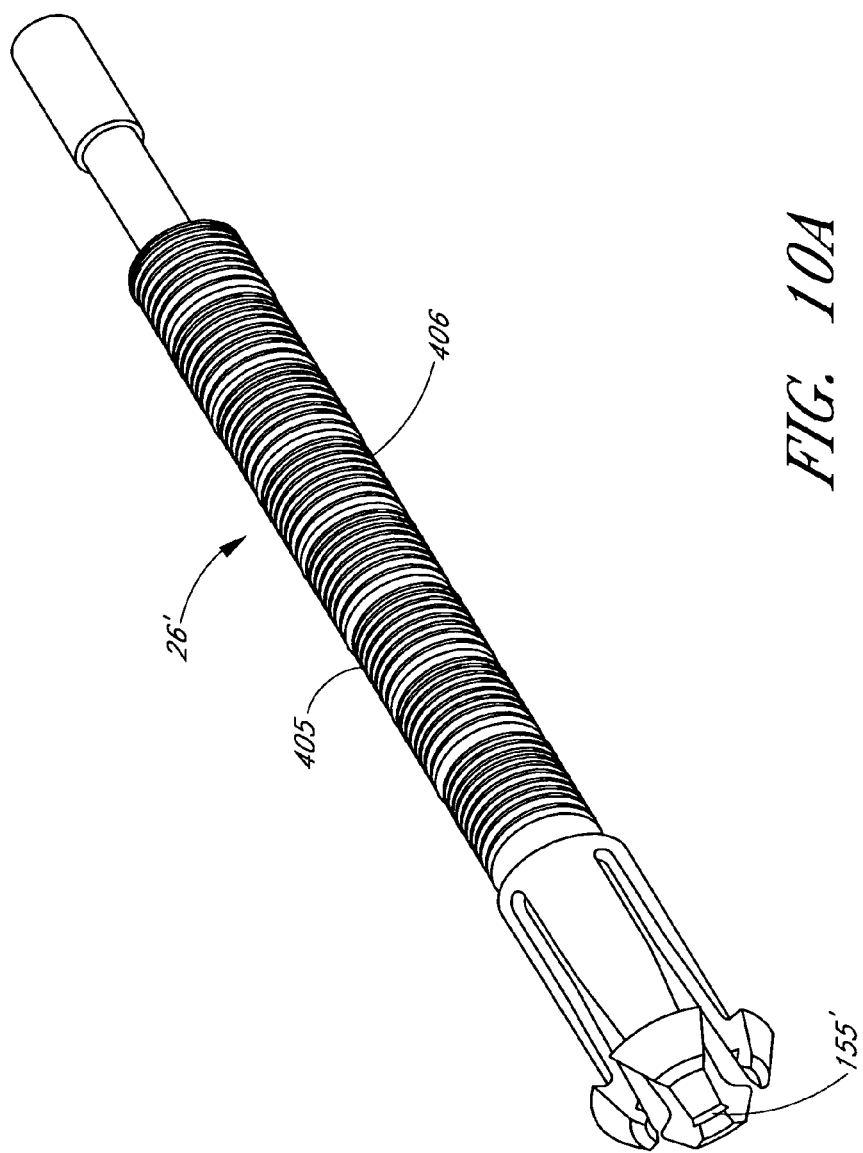
FIGS. 10A–E are perspective, side, top and bottom views of a modified embodiment of a pin body.
Figure 10B:
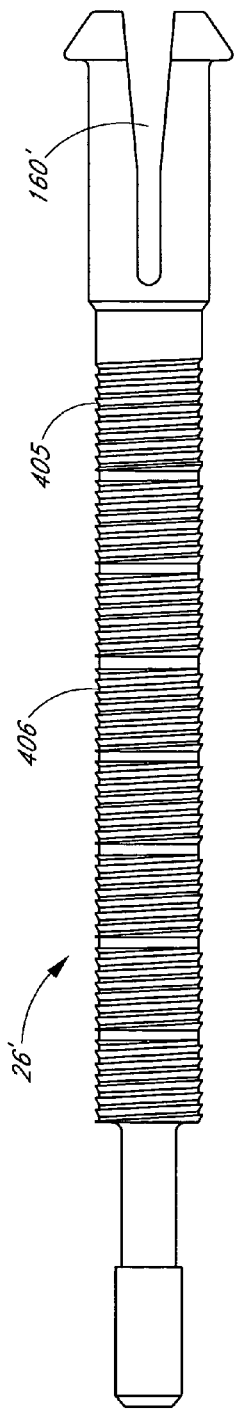
Figure 10C:
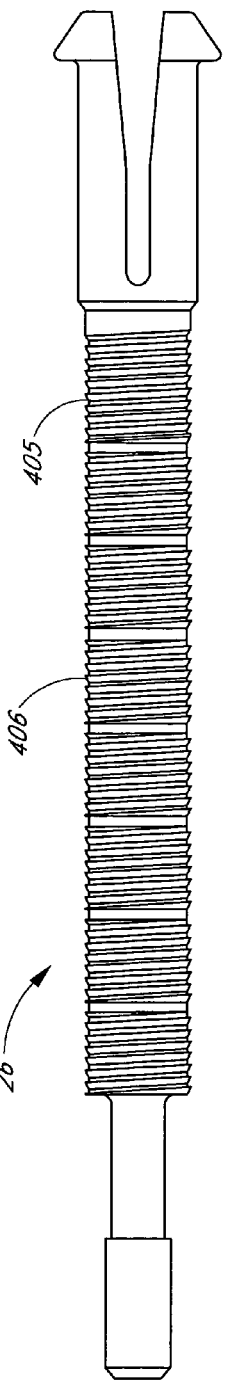
Figure 10D:
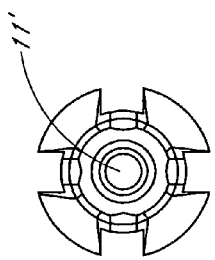
Figure 10E:
Figures 11B, 11C, 11D, 11E:
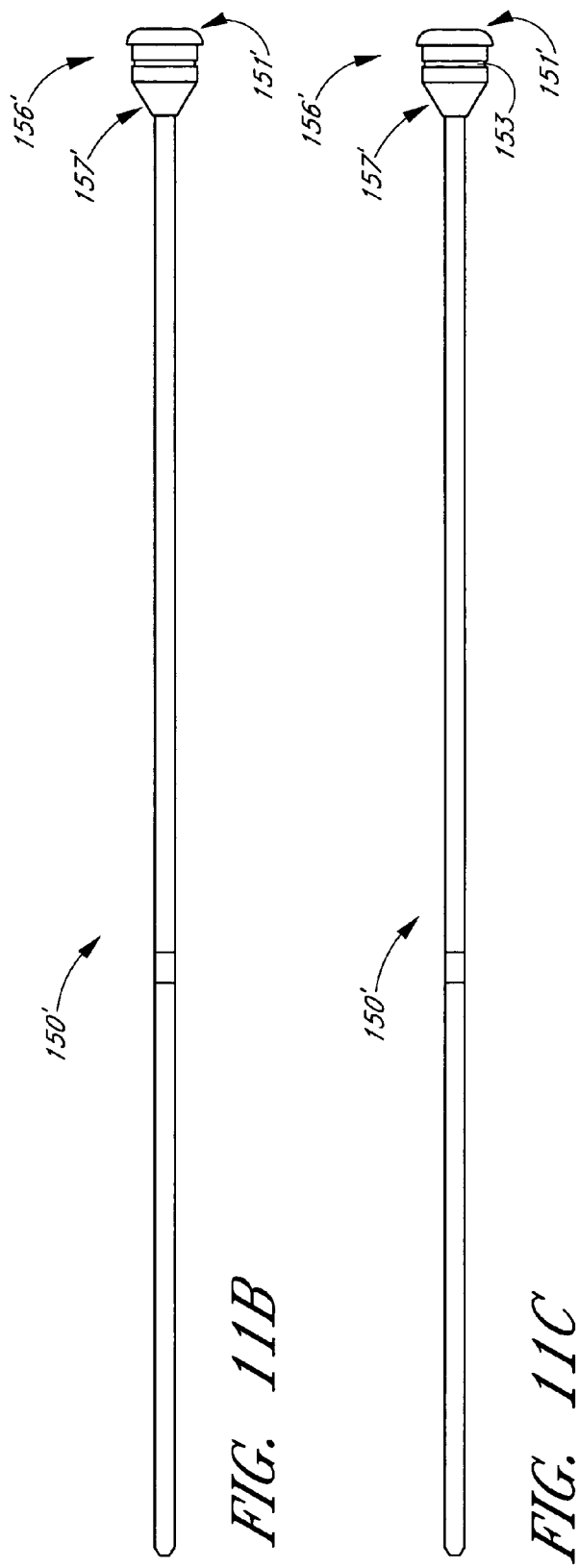
Figure 12B:
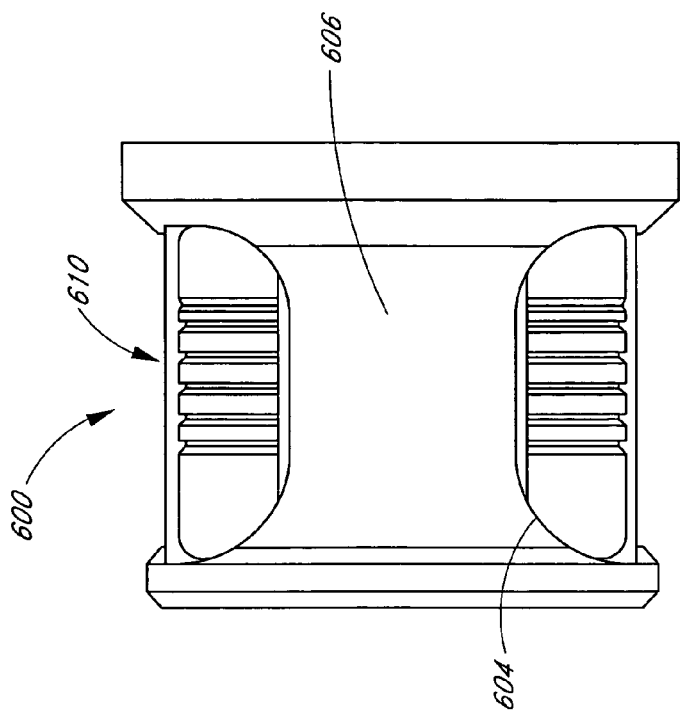
FIGS. 12A–F are perspective, side, top and bottom views of a portion of a modified embodiment of a proximal anchor.
Figure 12A:
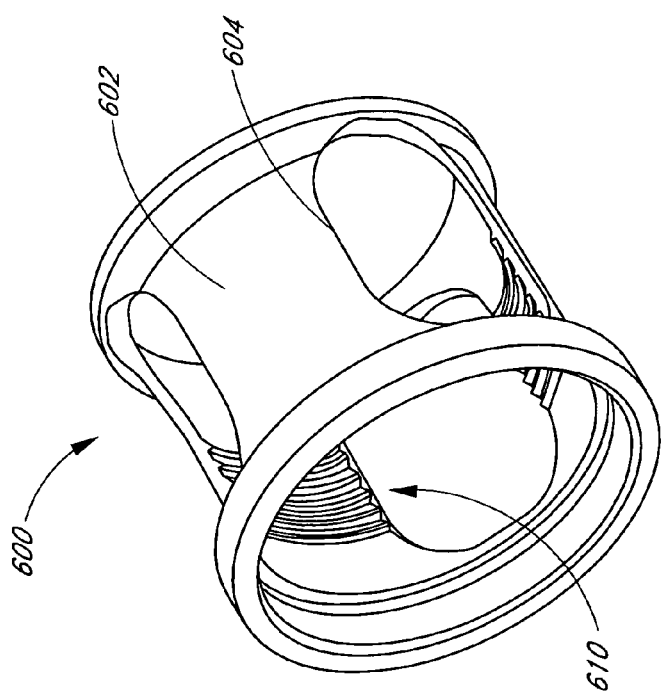
Figure 12F:
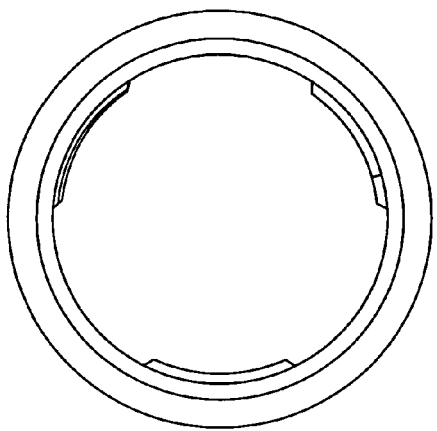
Figure 12D:
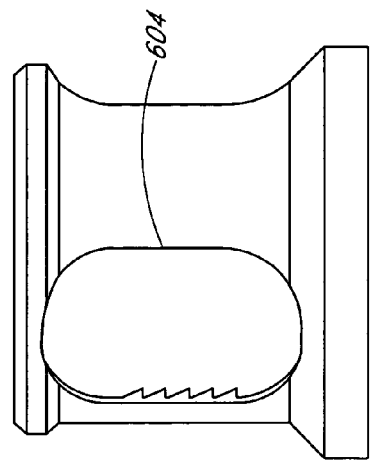
Figure 12E:
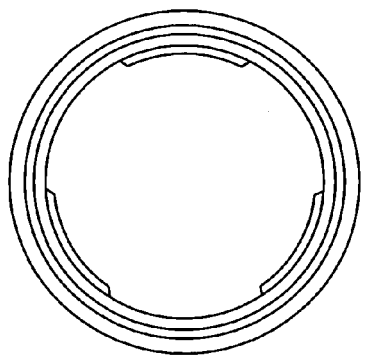
Figure 12C:
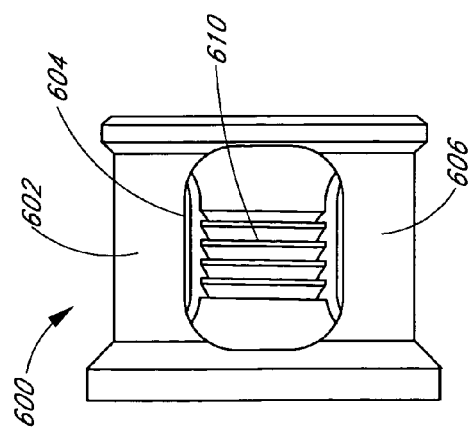
Figure 13A:
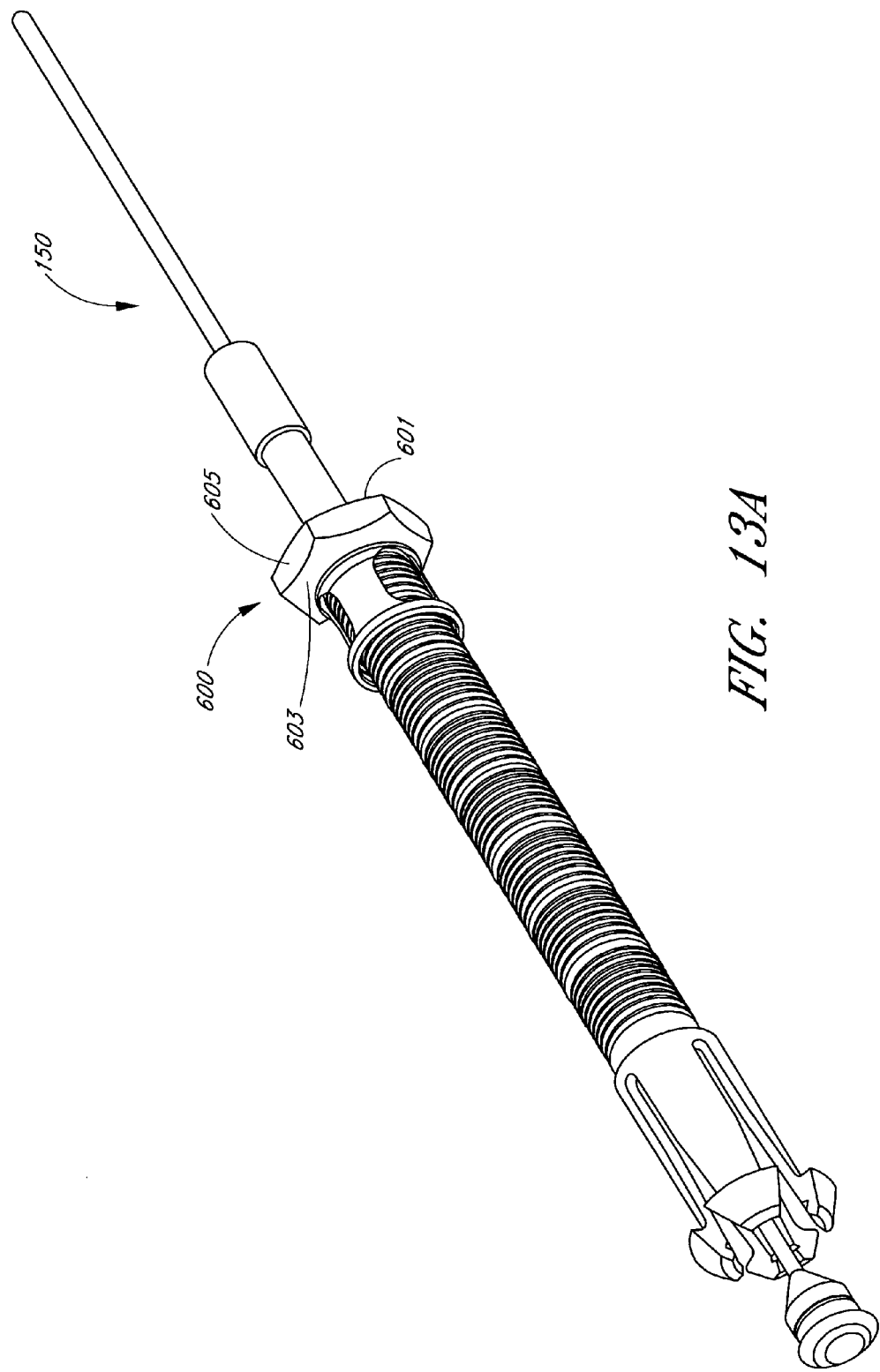

The guide wire 150 is configured such that its proximal end can be threaded through the lumen 11 of the pin 26. With reference to FIG. 9, the lumen 11 preferably comprises a first portion 160 and a second portion 162. The first portion 160 is generally located at the distal end 30 within the region of the lever arms of the pin 26. The second portion 162 preferably extends from the first portion 160 to the proximal end 28 of the pin 26. The inside diameter of the first portion 160 is generally larger than the diameter of the second portion 162. As such, the junction between the first portion 160 and the second portion 162 forms a transverse annular engagement surface 164, which lies transverse to the longitudinal axis of the pin 26.

As mentioned above, the guide wire 150 is configured such that its proximal end can be threaded through the lumen 11 of the pin 26. As such, the diameter D1 of the elongated portion 158 is less than the diameter of the second portion 162 of the lumen 11. In contrast, the diameter D2 of distal portion 156 preferably is slightly smaller than equal to or larger than the diameter of the first portion 160 and larger than the diameter of the second portion 162. This arrangement allows the distal portion 156 to be retracted proximally into the first portion 160 but prevents the distal portion 156 from passing proximally through the pin 26.

In addition, any of a variety of friction enhancing surfaces or surface structures may be provided, to resist distal migration of the locking guidewire 150, post deployment. For example, any of a variety of radially inwardly or radially outwardly directed surface structures may be provided along the length of the locking guidewire 150, to cooperate with a corresponding surface structure on the inside surface of the lumen 11, to removably retain the locking guidewire 150 therein. In one embodiment, a cylindrical groove is provided on the inside surface of the lumen 11 to cooperate with a radially outwardly extending annular flange or ridge on the outside diameter of the locking guidewire 150. The complementary surface structures may be toleranced such that the locking guidewire or guide pin may be proximally retracted into the lumen 11 to engage the locking structure, but the locking structure provides a sufficient resistance to distal migration of the locking guidewire 150 such that it is unlikely or impossible to become disengaged under normal use.

For example, FIGS. 10A–13C illustrate an exemplary embodiment of a locking guidewire 150' and a pin 26' with such radially inwardly and radially outwardly directed surface structures. In this exemplary embodiment, the locking guidewire 150' includes a radially outwardly directed flange 151', which is formed by the locking portion 156' of the guidewire 150'. The flange 151' is configured to allow a portion of the locking portion 156' to be retracted into the first portion 160' of the lumen 11' (see FIGS. 10A–E) while preventing the distal portion 156' from passing proximally through the pin 26' or resisting such movement. To resist distal migration of the locking guidewire 150', the illustrated embodiment includes a radially outwardly directed flange 153', which cooperates with a corresponding cylindrical groove 155' (see FIG. 10A) provided on the inside surface of the lumen 11'. The complementary surface structures 153', 155' may be toleranced such that the locking guidewire 150' may be proximally retracted into the lumen 11' to engage the locking structure, but the locking structure provides a sufficient resistance to distal migration of the locking guidewire 150' such that it is unlikely or impossible to become disengaged under normal use. In addition, the complementary surface structures 153', 155' may be toleranced such that proximally withdrawing the locking guidewire 150' into the lumen 11' produces audible or tactile feedback when the complementary surface structures 153', 155' are properly engaged. Such feedback can be used by the surgeon to indicate that the locking guidewire 150' is properly positioned within the pin 26'. The proximal end of the locking guidewire 150' may also include visual indicia (e.g, color bands, grooves, etc.), which may be referenced with respect the proximal end of the pin to confirm that locking guidewire has been properly retracted. The locking portion 156 on the exemplary pull pin of FIGS. 11A–C also includes a conical or tapered portion 157', which may configured to interact with the lumen of the pin so as to gradually expand the distal end 30' of the pin 26'.

FIGS. 12A–F illustrate a portion of another exemplary embodiment of a proximal anchor. In this embodiment, the proximal anchor 600 includes a tubular housing 602, that may be attached to, coupled to, or integrally formed, partially or wholly, with a flange 601 (see FIGS. 13A–C), which in the illustrated embodiment includes a bone contacting surface 603 and has one or more anti-rotational features 605 (e.g., flat sides). The tubular housing 602 includes an inner surface with one or more teeth or flanges 610, which are configured to engage the grooves or ridges on the body 405. One or more slots or openings 604 are formed in the tubular housing to form one or more bridges 606, which carry the grooves or ridges 605. The anchor 600 can be pushed towards the distal end of the body and the teeth can slide along and be lifted over the retention structures 406 of the body as the bridge is flexed away from the body. The number and shape of the openings and bridges may be varied depending of the desired flexing of the bridges when the proximal anchor is moved distally over the body and the desired retention force of the distal anchor when appropriately tensioned. In one embodiment, the teeth on the proximal anchor and the grooves on the body 405 (FIG. 10A) may be configured such that the proximal anchor can be rotated or threaded onto the pin in the proximal direct and/or so that the proximal anchor can be removed by rotation.

In use, after the clinician assesses the bone, selects a bone drill and drills a through hole 22 (FIG. 1), the distal end 152 of the guide wire 150 and the distal end 30 of the pin 26 are advanced through the through hole until the distal portion 156 and the barbs 50 exit the distal aperture 20. The proximal anchor 36 may be positioned on the bone fixation device 24 prior to positioning of the pin body 32 in the through hole 22, or following placement of the pin body 32 within through hole 22.

Figure 14:
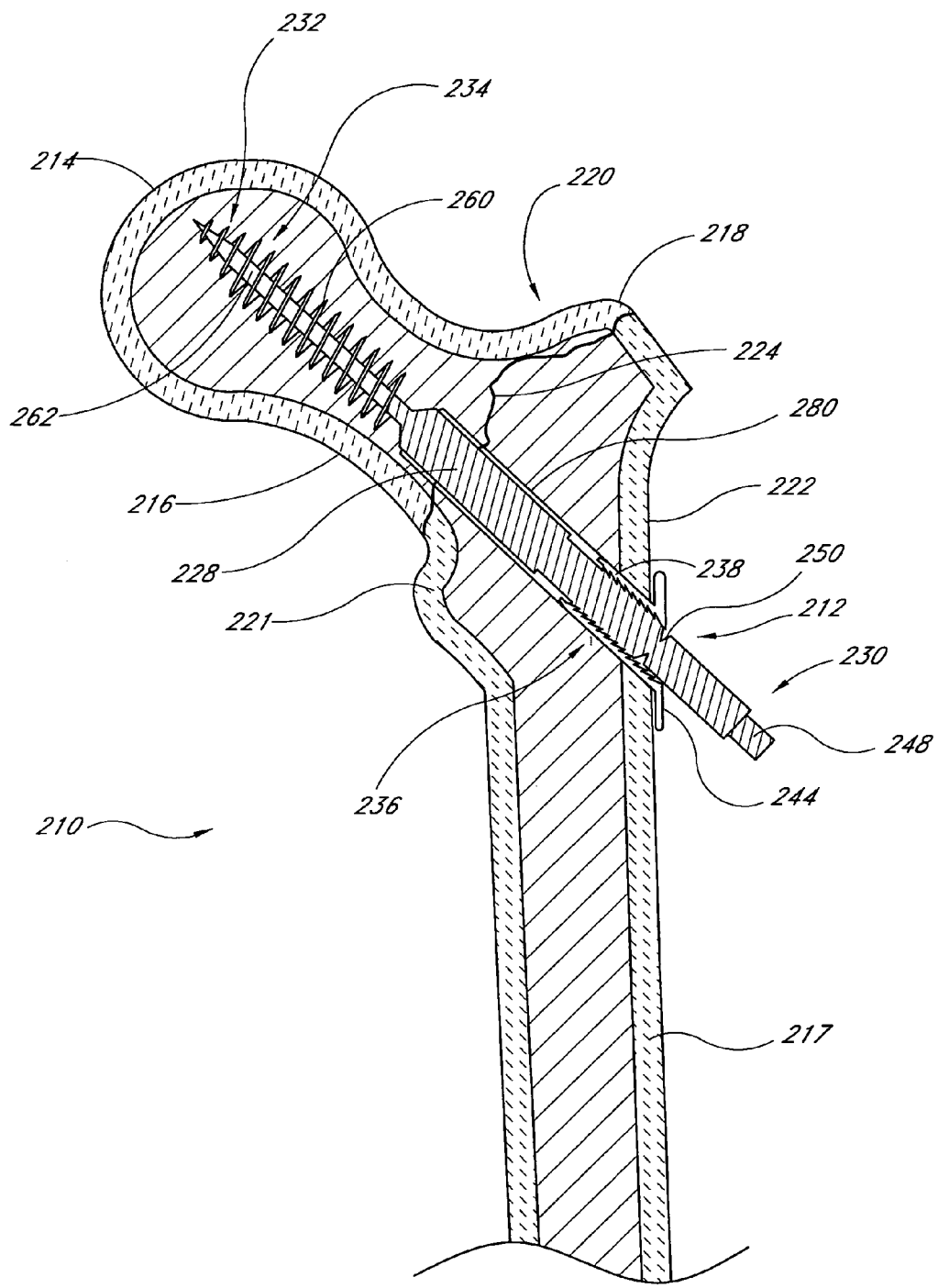
FIG. 14 is a posterior elevational posterior cross section through the proximal portion of the femur, having another embodiment of a bone fixation device positioned therein.

The guide wire 150 is preferably thereafter retracted until the distal portion 156 enters, at least partially, the first portion 160 of the pin 26 (see FIG. 14). The proximal anchor 36 can then be rotated or otherwise distally advanced with respect to the pin body 26 so as to seat the distal anchor 34 snugly against the distal component 21 of the bone. As such, at least a part of the distal portion 156 of the guide wire 150 becomes locked within the first portion 150 of the pin 26. This prevents the barbs 50 and lever arms 24 from being compressed radially inward and ensures that the barbs 50 remain seated snugly against the distal component 21 of the bone.

Following appropriate tensioning of the proximal anchor 36, the proximal end 28 of the pin body 32 and the proximal end 154 of the guide wire 150 are preferably cut off or otherwise removed. These components may be cut using conventional pin cutters which are routinely available in the clinical setting, or snapped off using designed break points as has been discussed. In certain embodiments, the proximal end 28 of the pin body and/or the proximal end 154 of the guidewire 150 may be removed by cauterizing. Cauterizing may fuse the proximal anchor 36 to the body 32 thereby adding to the retention force between the proximal anchor 36 and the body 28. Such fusion between the proximal anchor and the body may be particularly advantageous if the pin and the proximal anchor are made from a bioabsorbable and/or biodegradable material. In this manner, as the material of the proximal anchor and/or the pin is absorbed or degrades, the fusion caused by the cauterizing continues to provide retention force between the proximal anchor and the pin.

Referring to FIG. 14, there is illustrated a posterior side elevational view of the proximal portion of a femur 210, having another embodiment of a fixation device 212 positioned therein. Detailed descriptions of this and alternative fixation devices can be found in co-pending U.S. Pat. No. 6,511,481 issued on Jan. 28, 2003 entitled METHOD AND APPARATUS FOR FIXATION OF PROXIMAL FEMORAL FRACTURE, U.S. patent application Ser. No. 10/012,687 filed on Nov. 13, 2001 entitled DISTAL BONE ANCHORS FOR BONE FIXATION WITH SECONDARY COMPRESSION and U.S. patent application Ser. No. 09/991,367 filed on Nov. 13, 2001 entitled METHOD AND APPARATUS FOR BONE FIXATION WITH SECONDARY COMPRESSION, which are hereby incorporated by reference herein. Although this embodiment of a fixation device is disclosed in the context of fractures of the proximal femur, as with the embodiments described above, the methods and structures disclosed herein are intended for application in any of a wide variety of bones and fractures, as will be apparent to those of skill in the art in view of the disclosure herein.

The proximal end of the femur 210 comprises a head 214 connected by way of a neck 216 to the long body or shaft 217 of the femur 210. As illustrated in FIG. 10, the neck 216 is smaller in diameter than the head 214. The neck 216 and head 214 also lie on an axis which, on average in humans, crosses the longitudinal axis of the body 217 of the femur 210 at an angle of about 126°. The risk of fracture at the neck 216 is thus elevated, among other things, by the angular departure of the neck 216 from the longitudinal axis of the body 217 of femur 210 and also the reduced diameter of the neck 216 with respect to the head 214.

The greater trochanter 218 extends outwardly above the junction of the neck 216 and the body 217 of the femur 210. On the medial side of the greater trochanter 218 is the trochanteric fossa 220. This depression accommodates the insertion of the obturator externus muscle. The lesser trochanter 221 is located posteromedially at the junction of the neck 216 and the body 217 of the femur 210. Both the greater trochanter 218 and the lesser trochanter 221 serve for the attachment of muscles. On the posterior surface of the femur 210 at about the same axial level as the lesser trochanter 221 is the gluteal tuberosity 222, for the insertion of the gluteus maximus muscle. Additional details of the femur are well understood in the art and not discussed in further detail herein.

FIG. 14 illustrates a fracture 224 which crosses the femur approximately in the area of the greater trochanter 218. Fractures of the proximal portion of the femur 210 are generally classified as femoral neck fractures, intertrochanteric fractures and subtrochanteric fractures. All of these fractures will be deemed femoral neck fractures for the purpose of describing the present invention.

Figure 15:
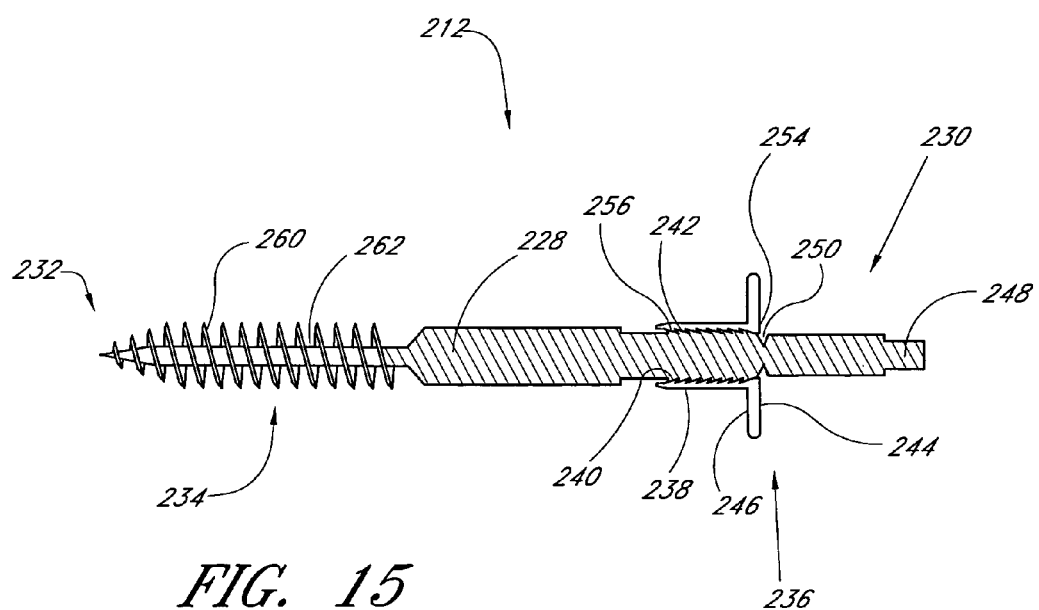
FIG. 15 is a side elevational cross section of a fixation device similar to that of FIG. 14.

Referring to FIGS. 14 and 15, the fixation device 212 comprises a pin body 228 extending between a proximal end 230 and a distal end 232. The length, diameter and construction materials of the body 228 can be varied, depending upon the intended clinical application. In an embodiment optimized for femoral neck fractures in an adult human population, the body 228 will generally be within the range of from about 45 mm to about 120 mm in length after sizing, and within the range of from about 3 mm to about 8 mm in maximum diameter. The major diameter of the helical anchor, discussed below, may be within the range of from about 6 mm to about 12 mm. In general, the appropriate dimensions of the body 228 will vary, depending upon the specific fracture. In rough terms, for a malleolar fracture, shaft diameters in the range of from about 3 mm to about 4.5 mm may be used, and lengths within the range of from about 25 mm to about 70 mm. For condylar fractures, shaft diameters within the range of from about 4 mm to about 6.5 mm may be used with lengths within the range of from about 25 mm to about 70 mm. For colles fractures (distal radius and ulna), diameters within the range of from about 2.5 mm to about 3.5 mm may be used with any of a variety of lengths within the range of from about 6 mm to about 120 mm.

In one embodiment, the body 228 comprises titanium. However, as will be described in more detail below, other metals or bioabsorbable or nonabsorbable polymeric materials may be utilized, depending upon the dimensions and desired structural integrity of the finished fixation device 212.

The distal end 232 of the body 228 is provided with a cancellous bone anchor or distal anchor 234. Additional details of the illustrated cancellous bone anchor and other embodiments are described below and in co-pending U.S. patent application Ser. No. 10/012,687 filed on Nov. 13, 2001 entitled DISTAL BONE ANCHORS FOR BONE FIXATION WITH SECONDARY COMPRESSION, which was incorporated by reference above. In general, the cancellous bone anchor 234 is adapted to be rotationally inserted into the cancellous bone within the head 214 of the femur 210, to retain the fixation device 212 within the femoral head.

The proximal end 230 of the body 228 is provided with a proximal anchor 236. As with the embodiments described with reference to FIGS. 1–9, the proximal anchor 236 is axially distally moveable along the body 228, to permit compression of the fracture 224 as will be apparent from FIG. 14. Complimentary locking structures such as threads or ratchet like structures between the proximal anchor 236 and the body 228 resist proximal movement of the anchor 236 with respect to the body 228 under normal use conditions. The proximal anchor 36 can be axially advanced along the body 228 either with or without rotation, depending upon the complementary locking structures as will be apparent from the disclosure herein.

In the illustrated embodiment, proximal anchor 236 comprises a housing 238 such as a tubular body, for coaxial movement along the body 228. The housing 238 is provided with one or more surface structures 240 such as radially inwardly projecting teeth or flanges, for cooperating with complementary surface structures 242 on the body 228. The surface structures 240 and complementary surface structures 242 permit distal axial travel of the proximal anchor 236 with respect to the body 228, but resist proximal travel of the proximal anchor 236 with respect to the body 228. Any of a variety of complementary surface structures which permit one way ratchet like movement may be utilized, such as a plurality of annular rings or helical threads, ramped ratchet structures and the like for cooperating with an opposing ramped structure or pawl.

Retention structures 242 are spaced axially apart along the body 228, between a proximal limit 254 and a distal limit 256. The axial distance between proximal limit 254 and distal limit 256 is related to the desired axial range of travel of the proximal anchor 236, and thus the range of functional sizes of the fixation device 212. In one embodiment of the fixation device 212, the retention structure 242 comprise a plurality of threads, adapted to cooperate with the retention structures 240 on the proximal anchor 236, which may be a complementary plurality of threads. In this embodiment, the proximal anchor 236 may be distally advanced along the body 228 by rotation of the proximal anchor 236 with respect to the body 228. Proximal anchor 236 may be advantageously removed from the body 28 by reverse rotation, such as to permit removal of the body 28 from the patient. In this embodiment, a washer or flange 244 is preferably provided with a gripping structure to permit a removal tool to rotate the flange 244 with respect to the body 228. Any of a variety of gripping structures may be provided, such as one or more slots, flats, bores or the like. In one embodiment, the flange 244 is provided with a polygonal, and, in particular, a pentagonal or hexagonal circumference.

The flange 244 seats against the outer surface of the femur or tissue adjacent the femur. The flange 244 is preferably an annular flange, to optimize the footprint or contact surface area between the flange 244 and the femur. Circular or polygonal shaped flanges for use in femoral head fixation will generally have a diameter of at least about 4 mm greater than the adjacent body 228 and often within the range of from about 4 mm to about 20 mm or more greater than the adjacent body 228. In a modified embodiment, the flange 244 can be curved to match the curved shape of the femur and further optimize the footprint or contact surface area between the flange 244 and the femur.

Tensioning and release of the proximal anchor 36 may be accomplished in a variety of ways, depending upon the intended installation and removal technique. For example, a simple threaded relationship between the proximal anchor 236 and body 228 enables the proximal anchor 236 to be rotationally tightened as well as removed. However, depending upon the axial length of the threaded portion on the pin 228, an undesirably large amount of time may be required to rotate the proximal anchor 236 into place. For this purpose, the locking structures on the proximal anchor 236 may be adapted to elastically deform or otherwise permit the proximal anchor 236 to be distally advanced along the body 228 without rotation, during the tensioning step. The proximal anchor 236 may be removed by rotation as has been discussed. In addition, any of a variety of quick release and quick engagement structures may be utilized. For example, the threads or other retention structures surrounding the body 228 may be interrupted by two or more opposing flats. Two or more corresponding flats are provided on the interior of the housing 238. By proper rotational alignment of the housing 238 with respect to the body 228, the housing 328 may be easily distally advanced along the body 228 and then locked to the body 228 such as by a 90° or other partial rotation of the housing 238 with respect to the body 228. Other rapid release and rapid engagement structures may also be devised, and still accomplish the advantages of the present invention.

Figure 16:
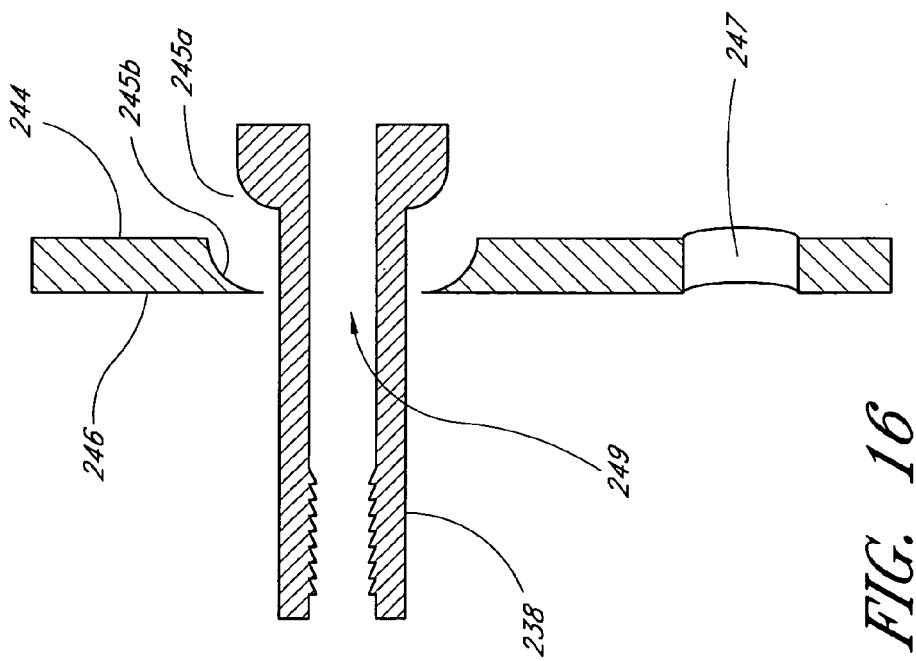
FIG. 16 is a cross sectional view through an angularly adjustable proximal anchor plate.

In the embodiments illustrated in FIGS. 15 and 16, the bone contacting surface 246 of the flange 244 resides in or approximately on a plane which is inclined with respect to the longitudinal axis of the body 228. Any of a variety of angular relationships between the bone contacting surface 246 of the flange 244 and the longitudinal axis of the body 228 and housing 238 may be utilized, depending upon the anticipated entrance angle of the body 228 and associated entrance point surface of the femur 210. In general, the longitudinal axis extending through the head 214 and neck 216 of the human femur is inclined at an angle of approximately 126° from the longitudinal axis of the long body 217 of the femur 210. Angles between the longitudinal axis of body 228 and tissue contacting surface 246 within the range of from about 90° to about 150° will generally be utilized, often within the range of from about 120° to about 150°, for fixed angle fixation devices. Perpendicular flanges (i.e., 90°) are illustrated in FIG. 15.

The clinician can be provided an array of proximal anchors 236 of varying angular relationships between the bone contacting surface 46 and the longitudinal axis of the body 228 and housing 238 (e.g., 90°, 100°, 110°, 120°, and 130°). A single body 228 can be associated with the array such as in a single sterile package. The clinician upon identifying the entrance angle of the body 228 and the associated entrance point surface orientation of the femur 210 can choose the anchor 236 from the array with the best fit angular relationship, for use with the body 228.

Figure 17:
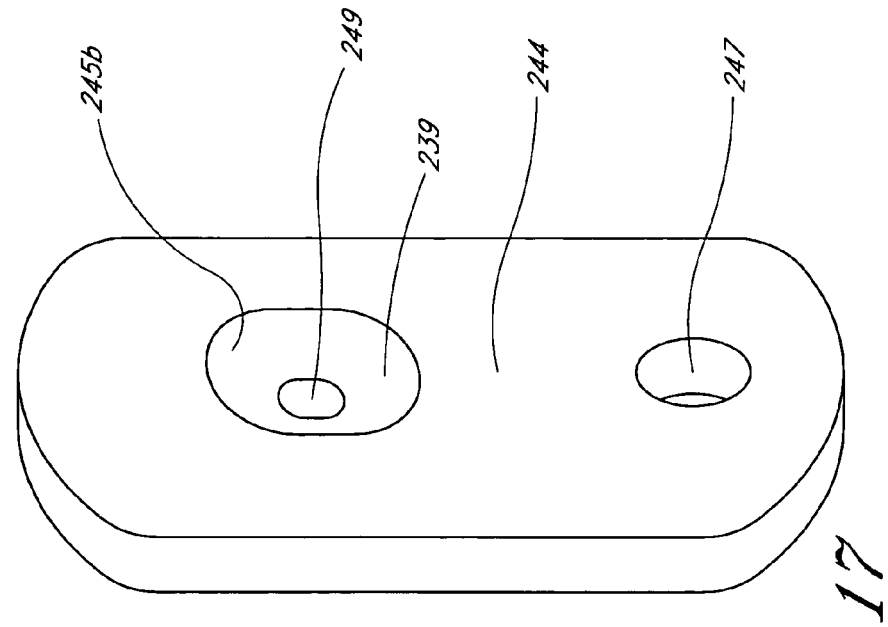
FIG. 17 is a front perspective view of the anchor plate of FIG. 16.

In accordance with an optional feature, illustrated in FIGS. 16 and 17, the flange 244 is angularly adjustable with respect to the longitudinal axis of the body 228. More specifically, in this embodiment, the housing 238 is a separate component from the flange 244. At its proximal end, the housing 238 includes a semi-spherical or radiused surface 245a which forms a part of a head 239. The a semi-spherical or radiused surfaces 245a correspond to corresponding a curved, semi-spherical or radiused surface 245b formed on the flange 244. The surface 245b surrounds an aperture 249 in the flange 244. The aperture 249 is preferably slightly larger than the housing 238 and/or body 228 that extends through the aperture 249 but smaller than the head 239 of the proximal anchor 236. This arrangement allows the housing 238 and/or body 228 to extend through and pivot with respect to the flange 244 while preventing proximal movement of the proximal anchor 236 with respect to the flange 244. As such, the angular relationship between the bone contacting surface 246 of the flange 244 and the longitudinal axis of the body 228 can vary in response to the entrance angle. The flange 244 may optionally include additional apertures 247 for use with one or more fixation screws (not shown) for additional security.

Figure 17A:
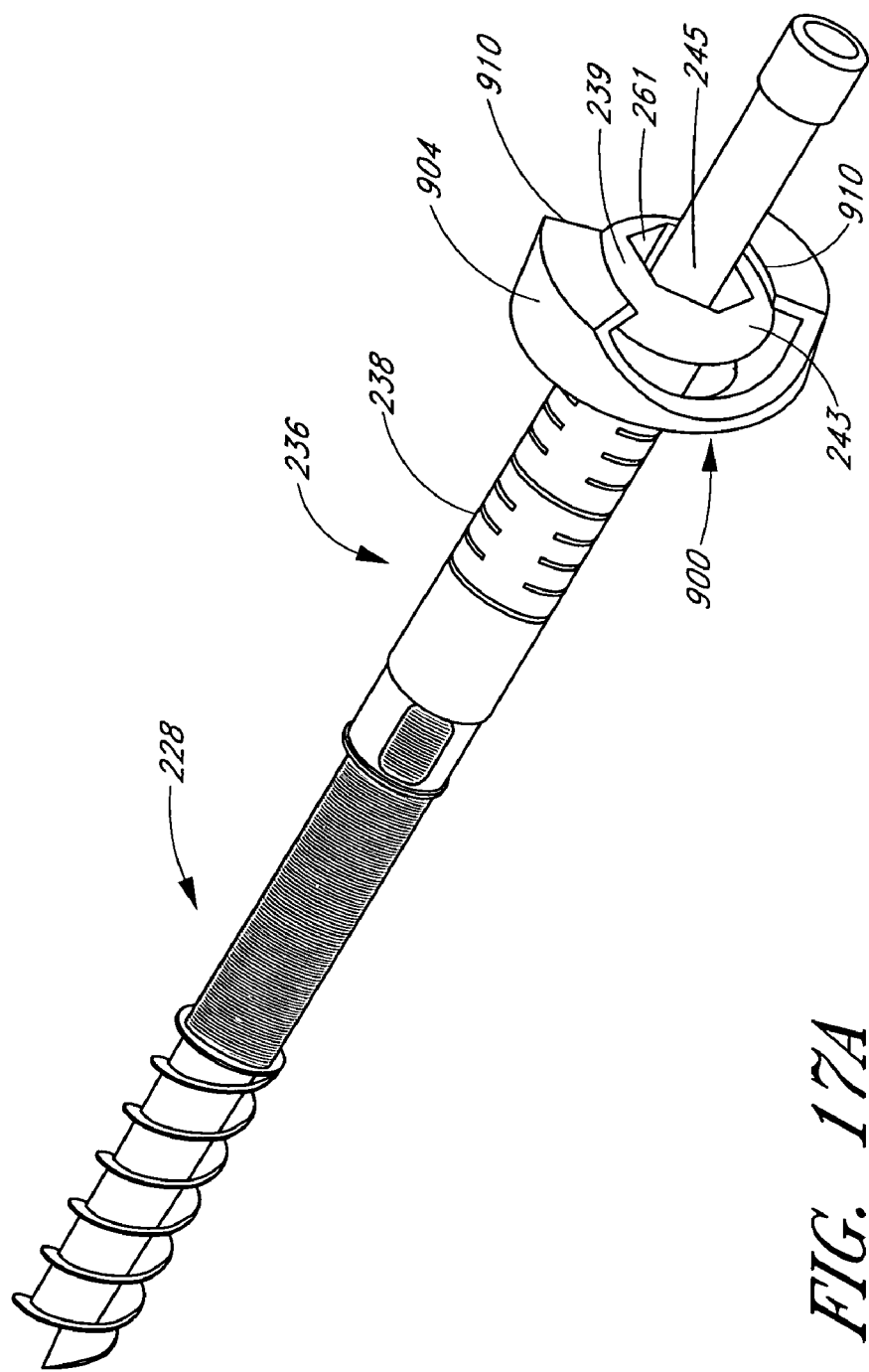
FIG. 17A is a perspective view of a flange and a fixation device.
Figure 17B:
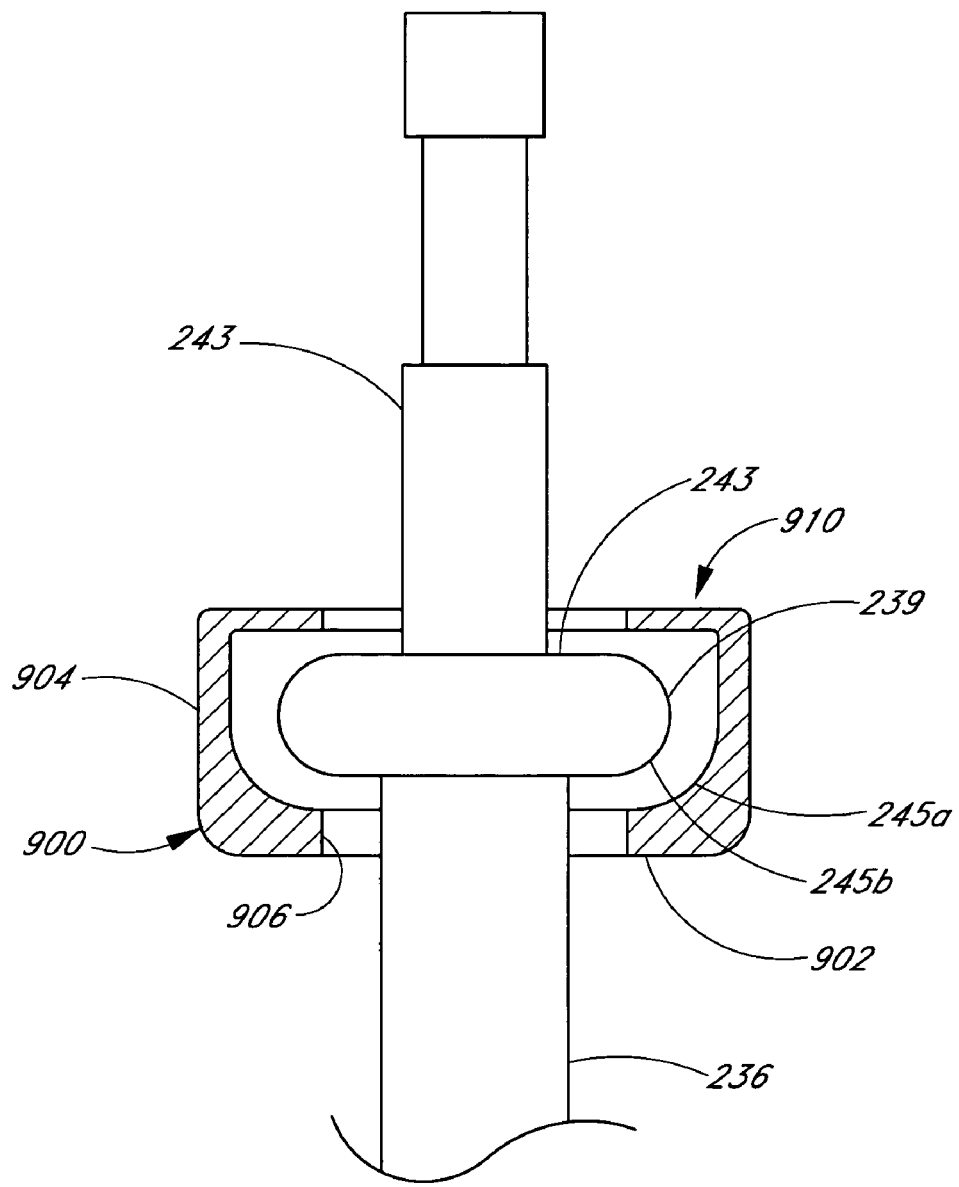
FIG. 17B is a partial cross-sectional side view of the flange of FIG. 17A and a housing of a proximal anchor.
Figure 17C:
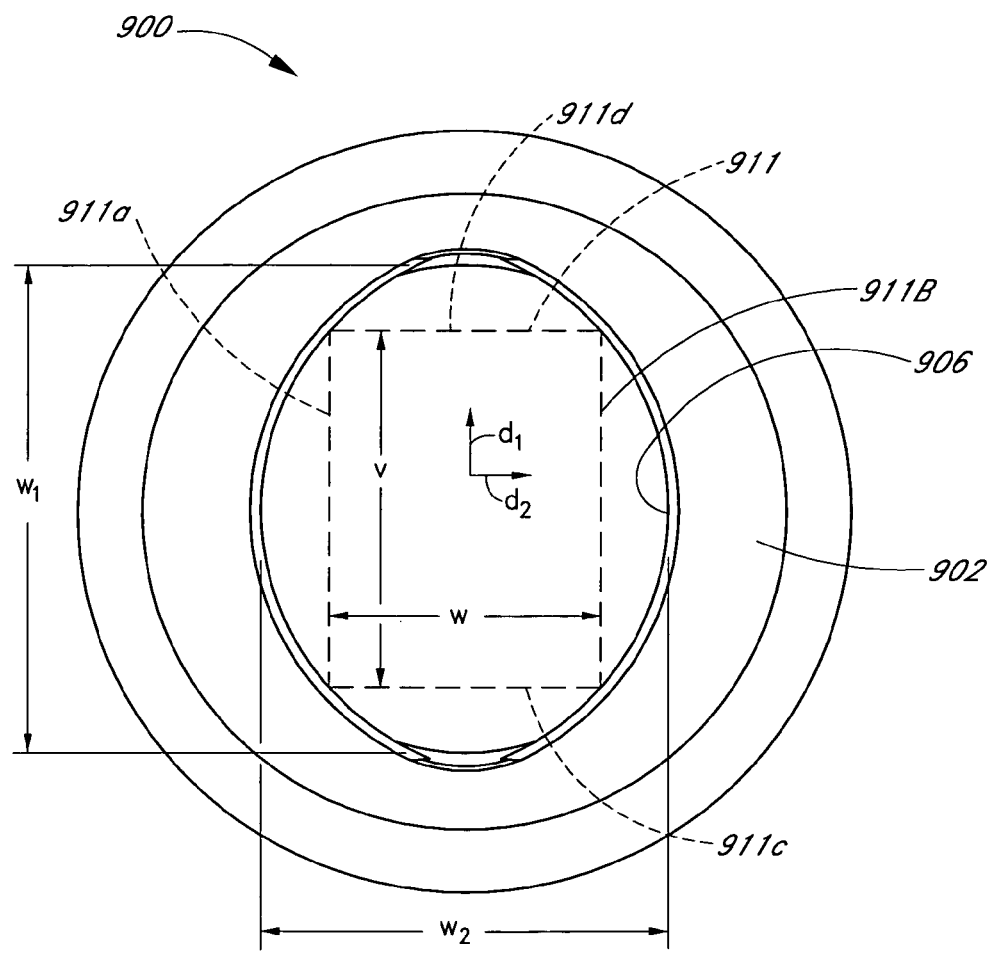
FIG. 17C is a bottom view of the flange of FIG. 17A.

FIGS. 17A–C illustrates a modified embodiment of a flange or washer 900. As with the flange 244 of FIG. 16, the washer 900 is configured to interact with the head 239 of the proximal anchor 236. The washer 900 includes a base 902 and a side wall 904. The base 902 and side wall 904 define a curved, semi-spherical or radiused surface 245a that interacts with the corresponding curved, semi-spherical or radiused surface 245b of the head 239. The surface 245a surrounds an aperture 906 formed in the base 902. As described above, this arrangement allows the housing 238 and/or body 228 to extend through and pivot with respect to the washer 900.

With particular reference to FIG. 17C, in the illustrated embodiment, the aperture 906 is elongated with respect to a first direction d1 as compared a second direction d2, which is generally perpendicular to the first direction d1. In this manner, the width w1 of the aperture in the first direction is greater than the width w2 of the aperture in the second direction. In this manner, the aperture 906 provides a channel 911 with a width w between the sides 911a, 911b defined with respect to the second direction d2 that is preferably greater than the maximum width of the tubular housing 238 but smaller than the width of the head 908 such that the proximal anchor 236 can not be pulled through the aperture 906. The height h of the channel is defined between the sides 911c, 911d in the second direction. As such, the elongated aperture 906 permits greater angular movement in a plane containing the first direction d1 as portions of the proximal anchor 236 are allowed rotate into the elongated portions of the aperture 906. The aperture 906 may be elliptical or formed into other shapes, such as, for example, a rectangle or a combination of straight and curved sides.

The washer 900 optionally includes a portion that is configured so that the proximal end 243 of the anchor 236 is retained, preferably permanently retained, within the washer 900. In the illustrated embodiment, the side walls 904 are provided with lips 910. The lips 910 extend inwardly from the side walls 904 towards the aperture 906 and interact with the proximal end 243 of the head 239 so that the proximal anchor 236 is retained within the washer 900. Preferably, the washer 900 is toleranced to allow the proximal anchor 236 to freely rotate with respect to the washer 900. In this manner, the washer 900 and the proximal anchor 236 can move together for convenient transport.

As described above, when the body 228, the proximal anchor 236 and the washer 900 are deployed into a patient, the washer 900 can inhibit distal movement of the body 228 while permitting at least limited rotation between the body 228 and the washer 900. As such, the illustrated arrangement allows for rotational and angular movement of the washer 900 with respect to the body 228 to accommodate variable anatomical angles of the bone surface. This embodiment is particularly advantageous for spinal fixation and, in particular, trans-laminar, trans-facet and trans-facet-pedicle applications. In such applications, the washer 900 may seat directly against the outer surface of a vertebra. Because the outer surface of the vertebra is typically non-planar and/or the angle of insertion is not perpendicular to the outer surface of the vertebra, a fixed flange may contact only a portion of the outer surface of the vertebra. This may cause the vertebra to crack due to high stress concentrations. In contrast, the angularly adjustable washer 900 can rotate with respect to the body and thereby the bone contacting surface may be positioned more closely to the outer surface. More bone contacting surface is thereby utilized and the stress is spread out over a larger area. In addition, the washer, which has a larger diameter than the body 228, or proximal anchor described herein, effectively increases the shaft to head diameter of the fixation device, thereby increasing the size of the loading surface and reducing stress concentrations. Additionally, the washer 900 can be self aligning with the outer surface of the vertebra, which may be curved or non-planer. The washer 900 can slide along the surface of the vertebra and freely rotate about the body 228 until the washer 900 rests snugly against the surface of the vertebra for an increased contact area between the bone and the washer 900. As such, the washer 900 can be conveniently aligned with a curved surface of the vertebra.

In another embodiment, the washer 900 has a surface treatment or bone engagement features that can engage with the surface of the bone to inhibit relative movement between the washer 900 and the bone. Although not illustrated, the washer 900 can include a plurality of bone engagement features in the form of one or more spikes (not shown) extending from the surface of the washer 900. The spikes can contact the surface of the bone to provide additional gripping support, especially when the flange 244 is positioned against, for example, uneven bone surfaces and/or soft tissue. Optionally, the washer 900 can have protuberances, roughened surface, ridges, serrations, or other surface treatment for providing friction between the flange 244 and the surface of the bone. However, it should be appreciated that in modified embodiments the washer 900 may be formed without the bone engagement features or surface treatments. As an independent feature, for example, the washer 900 can be enlarged and includes one or two or more openings for receiving one or set screws (not shown). The setscrews can be passed through the openings to securely fasten the washer 900 to a bone.

With reference back to FIGS. 14 and 15, the proximal end 230 of the body 228 is preferably additionally provided with rotational coupling 248, for allowing the body 228 to be rotationally coupled to a driving device. Any of a variety of driving devices may be utilized, such as electric drills or hand tools which allow the clinician to manually rotate the cancellous bone anchor 234 into the head of the femur. Thus, the rotational coupling 248 may have any of a variety of cross sectional configurations, such as one or more flats or splines.

In one embodiment, the rotational coupling 248 comprises a proximal projection of the body 228 having a polygonal cross section, such as a hexagonal cross section. The rotational coupling 248 is illustrated as a male component, machined or milled or attached to the proximal end 230 of the body 228. However, the rotational coupling may also be in the form of a female element, such as a hexagonal or other noncircular cross sectioned lumen extending throughout a proximal portion or the entire length of the body 228. Although illustrated as solid throughout, the body 228 may be cannulated to accommodate installation over a placement wire as is understood in the art. The cross section of the central cannulation can be made non circular, e.g., hexagonal, to accommodate a corresponding male tool for installation or removal of the device regardless of the location of the proximal break point.

The body 228 may be provided with at least one and preferably two or three or more break points 250 spaced axially apart along the proximal portion of the body 228. Break points 250 comprise a weakened transverse plane through the body 228, which facilitate severing of the proximal portion of the body 228 following proper tensioning of the proximal anchor. Break point 250 may be constructed in any of a variety of ways, such as by machining or milling an annular recess into the exterior wall of the body 228, or created one or more transverse perforations through the body 228 such as by mechanical, laser, or EDM drilling.

In one embodiment, the distal anchor 234 comprises a helical locking structure 260 for engaging cancellous bone, as illustrated in FIG. 14. The locking structure 260, such as a flange, may either be wrapped around a central core 262 or an axial lumen, as discussed below. The flange extends through at least one and generally from about two to about 250 or more full revolutions depending upon the axial length of the distal anchor and intended application. For most femoral neck fixation devices, the flange will generally complete from about 2 to about 20 revolutions. The helical flange 260 is preferably provided with a pitch and an axial spacing to optimize the retention force within cancellous bone, to optimize compression of the fracture. In some applications, it may advantageous for the distal anchor to engage cortical bone. In such applications, the pitch and axial spacing may be optimized for cortical bone.

The helical flange 260 of the embodiment illustrated in FIG. 14 is shaped generally like a flat blade or radially extended screw thread. However, it should be appreciated that the helical flange 260 can have any of a variety of cross sectional shapes, such as rectangular, triangular or other as deemed desirable for a particular application through routine experimentation in view of the disclosure herein. The outer edge of the helical flange 260 defines an outer boundary. The ratio of the diameter of the outer boundary to the diameter of the central core 262 can be optimized with respect to the desired retention force within the cancellous bone and giving due consideration to the structural integrity and strength of the distal anchor 234. Another aspect of the distal anchor 234 that can be optimized is the shape of the outer boundary and the central core 262, which in the illustrated embodiment are generally cylindrical with a tapered distal end 232.

The distal end 232 and/or the outer edges of the helical flange 260 may be atraumatic (e.g., blunt or soft). This inhibits the tendency of the fixation device 212 to migrate anatomically proximally towards the hip joint bearing surface after implantation (i.e., femoral head cut-out). Distal migration is also inhibited by the dimensions and presence of the proximal anchor 236, which has a larger footprint than conventional screws.

Figure 18:
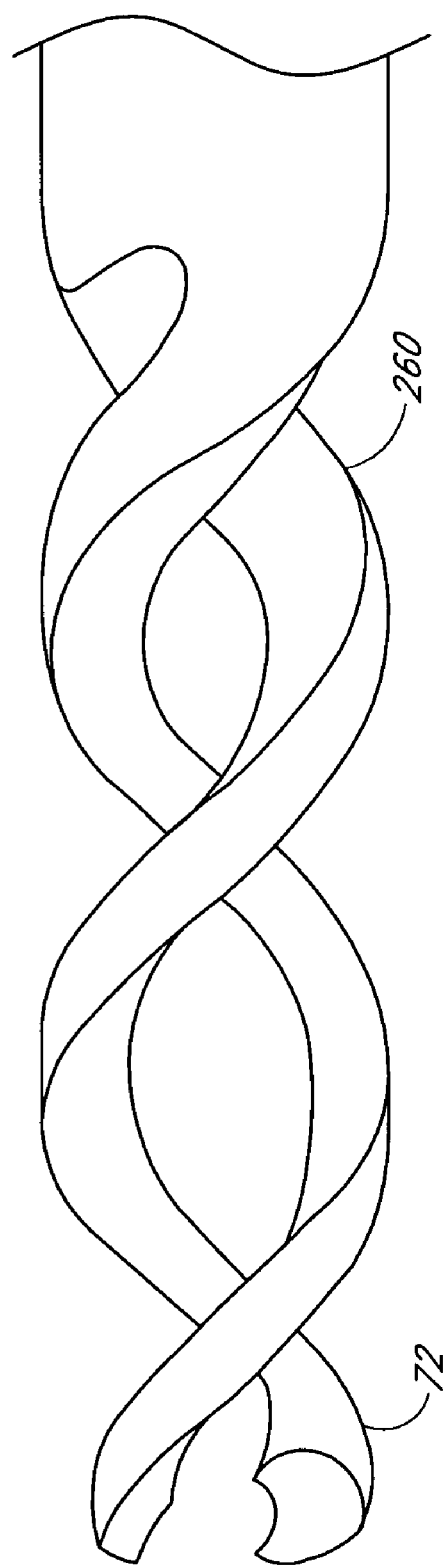
FIG. 18 is a side elevational view of a double helix distal anchor.

Referring to FIG. 18, a variation of the distal anchor 234 is illustrated. In this embodiment, the distal anchor comprises a double helix structure. Each helix is spirally wrapped about an imaginary cylinder through at least one and preferably from about 2 to about 20 or more full revolutions per inch. In a modified embodiment, each helix is wrapped around substantially cylindrical central core that includes a central lumen that also extends through the body. As with the previous embodiment, the helix structure is preferably provided with pitch and an axial spacing to optimize the retention force within cancellous bone, which optimizes compression. The tip 72 of the elongated body 260 may be pointed or sharp. In one preferred embodiment, the each helix has wrapped about 7 revolutions per each for an overall thread density of about 14 revolutions per inch.

In any of the embodiments herein, an antirotation lock may be provided between the distal anchor and the proximal collar or plate, such as a spline or other interfit structure to prevent relative rotation of the proximal and distal ends of the device following implantation.

In use, the clinician first identifies a patient having a fracture such as, for example, a femoral neck fracture, which is fixable by an internal fixation device. The clinician accesses the proximal femur, reduces the fracture if necessary and selects a bone drill and drills a hole 280 (FIG. 14) in accordance with conventional techniques. Preferably, the hole 280 has a diameter within the range from about 3 mm to about 8 mm. This diameter may be slightly larger than the diameter of the distal anchor 234. The hole 280 preferably extends up to or slightly beyond the fracture 224. In certain embodiments, the clinician may use a bone drill with a counter sink(s) configured for providing a larger diameter recesses for the housing 238 and/or the flange 244 of the proximal anchor 236.

A fixation device 212 having an axial length and outside diameter suitable for the through hole 280 is selected. The distal end 232 of the fixation device 212 is advanced distally into the hole 280 until the distal anchor 234 reaches the distal end of the hole 280. The proximal anchor 236 may be carried by the fixation device 212 prior to advancing the body 228 into the hole 280, or may be attached following placement of the body 228 within the hole 280. Once the body 228 is in place, the clinician may use any of a variety of driving devices, such as electric drills or hand tools to rotate the cancellous bone anchor 234 into the head of the femur.

While proximal traction is applied to the proximal end 230 of body 228, such as by conventional hemostats, pliers or a calibrated loading device, the proximal anchor 236 is advanced distally until the anchor 236 fits snugly against the outer surface of the femur or tissue adjacent the femur. Appropriate tensioning of the fixation device 212 is accomplished by tactile feedback or through the use of a calibration device for applying a predetermined load on the implantation device. One advantage of the structure of the present invention is the ability to adjust compression independently of the setting of the distal anchor 234.

Following appropriate tensioning of the proximal anchor 236, the proximal extension 230 of the body 228 is preferably cut off or snapped off and removed. Body 228 may be cut using conventional saws, cutters or bone forceps which are routinely available in the clinical setting. Alternatively, the fixation device can be selected such that it is sized to length upon tensioning, so no proximal projection remains. In certain embodiments, the proximal extension 230 of the body 228 may be removed by cauterizing. Cauterizing the proximal extension 230 may advantageously fuse the proximal anchor 235 to the body 228 thereby adding to the retention force between the proximal anchor 235 and the body 228. Such fusion between the proximal anchor 235 and the body 228 may be particularly advantageous if the pin 228 and the proximal anchor are made from a bioabsorbable and/or biodegradable material. In this manner, as the material of the proximal anchor and/or the pin is absorbed or degrades, the fusion caused by the cauterizing continues to provide retention force between the proximal anchor and the pin.

Following trimming the proximal end 230 of body 228, the access site may be closed and dressed in accordance with conventional wound closure techniques.

Figure 19:
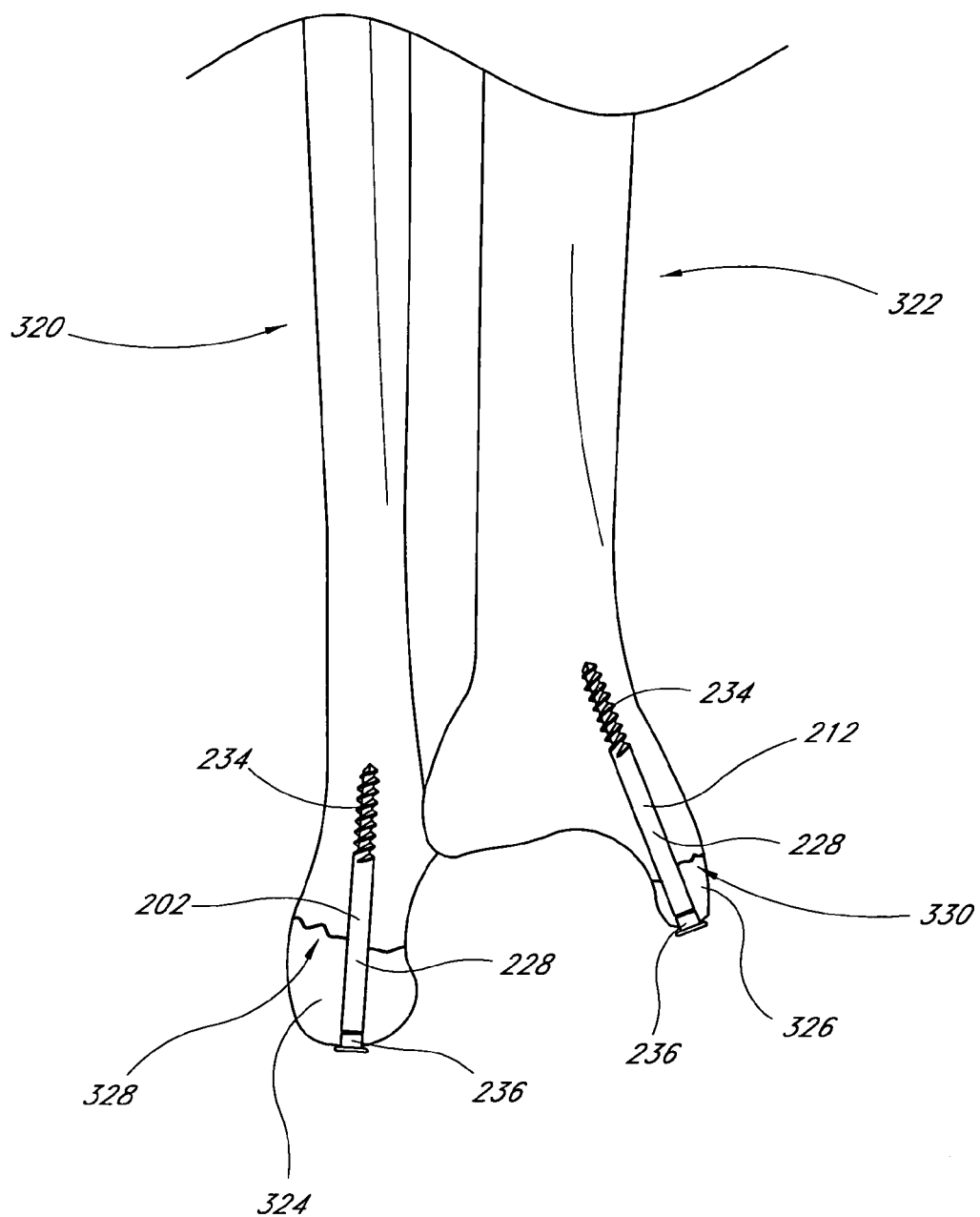
FIG. 19 is an anterior view of the distal tibia and fibula, with fixation devices across lateral and medial malleolar fractures.

FIG. 19 also illustrates a fixation device 212 extending through the medial malleolus 326, across a medial malleolar fracture 330, and into the tibia 322. Although FIG. 19 illustrates fixation of both a lateral malleolar fracture 328 and medial malleolar fracture 130, either fracture can occur without the other as is well understood in the art. Installation of the fixation devices across malleolar fractures is accomplished utilizing the same basic steps discussed above in connection with the fixation of femoral neck fractures FIGS. 20–23 illustrate a modified embodiment of a proximal anchor 400, which can be used with the bone fixation devices described above.

Figure 20:
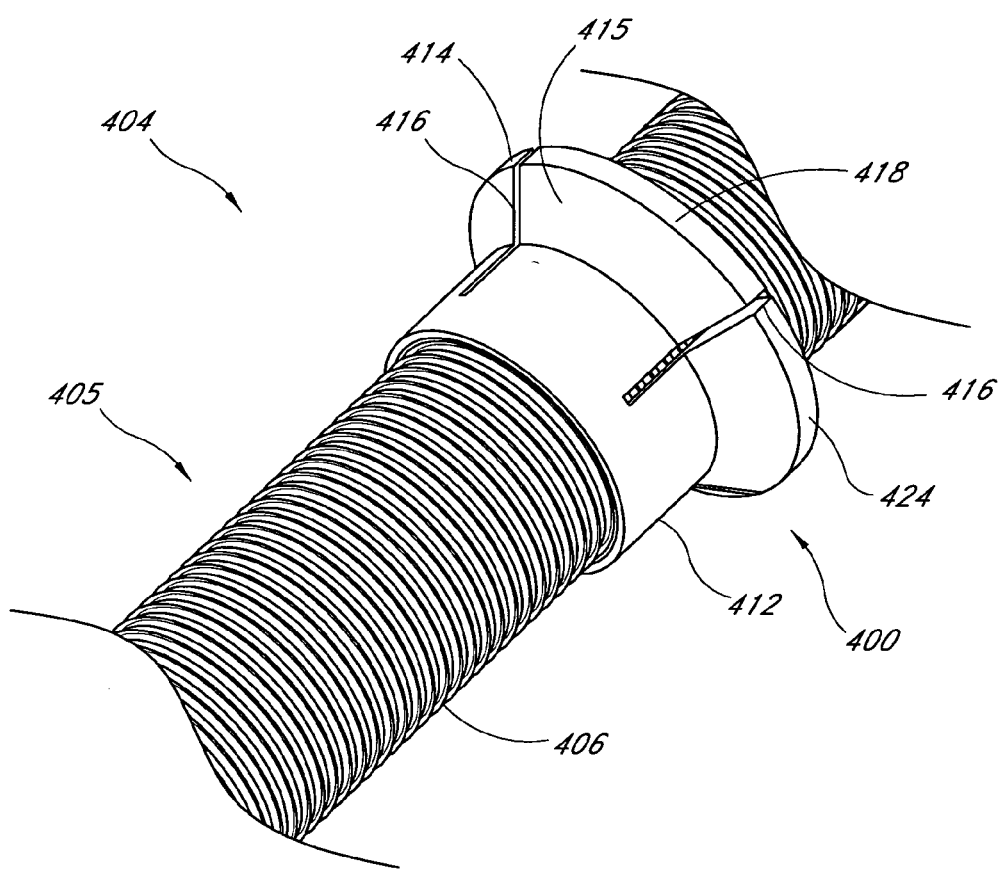
FIG. 20 is a perspective view of another embodiment of a proximal anchor.
Figure 21:
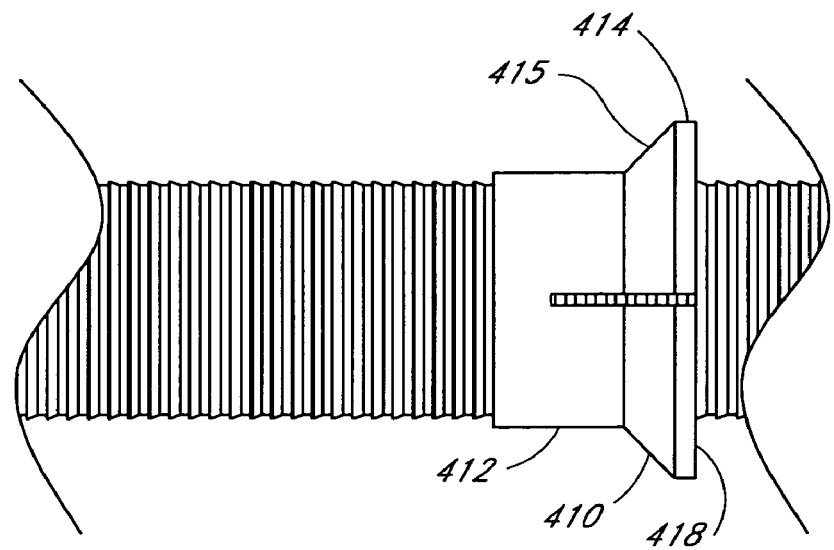
FIG. 21 is a side elevational view of the proximal anchor of FIG. 20.
Figure 22:
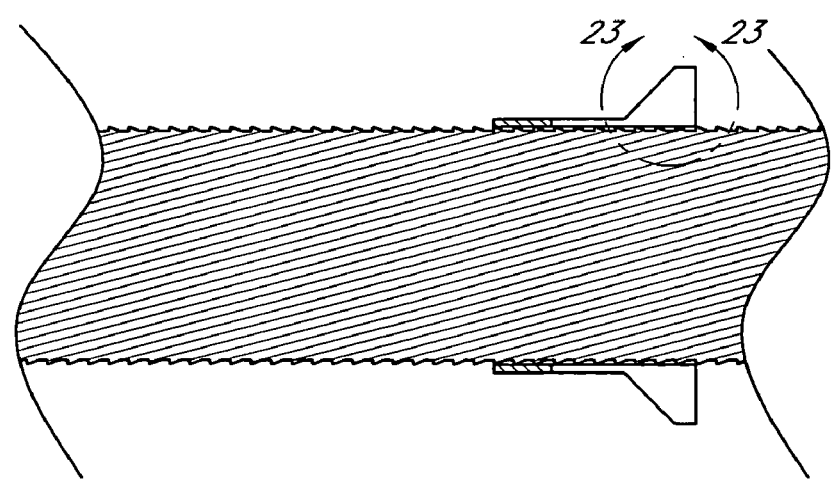
FIG. 22 is a longitudinal cross-sectional view of the proximal anchor of FIG. 20.

With initial reference to FIGS. 20 and 21, a proximal end of a fixation device 404 is illustrated. Although the distal anchor of the fixation device 404 is not illustrated, any of the bone anchors previously described or incorporated by reference herein may be used with the illustrated embodiment. Moreover, although the body 405 of the illustrated fixation device 404 is solid, the fixation device can be cannulated as mentioned above.

As described above, the proximal end of the body 405 is provided with a plurality of retention structures 406. The retention structures 406 are spaced apart axially along the fixation device between a proximal limit and a distal limit (not shown). As discussed above, the axial distance between proximal limit and distal limit is related to the desired axial travel of the proximal anchor, and thus the range of functional sizes of the bone fixation. In the illustrated embodiment, the retention structures 406 comprise a plurality of annular ridges or grooves, adapted to cooperate with complementary retention structures 408 on the proximal anchor 400, which will be described in detail below.

The proximal anchor 400 comprises a housing 412 such as a tubular body, for coaxial movement along the body 405. The proximal anchor 400 also includes a flange 414 that sets against the outer surface of the bone or tissue adjacent the bone as described above. As best seen in FIG. 21, the flange 414 defines a bone contacting surface 415, which preferably forms an obtuse angle with respect to the exterior of the housing 412.

Figure 23:
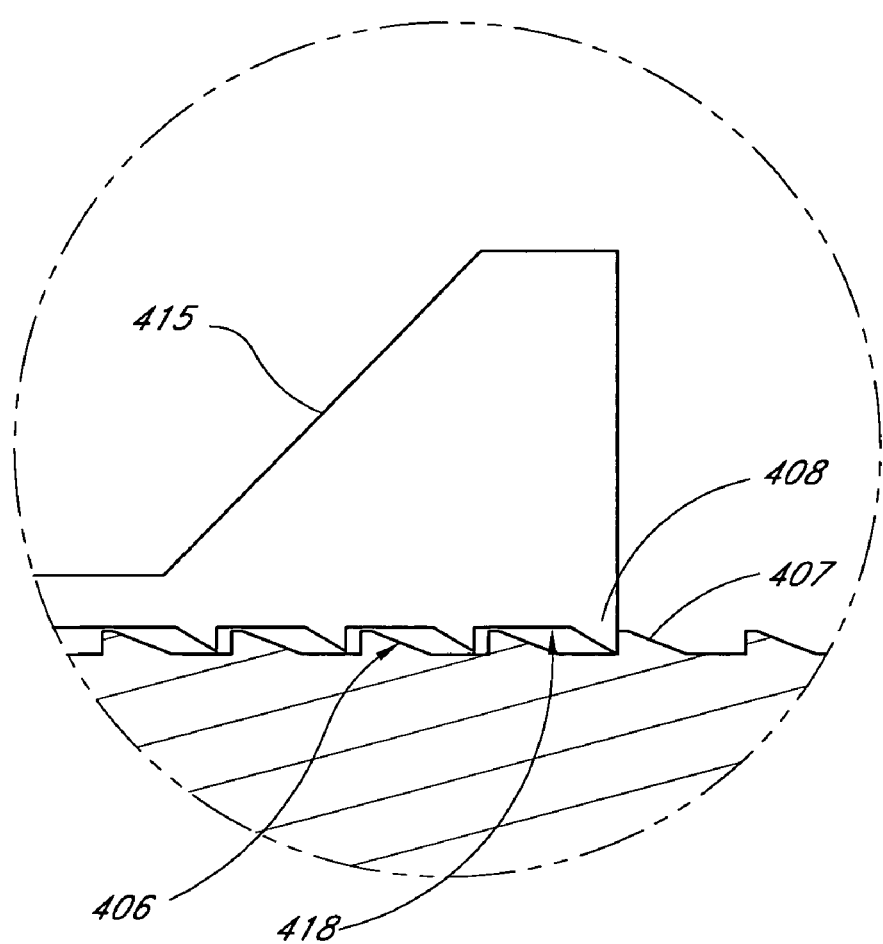
FIG. 23 is an enlarged detail view of a portion of the proximal anchor shown in FIG. 22.
Figure 23A:
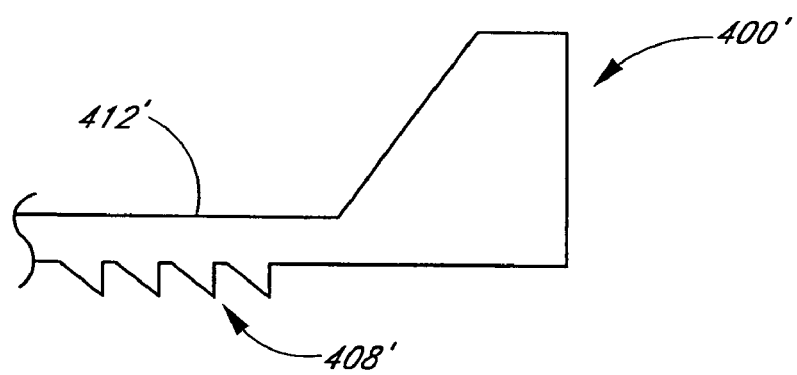
FIG. 23A is an enlarged detail view of a portion of a modified embodiment of the proximal anchor shown in FIG. 22.
Figure 24:
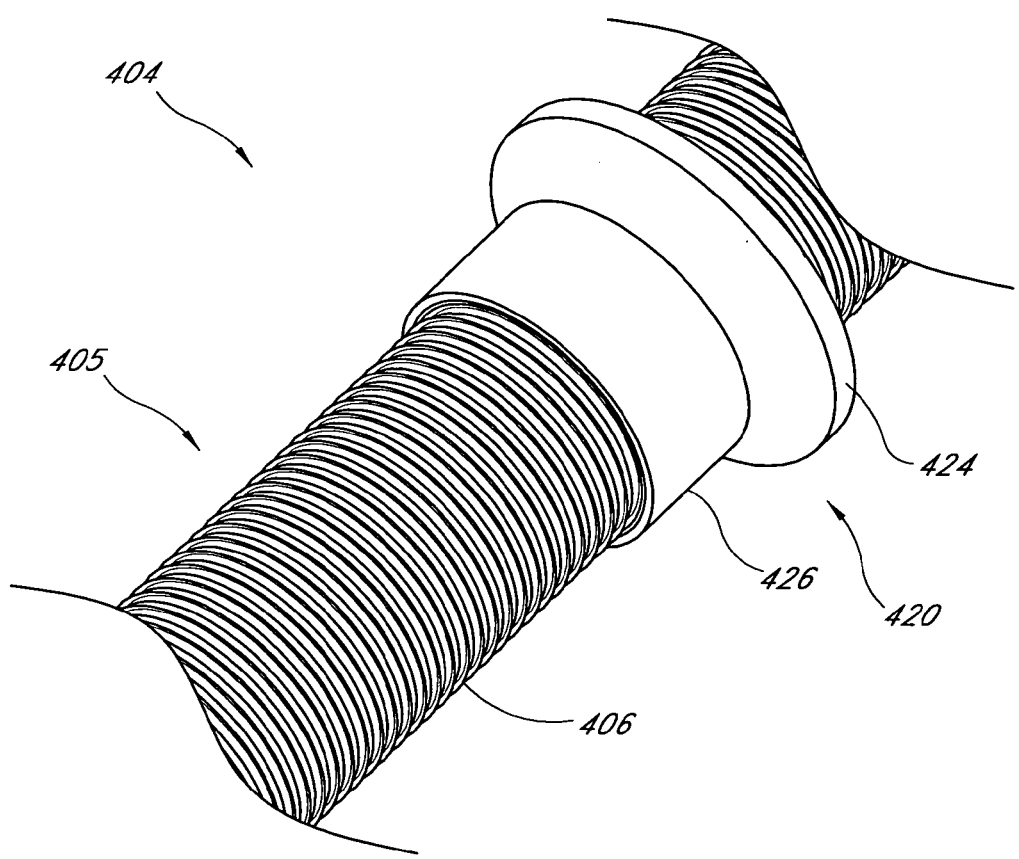
FIG. 24 is a perspective view of yet another embodiment of a proximal anchor.
Figure 25:
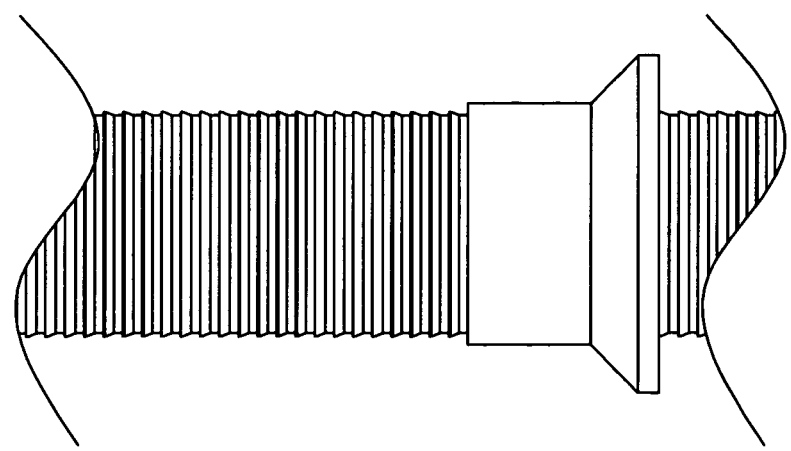
FIG. 25 is a side elevational view of the proximal anchor of FIG. 24.
Figure 26:
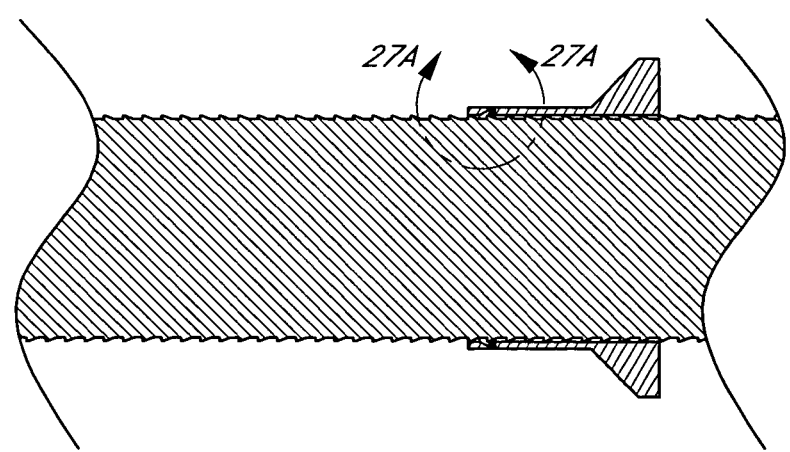
FIG. 26 is a longitudinal cross-sectional view of the proximal anchor of FIG. 24.

Referring to FIG. 23, in the illustrated embodiment, the complementary retention structures 408 comprise at least one inwardly projecting tooth or flange, for cooperating with the complementary rentention structures 406 of the fixation device 404. In the illustrated embodiment, the proximal anchor 400 includes a plurality of teeth or flanges 408, which are positioned near the proximal end of the anchor 400. FIG. 23A illustrates yet another modified embodiment of the proximal anchor of FIG. 23. In this embodiment, a plurality of teeth or flanges 408' are positioned near the distal end of the anchor 400'. In the embodiments of FIGS. 23 and 23A, it should be appreciated that the retention structures may be configured such that the proximal anchor may be proximally and/or distally advanced with rotation by providing for a screw like configuration between the retention structures. Additionally, the projecting teeth or flanges may be located at any suitable location for engaging the retention structures 406. Thus, a set or plurality of retention members can be located at any desirable position along the proximal anchor.

As mentioned above, the complementary retention structures 406 of the fixation device preferably comprise a plurality of annular ridges or grooves 406. As shown in FIG. 23, the plurality of annular ridges or grooves 406 preferably defines at least a first surface 407 and a second surface 409. The first surface 407 generally faces the proximal direction and is preferably inclined with respect to the longitudinal axis of the body 405. In contrast, the second surface 409 generally faces the distal direction and lies generally perpendicular to the longitudinal axis of the body 405.

As shown, in FIGS. 20 and 21, the proximal anchor 400 preferably includes one or more of axial slots 416. The axial slots 416 cooperate to form lever arms 418 (see FIG. 23) on which the teeth or projections 408 are positioned. Thus, as the anchor 400 is pushed towards the distal end of the body 305, the teeth 408 can slide along the first surface 407 and be lifted over the retention structures 406 of the body 405 as the lever arms 418 are flexed away from the body 405.

After appropriate tensioning of the proximal anchor 400, the bone pushes on the angled portion bone contacting surface 415 of the proximal anchor 400. This force is transmitted to the teeth 408 through the lever arms 418. As such, the teeth 408 are prevented from flexing away from the body 405, which keeps the teeth 408 engaged with the retention structures 406 of the body 405. By increasing the tensioning force, the teeth 408 are forced further into the retention structures 406 of the body 406, thereby increasing the retention force of the proximal anchor 400. In this manner, the teeth 408 cannot be lifted over the second surface 409 and proximal movement of the proximal anchor 400 is prevented.

The axial length and width of the slots 416 may be varied, depending upon the desired flexing of the lever arms 418 when the proximal anchor 400 is moved distally over the body 405 and the desired retention force of the distal anchor when appropriately tensioned. For a relatively rigid material such as titanium, axial lengths and widths of the slots 416 are approximately 0.5 mm for a proximal anchor having a length of approximately 4 mm, an inner diameter of approximately 3 mm. As such, in the illustrated embodiment, the slots 416 extend through the flange 414 and at least partially into the tubular housing 412.

Another embodiment of a proximal anchor 420 is illustrated in FIGS. 24–27B. The proximal anchor 420 includes a flange 424 and a tubular housing 426. In this embodiment, the complementary structure of the proximal anchor 420 comprises an annular ring 430, which is positioned within an annular recess 432 that is preferably positioned at the distal end of the tubular housing. See FIGS. 27A and 27B. The annular recess 432 includes a proximal portion 434 and a distal portion 436.

Figure 27A:
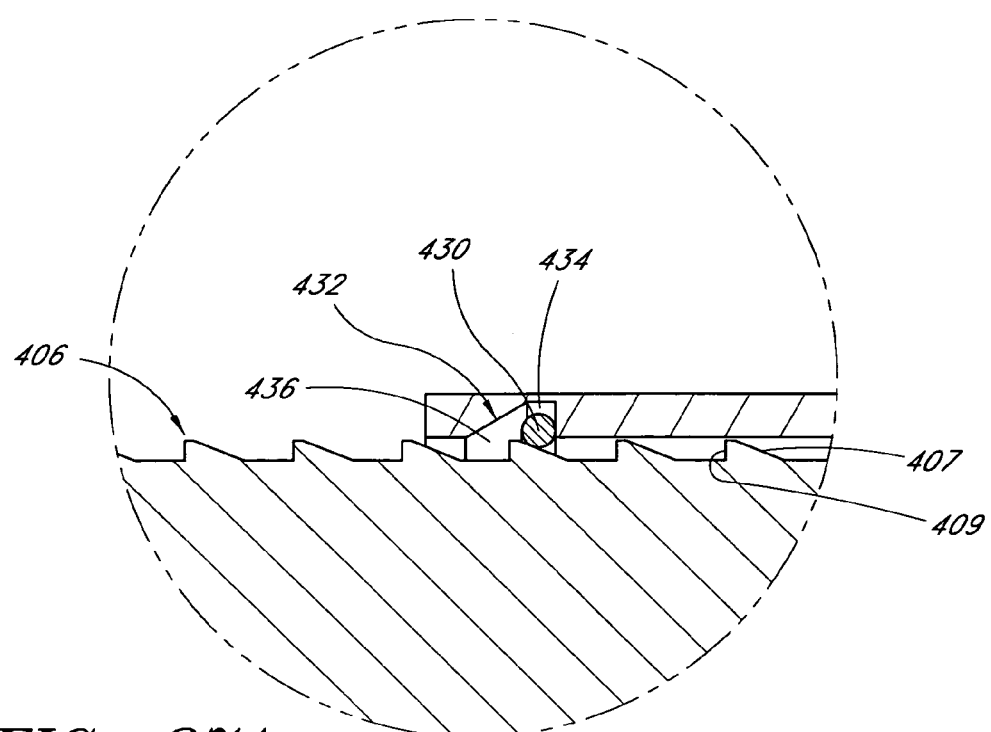
FIG. 27A is an enlarged detail view of a portion of the proximal anchor of FIG. 26 shown in a first position.

With specific reference to FIG. 27A, the proximal portion 434 is sized and dimensioned such that as the proximal anchor 420 is advanced distally over the body 405 the annular ring 430 can slide along the first surface 407 and over the complementary retention structures 406 of the body 405. That is, the proximal portion 434 provides a space for the annular ring to move radially away from the body 405 as the proximal anchor is advanced distally. Preferably, the annular ring 430 is made from a material that provides sufficient strength and elasticity such as, for example, stainless steel or titanium. The annular ring 430 is preferably split such that it can be positioned over the body 405. Although the ring 430 is illustrated as having a circular cross section, it may alternatively have a non circular cross section such as rectangular or square.

Figure 27B:
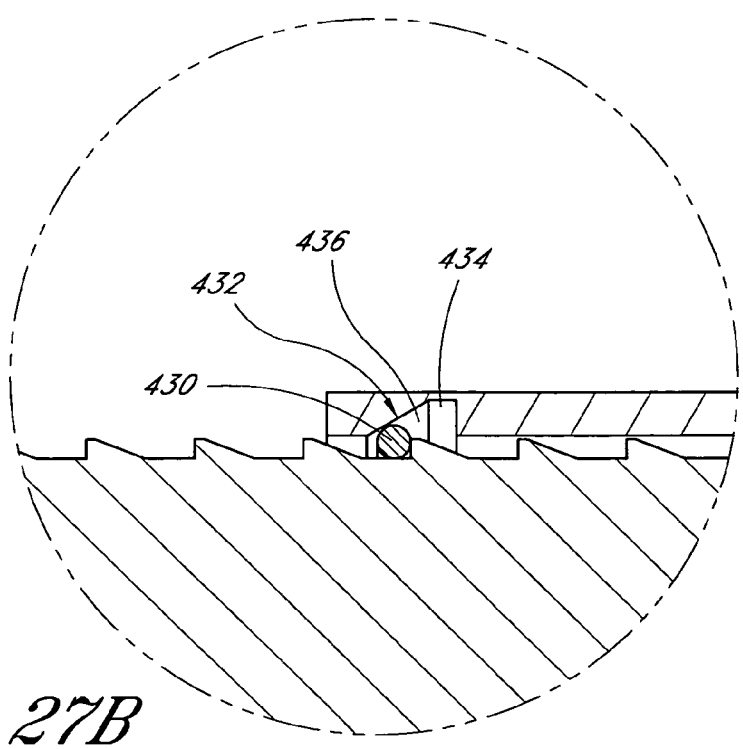
FIG. 27B is an enlarged detail view of a portion of the proximal anchor of FIG. 26 shown in a second position.

With reference to FIG. 27B, the distal portion 436 is sized and dimensioned such that after the proximal anchor 420 is appropriately tensioned the annular ring 430 becomes wedged between the second surface 409 and an angled engagement surface of the distal portion 436. In this manner, proximal movement of the proximal anchor 420 is prevented.

Figure 27C:
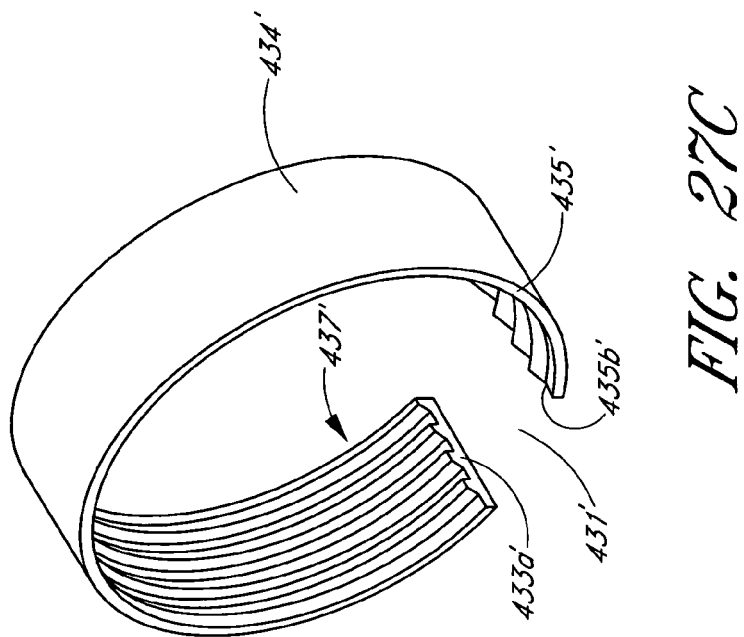
FIG. 27C is side perspective view of a portion of a modified embodiment of the proximal anchor shown in FIG. 26.
Figure 28:
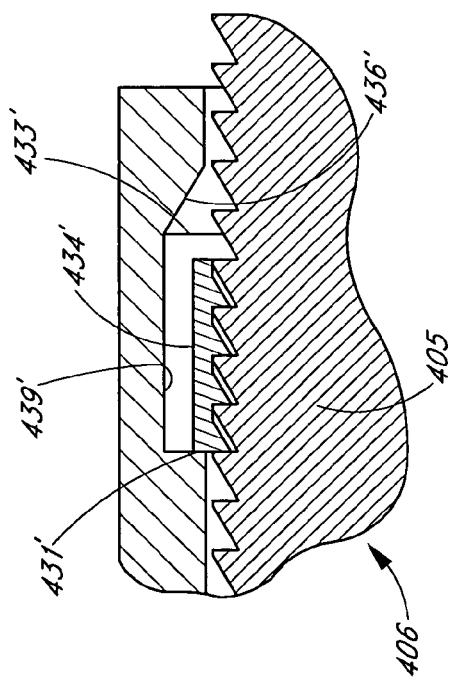
FIG. 28 is an enlarged longitudinal cross-sectional view of a modified embodiment of a proximal anchor with the portion illustrated in FIG. 27C.

FIGS. 27C and 28 illustrates a portion of modified embodiment of a proximal anchor that is similar to the embodiment described above with respect to FIGS. 27A–B. In this embodiment, proximal anchor includes an annular ring 434' that is split (i.e., has a least one gap) and can be interposed between the body 405 and the proximal recess 439' of the proximal anchor. The ring 434' comprises a tubular housing 435' that may be configured to engage with the body 405 and defines a gap or space 431'. In one embodiment, the gap 431' is defined by a pair of edges 433a', 433b'. The edges 433a', 433b' can be generally straight and parallel to each other. However, the edges 433a', 433b' can have any other suitable configuration and orientation. For example, in one embodiment, the edges 433a', 433b' are curved and at an angle to each other. Although not illustrated, it should be appreciated that in modified embodiments, the ring 434' can be formed without a gap. When the ring 434' is positioned along the body 405, the ring 434' preferably surrounds a substantial portion of the body 405. The ring 434' can be sized so that the ring 434' can flex or move radially outwardly in response to an axial force so that the ring 434' can be moved relative to the body 405, as described above. In one embodiment, the tubular housing 435' includes at least one and in the illustrated embodiment four teeth or flanges 437', which are configured to engage the retention structures 406 on the body 405. In the illustrated embodiment, the teeth or flanges include a first surface that generally faces the proximal direction and is inclined with respect to the longitudinal axis of the anchor and a second surface that faces distal direction and lies generally perpendicular to the longitudinal axis of the anchor. It is contemplated that the teeth or flanges 437' can have any suitable configuration for engaging with the retention structures of the body 405.

As with the previous embodiment, the proximal anchor includes the annular recess 439' in which the annular ring 434' may be positioned. The body 435' of the ring 434' can be sized to prevent substantial axial movement between the ring 434' and the annular recess 439' (FIG. 28) during use of the proximal anchor. In one embodiment, the width of the annular recess 439' in the axial direction is slightly greater than the width of the annular ring 434' in the axial direction. This tolerance between the annular recess 439' and the annular ring 434' can inhibit, or prevent, oblique twisting of the annular ring 434' so that the body 435' of the ring 434' is generally parallel to the outer surface of the body 405. Further, the recess 439' is sized and dimensioned such that as the proximal anchor is advanced distally over the body, the annular ring 434' can slide along the first surface and over the complementary retention structures of the body. That is, the recess 439' provides a space for the annular ring to move radially away from the body 405 as the proximal anchor is advanced distally. Of course, the annular ring 434' can be sized and dimensioned such that the ring 434' is biased inwardly to engage the retention structures 406 on the body 405. The bias of the annular ring 434' can result in effective engagement between the flanges 437' and the retention structures 406'.

A distal portion 436' of the recess 439' is sized and dimensioned such that after the proximal anchor 420 is appropriately tensioned the annular ring 434' becomes wedged between the body and an angled engagement surface of the distal portion 436'. In this manner, proximal movement of the proximal anchor is prevented.

Figure 29D:
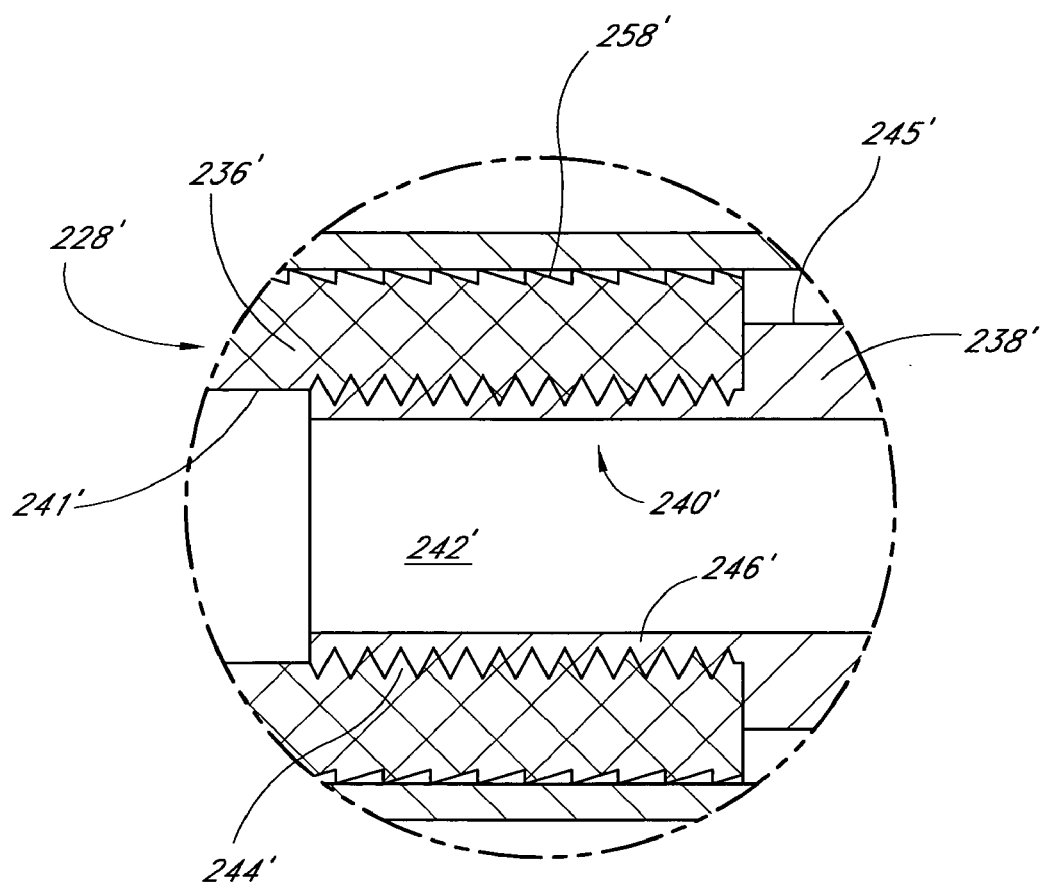
FIG. 29D is an enlarged portion of FIG. 29C.

FIGS. 29A–D illustrate a modified embodiment of the body 228' and proximal anchor 700. In this embodiment, the body 228' comprises a first portion 236' and a second portion 238' that are coupled together at a junction 240' (FIG. 29D). In the illustrated embodiment, the first portion 236' carries the distal anchor 234' while the second portion 238' forms the proximal end 230' of the body 228'. The first and second portions 236', 238' are preferably detachably coupled to each other at the junction 240'. In the illustrated embodiment, the first and second portions 236', 238' are detachably coupled to each other via interlocking threads. Specifically, as best seen in FIG. 29D, the body 228' includes an inner surface 241', which defines a central lumen 242' that preferably extends from the proximal end 230' to the distal end 232' throughout the body 228'. At the proximal end of the first portion 236', the inner surface 241' includes a first threaded portion 244'. The first threaded portion 244' is configured to mate with a second threaded portion 246', which is located on the outer surface 245' of the second portion 238'. The interlocking annular threads of the first and second threaded portions 244', 246' allow the first and second portions 236', 238' to be detachably coupled to each other. In one modified embodiment, the orientation of the first and second threaded portions 244', 246' can be reversed. That is, the first threaded portion 244' can be located on the outer surface of the first portion 236' and the second threaded portion 246' can be located on the inner surface 241' at the distal end of the second portion 238'. Any of a variety of other releasable complementary engagement structures may also be used, to allow removal of second portion 238' following implantation, as is discussed below.

In a modified arrangement, the second portion 238' can comprise any of a variety of tensioning elements for permitting proximal tension to be placed on the distal anchor 234' while the proximal anchor is advanced distally to compress the fracture. For example, any of a variety of tubes or wires can be removably attached to the first portion 236' and extend proximally to the proximal handpiece. In one such arrangement, the first portion 236' can include a releasable connector in the form of a latching element, such as an eye or hook. The second portion 238' can include a complementary releasable connector (e.g., a complementary hook or eye) for engaging the first portion 236'. In this manner, the second portion 238' can be detachably coupled to the first portion 236' such that proximal traction can be applied to the first portion 236' through the second portion as will be explained below. Alternatively, the second portion 238' may be provided with an eye or hook, or transverse bar, around which or through which a suture or wire may be advanced, both ends of which are retained at the proximal end of the device. Following proximal tension on the tensioning element during the compression step, one end of the suture or wire is released, and the other end may be pulled free of the device. Alternate releasable proximal tensioning structures may be devised by those of skill in the art in view of the disclosure herein.

With particular reference to FIGS. 29A-29D, the proximal end 230' of the body 228' may be provided with a rotational coupling 270', for allowing the second portion 238' of the body 228' to be rotationally coupled to a rotation device. The proximal end 230' of the body 228' may be desirably rotated to accomplish one or two discrete functions. In one application of the invention, the proximal end 230' is rotated to remove the second portion 238' of the body 228' following tensioning of the device across a fracture or to anchor an attachment to the bone. Rotation of the rotational coupling 270' may also be utilized to rotationally drive the distal anchor into the bone. Any of a variety of rotation devices may be utilized, such as electric drills or hand tools, which allow the clinician to manually rotate the proximal end 230' of the body. Thus, the rotational coupling 270' may have any of a variety of cross sectional configurations, such as one or more flats or splines.

With particular reference to FIG. 29A, the fixation device may include an antirotation lock between the first portion 236' of the body 228' and the proximal anchor 700. In the illustrated embodiment, the first portion 236' includes a pair of flat sides 280', which interact with corresponding flat structures 282' in the proximal anchor 700. One or three or more axially extending flats may also be used. As such, rotation of the proximal anchor 700 is transmitted to the first portion 236' and the distal anchor 234' of the body 228'. Of course, those of skill in the art will recognize various other types of splines or other interfit structures can be used to prevent relative rotation of the proximal anchor and the first portion 236' of the body 228'. For example, in one embodiment, the first portion 236' may include three flat sides, which interact with corresponding flat structures on the proximal anchor.

Figure 30A:
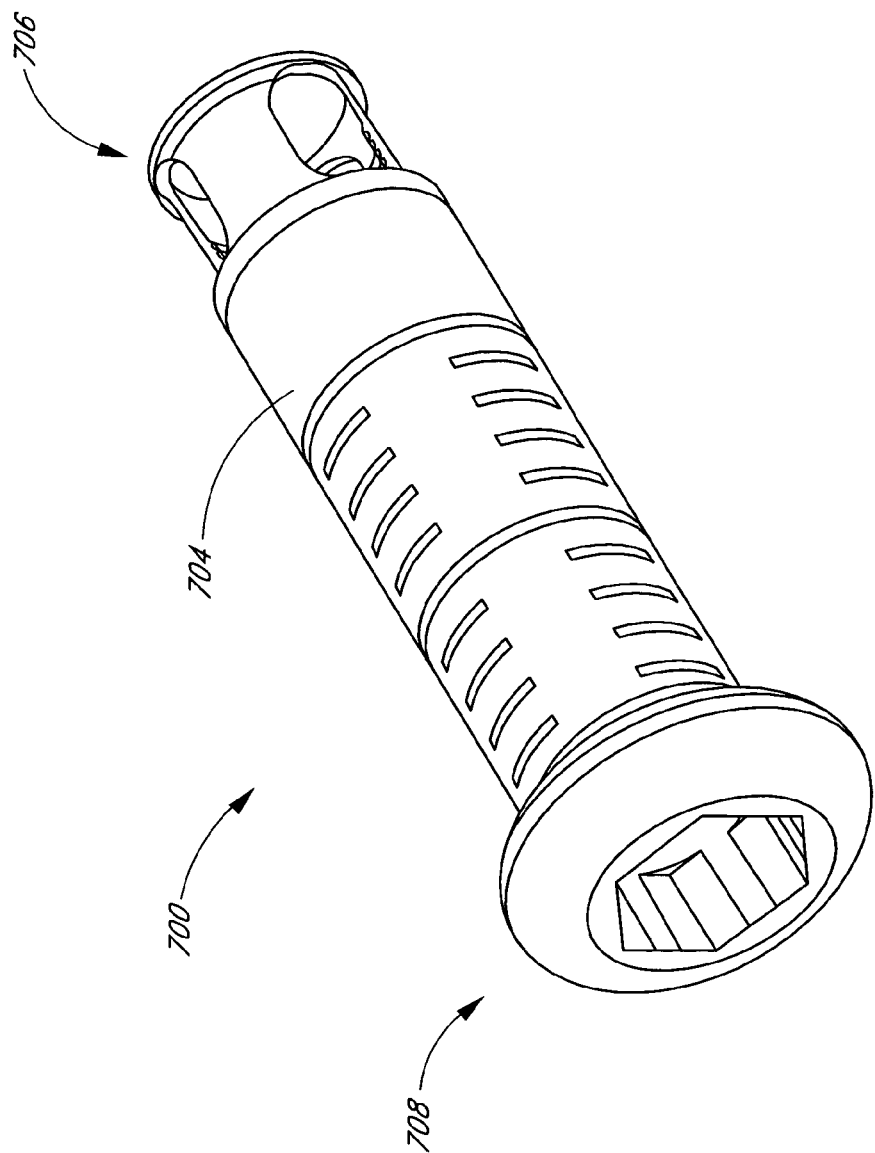
Figure 30B:
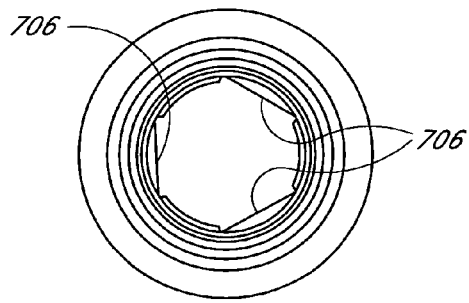
Figure 30B:
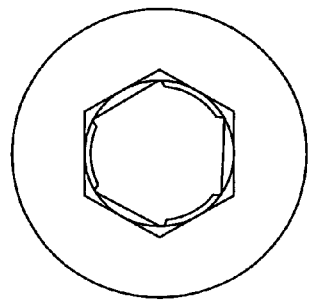
Figure 30B:
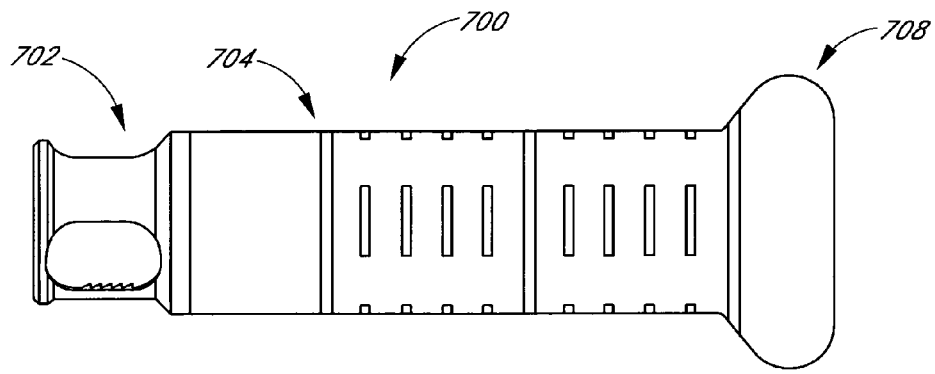
Figure 30C:
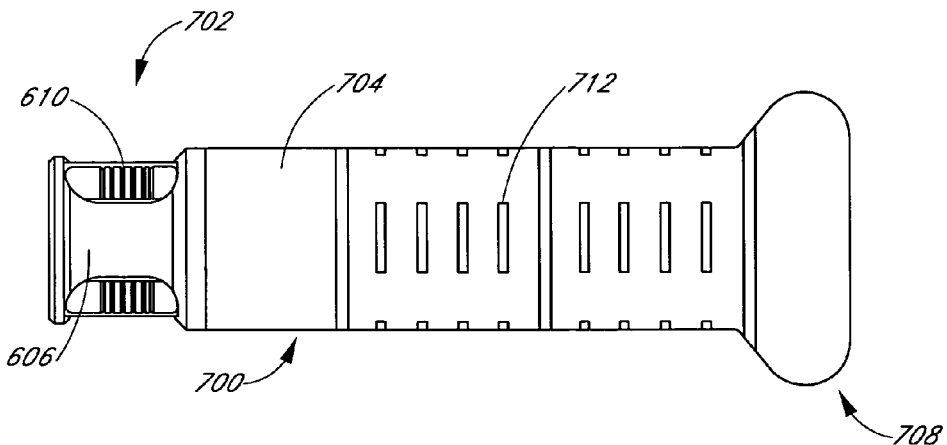
Figure 30F:
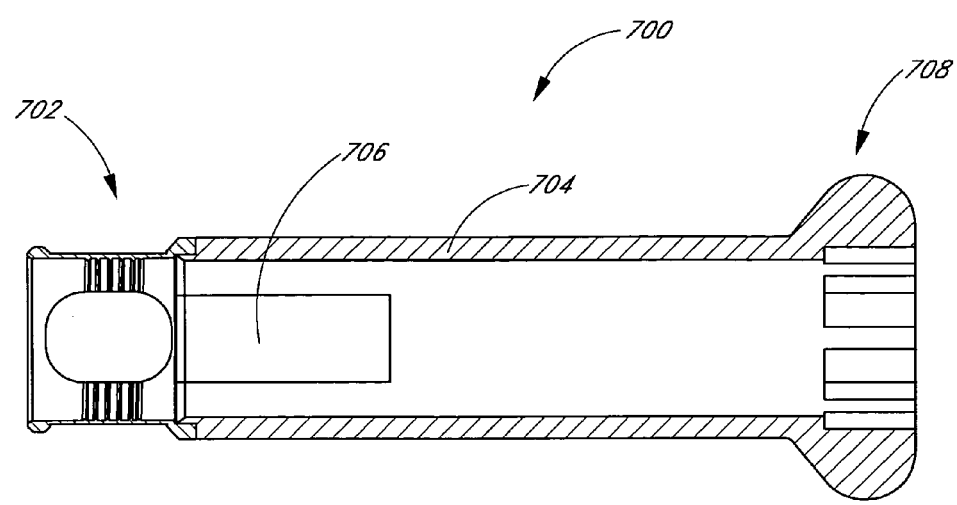

To rotate the proximal anchor 700, the flange 708 is preferably provided with a gripping structure to permit an insertion tool to rotate the flange 708. Any of a variety of gripping structures may be provided, such as one or more slots, flats, bores or the like. In one embodiment, the flange 708 is provided with a polygonal, and, in particular, a pentagonal or hexagonal recess 284'. See FIG. 30A.

In FIGS. 29B and 29C, the proximal anchor 700 is shown in combination with a washer 250' arranged as described above with reference to FIGS. 17A-C.

FIGS. 30A-F illustrate in more detail the a proximal anchor 700 of FIGS. 29A-C. This embodiment includes a tubular housing 702 similar to the tubular housing 602 described above with reference to FIGS. 12A-F. In the illustrated embodiment, the tubular housing 702 is attached to, coupled to, or integrally formed (partially or wholly) with a secondary tubular housing 704, which includes one or more anti-rotational features 706 (e.g., flat sides) for engaging corresponding anti-rotational features formed on the pin, which can be similar to the first portion 236' (e.g., see description above). The flange or collar 708 is attached, coupled or integrally formed with the proximal end of the secondary tubular housing. The teeth or flanges 610 on the bridges 606 may also be configured such that the proximal anchor may be distally advanced and/or removed with rotation. The illustrated embodiment also advantageously includes visual indicia 712 (e.g., marks, grooves, ridges etc.) on the tubular housing 704 for indicating the depth of the proximal anchor 700 within the bone.

In one embodiment of use, a fixation device 212' having an axial length and outside diameter suitable for the hole 280 is selected. The distal end 232' of the fixation device 212' is advanced distally into the hole 280 until the distal anchor 234' reaches the distal end of the hole 280. The proximal anchor 700 may be carried by the fixation device 212' prior to advancing the body 228' into the hole 280, or may be attached following placement of the body 228' within the hole 280. Once the body 228' and proximal anchor 700 are in place, the clinician may use any of a variety of driving devices, such as electric drills or hand tools to rotate the proximal anchor 700 and thus cancellous bone anchor 234' into the head of the femur. In modified embodiments, the fixation device is configured to be self-drilling or self tapping such that a hole does not have be formed before insertion into the bone.

Once the anchor 234' is in the desired location, proximal traction is applied to the proximal end 230' of body 228', such as by conventional hemostats, pliers or a calibrated loading device, while distal force is applied to the proximal anchor 700. In this manner, the proximal anchor 700 is advanced distally until the anchor 700 fits snugly against the outer surface of the femur or tissue adjacent the femur and the fracture 24 is completely reduced. Appropriate tensioning of the fixation device 212' is accomplished by tactile feedback or through the use of a calibration device for applying a predetermined load on the implantation device. One advantage of the structure of the present invention is the ability to adjust compression independently of the setting of the distal anchor 234'.

Following appropriate tensioning of the proximal anchor 700, the second portion 238' of the body 228' is preferably detached from the first portion 236' and removed. In the illustrated embodiment, this involves rotating the second portion 238' with respect to the first portion via the coupling 270'. Following removal of the second portion 238' of each body 228', the access site may be closed and dressed in accordance with conventional wound closure techniques.

An advantage certain embodiments of the fixation devices disclosed above is that the proximal anchor provides the device with a working range such that one device may accommodate varying distances between the distal anchor and the proximal anchor. In certain applications, this allows the technician to focus on the proper positioning of the distal anchor with the knowledge that the proximal anchor lies within the working range of the device. With the distal anchor positioned at the desired location, the proximal anchor may then be advanced along the body to compress the fracture and/or provide stability between bones. In a similar manner, the working range provides the technician with flexibility to adjust the depth of the proximal anchor. For example, in some circumstances, the bone may include voids, cysts osteoporotic bone that impairs the stability of the distal anchor in the bone. Accordingly, in some circumstances, the technician may advance the distal anchor and then desire to retract the distal anchor such that it is better positioned in the bone. In another circumstance, the technician may inadvertently advance the distal tip through the bone into a joint space. In such circumstances, the working range of the device allows the technician to reverse and retract the anchor and recompress connection. Such adjustments are facilitated by the working range of the proximal anchor on the body.

Preferably, the clinician will have access to an array of fixation devices (e.g., fixation devices 212, 212') having, for example, different diameters, axial lengths and angular relationships. These may be packaged one per package in sterile envelopes or peelable pouches, or in dispensing cartridges which may each hold a plurality of devices 212. Upon encountering a fracture for which the use of a fixation device is deemed appropriate, the clinician will assess the dimensions and load requirements, and select a fixation device from the array which meets the desired specifications.

The fixation devices described above may be used in any of a wide variety of anatomical settings beside the proximal femur, as has been discussed. For example, lateral and medial malleolar fractures can be readily fixed using the device of the present invention. Referring to FIG. 19, there is illustrated an anterior view of the distal fibula 320 and tibia 322. The fibula 320 terminates distally in the lateral malleolus 324, and the tibia 322 terminates distally in the medial malleolus 326. A fixation device 212 is illustrated as extending through the lateral malleolus 324 across the lateral malleolar fracture 328 and into the fibula 320. Fixation device 212 includes a distal anchor 34 for fixation within the fibula 320, an elongate body 228 and a proximal anchor as has been discussed.

As mentioned above, the devices describe herein may also be used for spinal fixation. In embodiments optimized for spinal fixation in an adult human population, the body 228 will generally be within the range of from about 20–90 mm in length and within the range of from about 3.0–8.5 mm in maximum diameter. The length of the helical anchor, discussed above, may be about 8–80 millimeters. Of course, it is understood that these dimensions are illustrative and that they may be varied as required for a particular patient or procedure.

In spinal fixation applications, the fixation device 212 may be used as a trans-facet screw. That is, the fixation device extends through a facet of a first vertebra and into the facet of a second, typically inferior, vertebrae. This procedure is typically (but not necessarily) preformed with bilateral symmetry. Thus, even in the absence of a stabilizing bar tying pedicle screws to adjacent vertebrae or to the sacrum, and in the absence of translaminar screws that can extend through the spinous process, the fixation devices can be used to stabilize two vertebrae, such as L3 and L4 to each other pending the healing of a fusion. In one embodiment, the body 228 of fixation device 228 has a length of approximately 10 mm –30 mm and the diameter of the body is approximately 3 mm to 5.5 mm.

The fixation device 212 may also be used as a translaminar facet screw. In this embodiment of use, the fixation device extends through the spinous process and facet of a first vertebra and into the facet of a second, typically inferior, vertebra. As with the previous embodiment, this procedure is typically (but not necessarily) preformed with bilateral symmetry. In one embodiment, the body 228 of fixation device 212 has a length of approximately 50 mm–90 mm and the diameter of the body is approximately 4 mm to 5.5 mm.

The fixation device may also be used is used as a facet-pedical screw (e.g., as used in the Boucher technique). In such an embodiment, the fixation device extends through the facet of a first vertebra and into the pedicle a second, typically inferior, vertebra. As with the previous embodiment, this procedure is typically (but not necessarily) preformed with bilateral symmetry. In such an embodiment, the fixation device 212 and the body 228 is approximately 20–40 millimeters in length and 3.0–5.5 millimeters in diameter.

FIGS. 31A–D illustrate another embodiment of a proximal anchor 800. In this embodiment, the proximal anchor 800 includes a recess 839 configured to receive a split ring 434' as described above with reference to FIGS. 27C and 28. As will be explained in detail below, the proximal anchor 800 includes an anti-rotation feature to limit or prevent rotation of the ring 434' within the proximal anchor 800. In light of the disclosure herein, those of skill in the art will recognize various different configurations for limiting the rotation of the ring 434'. However, a particularly advantageous arrangement will be described below with reference to the illustrated embodiment.

Figure 31A:
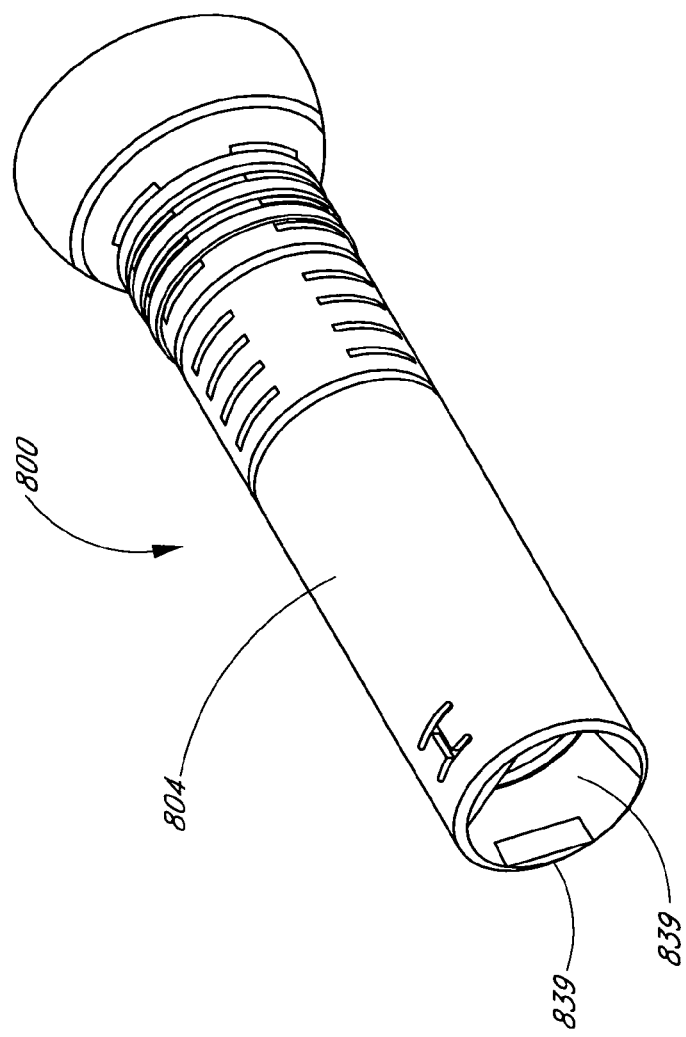
FIG. 31A is a perspective view of another embodiment of a proximal anchor.
Figure 31C:
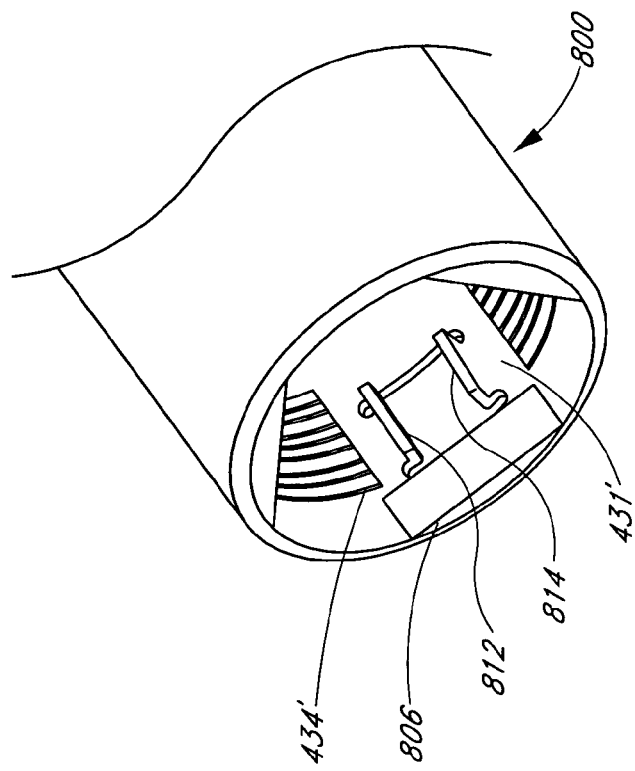
FIGS. 31B and 31C are enlarged views of a portion of one embodiment of a proximal anchor.
Figure 31B:
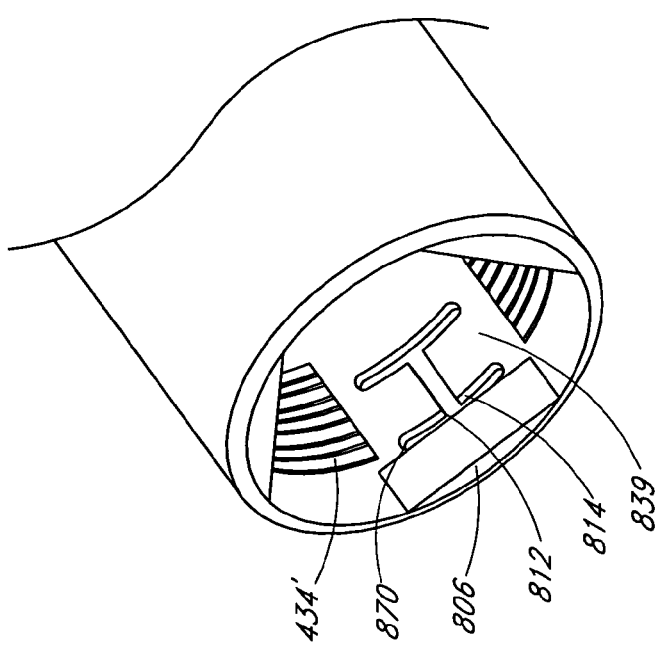
Figure 31D:
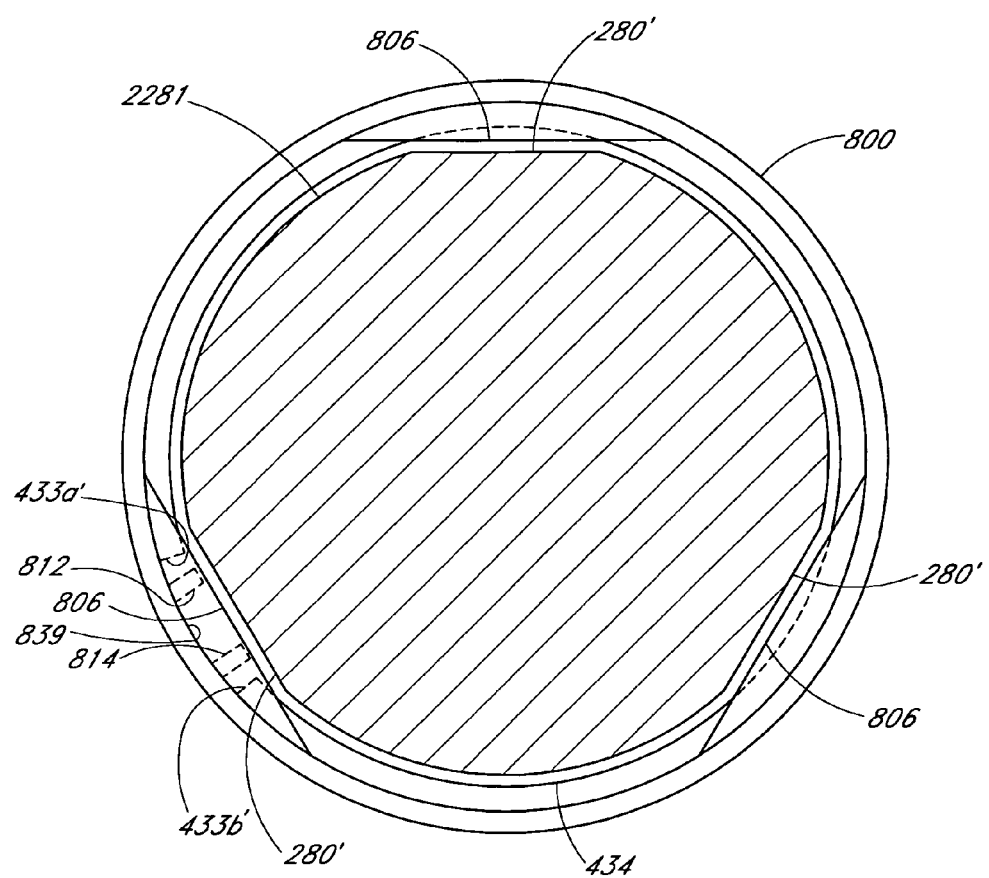
FIG. 31D is a front view of the proximal anchor of FIG. 31A.

In the illustrated embodiment, the proximal anchor 800 has a tubular housing 804 that can engage with a body 228 or a first portion 236' of a body 228' as described above. With reference to FIGS. 31B and 31D, the tubular housing 804 comprises one or more anti-rotational features 806 in the form of a plurality of flat sides that are configured to mate corresponding anti-rotational features 280' or flat sides of the body 228' of the fixation device. As shown in FIG. 31D, in the illustrated embodiment, the body 228' has three flat sides 280'. Disposed between the flat sides 280 are the portions of the body 228' which include the complementary locking structures such as threads or ratchet like structures as described above. The complementary locking structures interact with the ring 434' as described above to resist proximal movement of the anchor 800 under normal use conditions while permitting distal movement of the anchor 800 over the body 228.

As mentioned above, the ring 434' is positioned within the recess 839. In the illustrated embodiment, the recess 839 and ring 434' are positioned near to and proximal of the anti-rotational features 806. However, the ring 434' can be located at any suitable position along the tubular housing 804 such that the ring 434' can interact with the retention features of the body.

During operation, the ring 434' may rotate to a position such that the gap 431' between the ends 433a', 433b' of the ring 434' lies above the complementary retention structures on the body 228'. When the ring 434' is in this position, there is a reduced contact area between the split ring 434' the complementary retention structures thereby reducing the locking strength between the proximal anchor 800 and the body 228'. In the illustrated embodiment, for example, the locking strength may be reduced by about ⅓ when the gap 431' over the complementary retention structures between flat sides 280'. As such, it is advantageous to position the gap 431' on the flat sides 280' of the body 228' that do not include complementary retention structures.

To achieve this goal, the illustrated embodiment includes a pair of tabs 812, 814 that extend radially inward from the interior of the proximal anchor 800. The tabs 812, 814 are configured to limit or prevent rotational movement of the ring 434' relative to the housing 804 of the anchor 800. In this manner, the gap 431' of the ring 434' may be positioned over the flattened sides 280' of the body 228'.

In the illustrated embodiment, the tabs 812, 814 have a generally rectangular shape and have a generally uniform thickness. However, it is contemplated that the tabs 812, 814 can be square, curved, or any other suitable shape for engaging with the ring 434' as described herein.

In the illustrated embodiment, the tabs 812, 814 are formed by making an H-shaped cut 870 in the tubular housing 800 and bending the tabs 812, 814 inwardly as shown in FIG. 31D. As shown in FIG. 31D, the tabs 812, 814 (illustrated in phantom) are interposed between the edges 433a', 433b' of the ring 434'. The edges 433a', 433b' of the ring 434' can contact the tabs to limit the rotational movement of the ring 434'. Those skilled in the art will recognize that there are many suitable manners for forming the tabs 812, 814. In addition, in other embodiments, the tabs 812, 814 may be replaced by a one or more elements or protrusions attached to or formed on the interior of the proximal anchor 800.

For the embodiments discussed herein, the pin, together with the distal anchor and other components of the present invention can be manufactured in accordance with any of a variety of techniques which are well known in the art, using any of a variety of medical-grade construction materials. For example, the pin body and other components of the present invention can be injection-molded from a variety of medical-grade polymers including high or other density polyethylene, nylon and polypropylene. The distal anchor can be separately formed from the pin body and secured thereto in a post-molding operation, using any of a variety of securing techniques such as solvent bonding, thermal bonding, adhesives, interference fits, pivotable pin and aperture relationships, and others known in the art. Preferably, however, the distal anchor is integrally molded with the pin body, if the desired material has appropriate physical properties.

Retention structures can also be integrally molded with the pin body. Alternatively, retention structures can be machined or pressed into the pin body in a post-molding operation, or secured using other techniques depending upon the particular design.

A variety of polymers which may be useful for the anchor components of the present invention are identified below. Many of these polymers have been reported to be biodegradable into water-soluble, non-toxic materials which can be eliminated by the body:

Polycaprolactone
Poly (L-lactide)
Poly (DL-lactide)
Polyglycolide
Poly (L-Lactide-co-D, L-Lactide)
70:30 Poly (L-Lactide-co-D, L-Lactide)
95:5 Poly (DL-lactide-co-glycolide)
90:10 Poly (DL-lactide-co-glycolide)
85:15 Poly (DL-lactide-co-glycolide)
75:25 Poly (DL-lactide-co-glycolide)
50:50 Poly (DL-lactide-co-glycolide)
90:10 Poly (DL-lactide-co-caprolactone)
75:25 Poly (DL-lactide-co-caprolactone)
50:50 Poly (DL-lactide-co-caprolactone)
Polydioxanone
Polyesteramides
Copolyoxalates
Polycarbonates
Poly (glutamic-co-leucine)

The desirability of any one or a blend of these or other polymers can be determined through routine experimentation by one of skill in the art, taking into account the mechanical requirements, preferred manufacturing techniques, and desired reabsorption time. Optimization can be accomplished through routine experimentation in view of the disclosure herein.

Alternatively, the anchor components can be molded, formed or machined from biocompatible metals such as Nitinol, stainless steel, titanium, and others known in the art. In one embodiment, the components of the bone fixation device 24 are injection-molded from a bioabsorbable material, to eliminate the need for a post-healing removal step. One suitable bioabsorbable material which appears to exhibit sufficient structural integrity for the purpose of the present invention is poly-p-dioxanone, such as that available from the Ethicon Division of Johnson & Johnson. Poly (L-lactide, or co-DL-lactide) or blends of the two may alternatively be used. As used herein, terms such as bioabsorbable, bioresorbable and biodegradable interchangeably refer to materials which will dissipate in situ, following a sufficient bone healing period of time, leaving acceptable byproducts. All or portions of any of the devices herein, as may be appropriate for the particular design, may be made from allograft material, or synthetic bone material as discussed elsewhere herein.

The bioabsorbable implants of this invention can be manufactured in accordance with any of a variety of techniques known in the art, depending upon the particular polymers used, as well as acceptable manufacturing cost and dimensional tolerances as will be appreciated by those of skill in the art in view of the disclosure herein. For example, any of a variety of bioabsorbable polymers, copolymers or polymer mixtures can be molded in a single compression molding cycle, or the surface structures can be machined on the surface of the pin or sleeve after the molding cycle. It is also possible to use the techniques of U.S. Pat. No. 4,743,257, the entire disclosure of which is incorporated herein by reference, to mold absorbable fibers and binding polymers together, to create a fiber-reinforced absorbable anchor.

An oriented or self-reinforced structure for the anchor can also be created during extrusion or injection molding of absorbable polymeric melts through a suitable die or into a suitable mold at high speed and pressure. When cooling occurs, the flow orientation of the melt remains in the solid material as an oriented or self-reinforcing structure. The mold can have the form of the finished anchor component, but it is also possible to manufacture the anchor components of the invention by machining injection-molded or extruded semifinished products. It may be advantageous to make the anchors from melt-molded, solid state drawn or compressed, bioabsorbable polymeric materials, which are described, e.g., in U.S. Pat. Nos. 4,968,317 and 4,898,186, the entire disclosures of which are incorporated herein by way of this reference.

Reinforcing fibers suitable for use in the anchor components of the present invention include ceramic fibers, like bioabsorbable hydroxyapatite or bioactive glass fibers. Such bioabsorbable, ceramic fiber reinforced materials are described, e.g., in published European Patent Application No. 0146398 and in WO/96/21628, the entire disclosures of which are incorporated herein by way of this reference.

As a general feature of the orientation, fiber-reinforcement or self-reinforcement of the anchor components, many of the reinforcing elements are oriented in such a way that they can carry effectively the different external loads (such as tensile, bending and shear loads) that are directed to the anchor as used.

The oriented and/or reinforced anchor materials for many applications have tensile strengths in the range of about 100–2000 MPa, bending strengths in the range of about 100–600 MPa and shear strengths in the range of about 80–400 MPa, optimized for any particular design and application. Additionally, they are relatively stiff and tough. These mechanical properties may be superior to those of non-reinforced or non-oriented absorbable polymers, which often show strengths between about 40 and 100 MPa and are additionally may be flexible or brittle. See, e.g., S. Vainionpaa, P. Rokkanen and P. Tornmld, "Surgical Applications of Biodegradable Polymers in Human Tissues", Progr. Polym. Sci., Vol. 14, (1989) at 679–716, the full disclosure of which is incorporated herein by way of this reference.

The anchor components of the invention (or a bioabsorbable polymeric coating layer on part or all of the anchor surface), may contain one or more bioactive substances, such as antibiotics, chemotherapeutic substances, angiogenic growth factors, substances for accelerating the healing of the wound, growth hormones, antithrombogenic agents, bone growth accelerators or agents, and the like. Such bioactive implants may be desirable because they contribute to the healing of the injury in addition to providing mechanical support.

In addition, the anchor components may be provided with any of a variety of structural modifications to accomplish various objectives, such as osteoincorporation, or more rapid or uniform absorption into the body. For example, osteoincorporation may be enhanced by providing a micropitted or otherwise textured surface on the anchor components. Alternatively, capillary pathways may be provided throughout the pin and collar, such as by manufacturing the anchor components from an open cell foam material, which produces tortuous pathways through the device. This construction increases the surface area of the device which is exposed to body fluids, thereby generally increasing the absorption rate. Capillary pathways may alternatively be provided by laser drilling or other technique, which will be understood by those of skill in the art in view of the disclosure herein. In general, the extent to which the anchor can be permeated by capillary pathways or open cell foam passageways may be determined by balancing the desired structural integrity of the device with the desired reabsorption time, taking into account the particular strength and absorption characteristics of the desired polymer.

One open cell bioabsorbable material is described in U.S. Pat. No. 6,005,161 as a poly(hydroxy) acid in the form of an interconnecting, open-cell meshwork which duplicates the architecture of human cancellous bone from the iliac crest and possesses physical property (strength) values in excess of those demonstrated by human (mammalian) iliac crest cancellous bone. The gross structure is said to maintain physical property values at least equal to those of human, iliac crest, cancellous bone for a minimum of 90 days following implantation. The disclosure of U.S. Pat. No. 6,005,161 is incorporated by reference in its entirety herein.

The anchors of the present invention may be sterilized by any of the well known sterilization techniques, depending on the type of material. Suitable sterilization techniques include heat sterilization, radiation sterilization, such as cobalt 60 irradiation or electron beams, ethylene oxide sterilization, and the like.

The specific dimensions of any of the bone fixation devices of the present invention can be readily varied depending upon the intended application, as will be apparent to those of skill in the art in view of the disclosure herein. Moreover, although the present invention has been described in terms of certain preferred embodiments, other embodiments of the invention including variations in the number of parts, dimensions, configuration and materials will be apparent to those of skill in the art in view of the disclosure herein. In addition, all features discussed in connection with any one embodiment herein can be readily adapted for use in other embodiments herein to form various combinations and sub-combinations. The use of different terms or reference numerals for similar features in different embodiments does not imply differences other than those which may be expressly set forth. Accordingly, the present invention is intended to be described solely by reference to the appended claims, and not limited to the preferred embodiments disclosed herein.

We claim:

1. An orthopedic fixation device, comprising:
   an elongate body, having a proximal end and a distal end;
   a distal anchor on the distal end;
   a retention structure on the elongate body, proximal to the anchor; and
   a proximal anchor, moveably carried by the elongate body, the proximal anchor comprising a tubular sleeve and a radially outward extending head;
   at least one complementary retention structure on the proximal anchor configured for permitting proximal movement of the elongate body with respect to the proximal anchor but resisting distal movement of the elongate body with respect the proximal anchor; and
   a washer that is angularly moveable with respect to the longitudinal axis of the tubular sleeve, the washer having aperture that is elongated with respect to a first axis such that the washer permits greater angular movement with respect to the longitudinal axis of the tubular sleeve in a plane containing the first axis.

2. The orthopedic fixation device of claim 1, wherein the aperture circumscribes a channel having a width in a first direction and a height in a second direction that is perpendicular to the first direction, the width being smaller than the maximum diameter of the head and the height being greater than the width.

3. The orthopedic fixation device of claim 1, wherein the distal anchor comprises a helical flange.

4. The orthopedic fixation device of claim 1, wherein the distal anchor is moveable from an axial orientation for distal insertion through a bore to an incline orientation to resist axial movement through the bore.

5. The orthopedic fixation device of claim 1, wherein the retention structures of the elongate body and the proximal anchor permit proximal movement of the elongate body with respect to the proximal anchor without rotation.

6. The orthopedic fixation device of claim 1, wherein the washer includes a bottom wall, a side wall and a lip for retaining the head of the proximal anchor within the washer.

7. The orthopedic fixation device of claim 1, wherein the elongated body comprises a first portion and a second portion that are detachably coupled together at a junction.

8. The orthopedic fixation device of claim 7, wherein the first portion includes an anti-rotation structure and the proximal anchor includes a complementary anti-rotation structure to prevent rotation between the first portion and the proximal anchor.

9. An orthopedic fixation device;
   an elongate pin, having a proximal end, a distal end and a first retention structure;
   at least one distal anchor carried by the elongate pin;
   a proximal anchor, axially moveable with respect to the elongate pin and comprising a split ring positioned within an annular recess formed within the proximal anchor, the split ring having at least one gap formed between two ends, the split ring being moveable between a first position and a second position, the second position being located closer to the longitudinal axis of the elongate pin as compared to the first position so as to engage the first retention structure and prevent proximal movement of the proximal anchor with respect to the elongated pin while the first position allows distal movement of the proximal anchor with respect to the pin; and anti-rotational structure for preventing rotation of the split ring about the longitudinal axis of the elongate pin.

10. The orthopedic fixation device as in claim 9, wherein the elongate pin includes at least one anti-rotational feature configured to engage a complementary rotational feature of the proximal anchor.

11. The orthopedic fixation device as in claim 10, wherein the anti-rotational structure positions the gap of the split ring such that it is positioned over the anti-rotational feature of the elongate pin.

12. The orthopedic fixation device as in claim 11, wherein the anti-rotational feature of the elongate pin comprises at least one flat side.

13. The orthopedic fixation device as in claim 11, wherein the anti-rotational feature comprise includes a pair of tabs that extend inwardly from the tubular body toward the longitudinal axis of the tubular body and positioned between the gap of the split ring.

14. The orthopedic fixation device of claim 9, wherein the distal anchor comprises a helical flange.

15. The orthopedic fixation device of claim 9, wherein the distal anchor is moveable from an axial orientation for distal insertion through a bore to an incline orientation to resist axial movement through the bore.

16. The orthopedic fixation device of claim 9, wherein the elongate pin comprises a first portion and a second portion that are detachably coupled together at a junction.

17. The orthopedic fixation device of claim 16, wherein the first portion includes an anti-rotation structure and the proximal anchor includes a complementary anti-rotation structure to prevent rotation between the first portion and the proximal anchor.

* * * * *